United States Patent [19]

Lo

[11] Patent Number: 5,242,820
[45] Date of Patent: Sep. 7, 1993

[54] PATHOGENIC MYCOPLASMA

[75] Inventor: Shyh-Ching Lo, Potomac, Md.

[73] Assignee: American Registry of Pathology, Washington, D.C.

[21] Appl. No.: 710,361

[22] Filed: Jun. 6, 1991

Related U.S. Application Data

[63] Continuation-in-part of Ser. No. 265,920, Nov. 2, 1988, abandoned, which is a continuation-in-part of Ser. No. 875,535, Jun. 18, 1986, abandoned.

[51] Int. Cl.$^5$ .................. C12N 5/00; C12N 5/02; C12N 1/00; C12Q 1/70
[52] U.S. Cl. .................... 435/240.2; 435/5; 435/872
[58] Field of Search ............. 435/870, 5, 872, 240.2

[56] References Cited

PUBLICATIONS

Marquart et al (1985) Mycoplasma-Like Structures ... Eur J Clin Microbiol 4(1):73-74.
Lo et al (1989) A Novel Virus-like Infectious Agent ... Am J Trop Med Hyg 40(2):213-226.
Lo et al (1989) Identification of *M Incognitus* ... Am. J. Trop-Med. Hyg 41(5):601-616.
Lo et al (1989) Association of the Virus-like Agent ... Am J Trop Med Hyg 41(3):364-376.
Lo et al (1989) Fatal Infection of Silvered Leaf Monkeys ... Am. T Trop Med Hyg 40(4):399-409.
Lo et al (1989) Virus-like Infectious Agent ... Am J Trop Med Hyg 41(5):586-600.
Marquart et al (Feb. 1985) Abstract Only Eur J Clin Microbiol 4(1):73-74.
Hu et al (1990) Gene 93:67-72.

*Primary Examiner*—Christine M. Nucker
*Assistant Examiner*—D. R. Preston
*Attorney, Agent, or Firm*—Venable, Baetjer, Howard & Civiletti

[57] ABSTRACT

The invention relates to a novel pathogenic mycoplasma isolated from patients with Acquired Immune Deficiency Syndrome (AIDS) and its use in detecting antibodies in sera of AIDS patients, patients with AIDS-related complex (ARC) or patients dying of diseases and symptoms resembling AIDS diseases. The invention further relates to specific DNA sequences, antibodies against the pathogenic mycoplasma, and their use in detecting DNA or antigens of the pathogenic mycoplasma or other genetically and serologically closely related mycoplasmas in infected tissue of patients with AIDS or ARC or patients dying of symptoms resembling AIDS diseases. The invention still further relates to a variety of different forms of vaccine against mycoplasma infection in humans and/or animals.

2 Claims, 39 Drawing Sheets 1 2 3 4 5 6 7 8

1 2 3 4 5 6 7 8

1 2 3 4 5 6 7 8

1 2 3 4 5 6 7 8

1 2 3 4 5 6 7 8

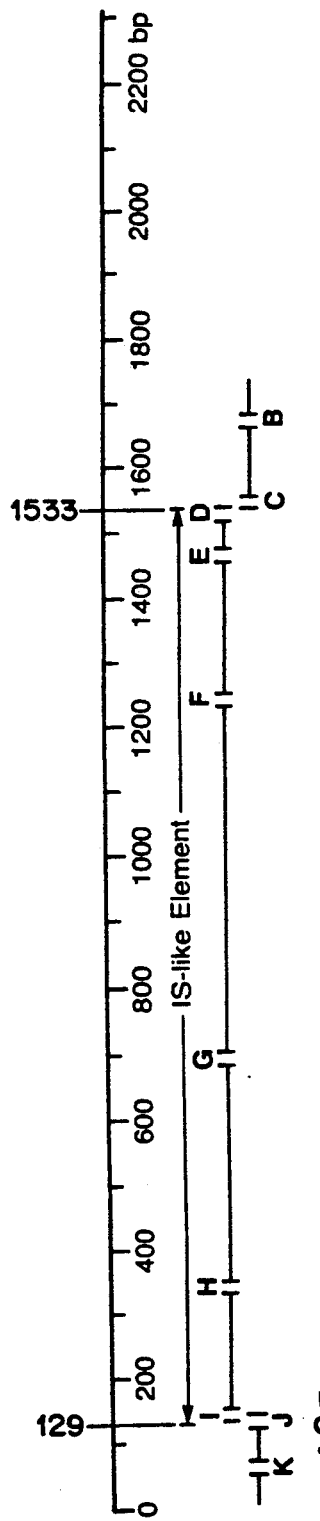
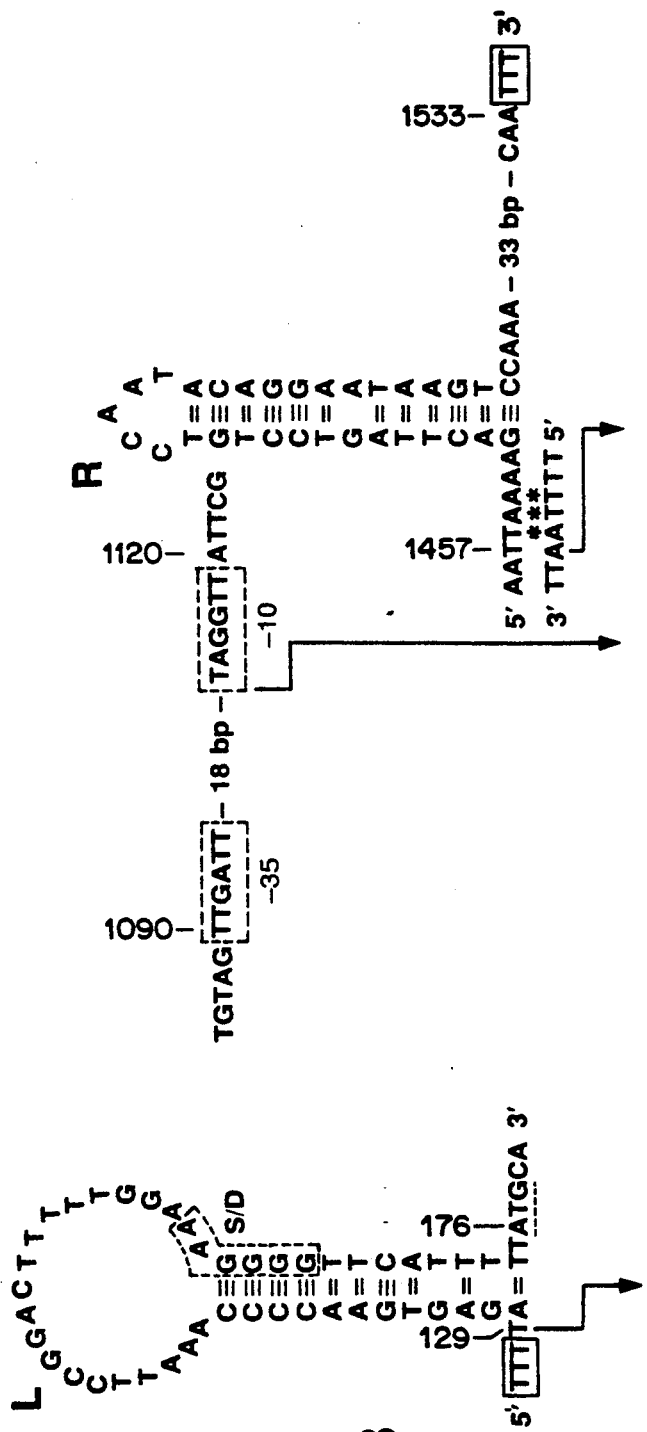
FIG. 5A
FIG. 5B

FIG. 10A
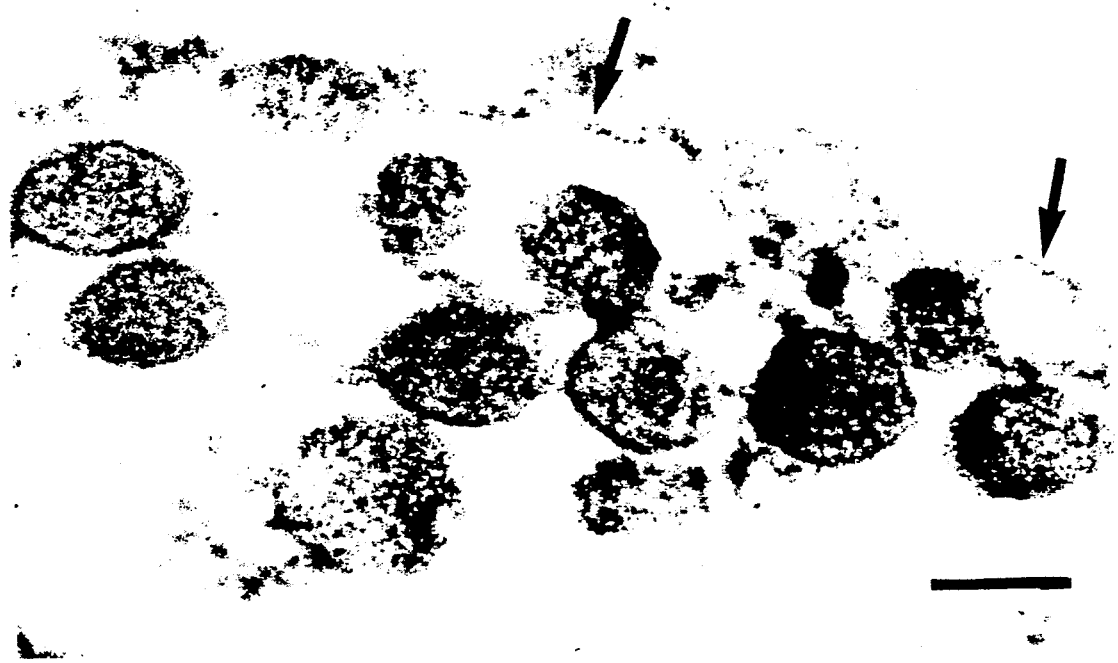
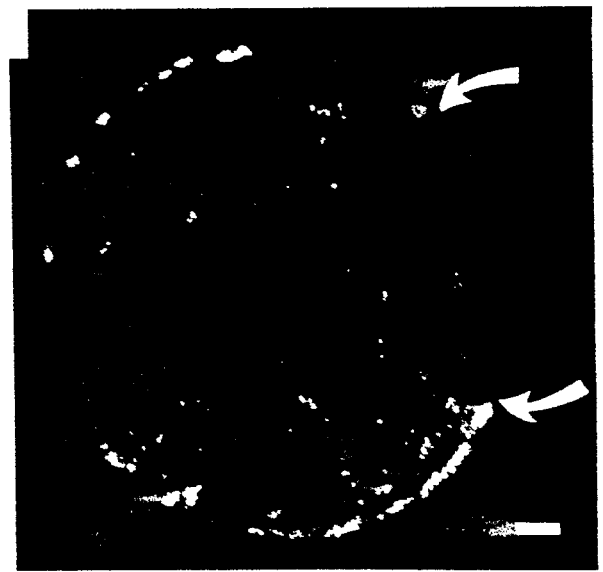
FIG. 10B                FIG. 10C

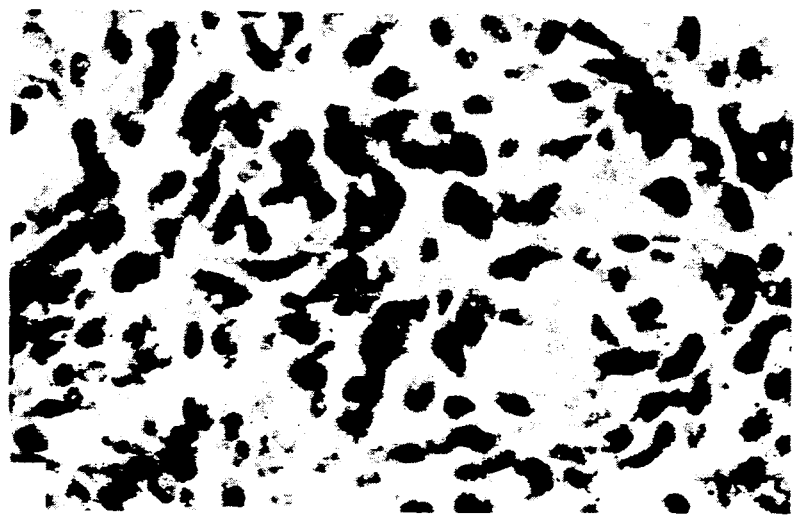
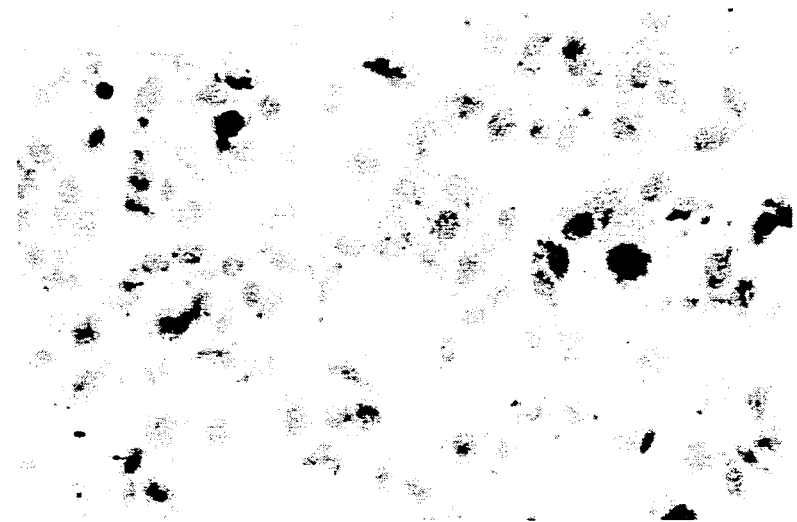

CONTROL
1-12
13-24
VLIA INFECTED
1-12
13-24

CONTROL
1-12
13-24
VLIA INFECTED
1-12
13-24

CONTROL
1-12
13-24
VLIA INFECTED
1-12
13-24

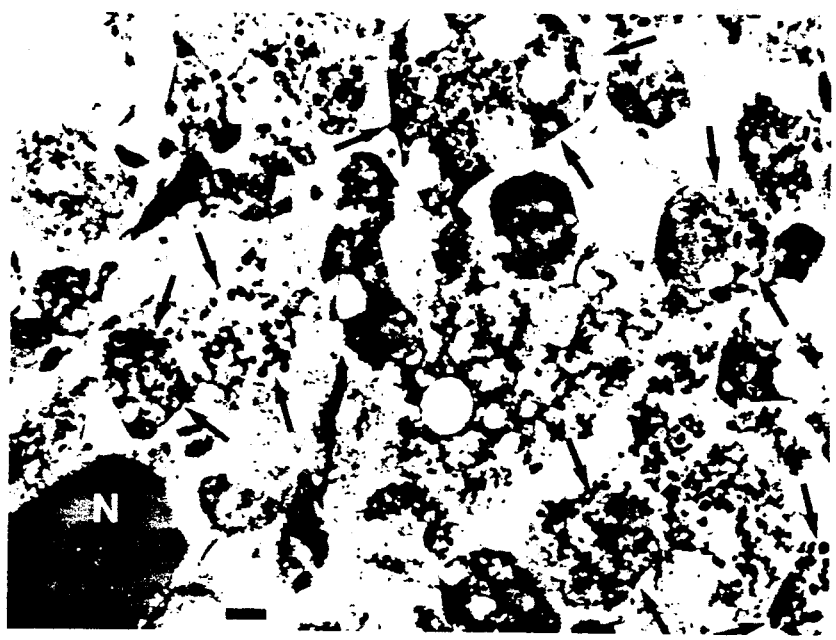
FIG. 24A₁        FIG. 24A₂
FIG. 24B₂
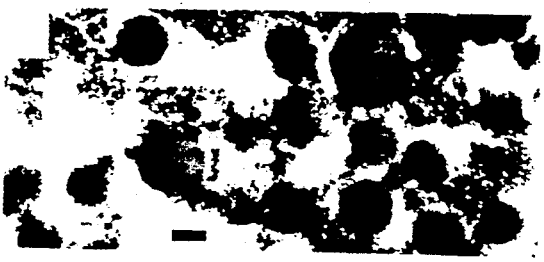
FIG. 24B₁        FIG. 24B₃

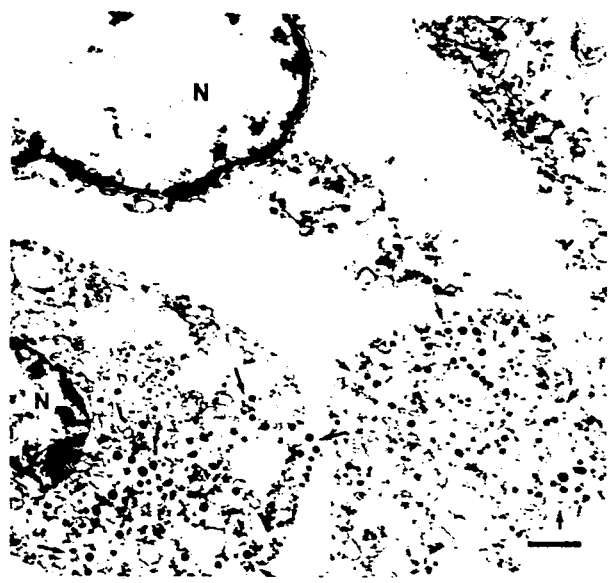
FIG. 27A  FIG. 27B
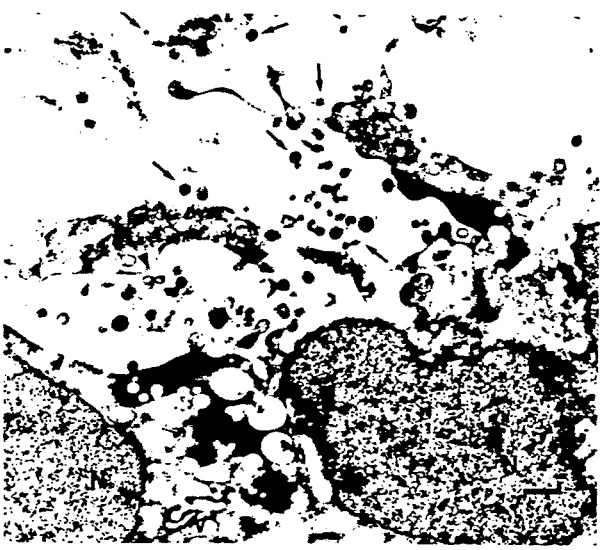
FIG. 27C  FIG. 27D

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycoplasma fermentans
        ( B ) STRAIN: incognitus ( v i i ) IMMEDIATE SOURCE:
        ( B ) CLONE: RS 48 Probe ( x i ) SEQUENCE DESCRIPTION: SEQ ID NO:1:

```
GTTAGTTTTG GCATAAATCC CC                                                    22
```

( 2 ) INFORMATION FOR SEQ ID NO:2:

( i ) SEQUENCE CHARACTERISTICS:
        ( A ) LENGTH: 2210 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycoplasmaa fermentans
        ( B ) STRAIN: incognitus ( v i i ) IMMEDIATE SOURCE:
        ( B ) CLONE: psb 2.2

( x i ) SEQUENCE DESCRIPTION: SEQ ID NO:2:

```
GAATTCTTTA ATTGAGTTGC TCATTCTTGT TTCTTGAGTT TCAGTTAGTT TTGGCATAAA      60
TCCCCCCTTG TTTTTTATAT TTAAATTATA CTTTAAAGAT TGTTAAAAAA ACAATCATAT     120
GATTGTTTTA GAGTGAACCC CAAATTCCGG ACTTTTTGGA AAGGGGTTCA TTTTTATGCA     180
ATTTAAATTT AAAAAAGTAA AAAGAAACAA ATGAAATAGA GATATAAAAG GTTATTTAAA     240
ATTAAAACTT GATCAAAAGA TAAAAATTAT CGAGTTATAT TTTCAAGAAT TTAGTATTTT     300
AGAAATATCT AAAATAATGG AAAACTCTTA TTCAGCATGC TATTCAGTAA TAGAAAAATA     360
CAAAAAGTTT GGTTATAATT CTTTTGCTAT GGAAAAGAAA AAAGGAAGAA AATCTAAAAT     420
AAATTTAGAT GCTCAAAAGG CAACAAATTT TAAAATCAAT ATTGAAAATA AAATAGAAAA     480
TAAAGATTTA TTAATTAAAC AATTAAAGGA AGAAAATAAA ATACTCAAAT TGGAGAATGC     540
GATAGCAAAA AAAGTGAGCG CCTTGGTTCA ATTGAAAGAC TCACTAACAA AGAAAAATTC     600
CAAATAACAA TTGAACTAAG GCAAGAATTT AAAAAGCTAT TTTTTATTAA ATTAATATTA     660
GAAAAAATTA AATTGAAAAA GTCAACTTTT TATGAGATAT TAAAATCACA AAATAAACCT     720
GATAAAGATG AAAATTTAAA AAAGGTTATT TTGACTTAT TTAACTATAA TAAAGGACTA      780
TACGGTTATA GACGTATTAC TTTTGCTTTA AGAAATAAAG GAATAATAAT CAATCATAAA     840
```

-continued

| | | | | | |
|---|---|---|---|---|---|
| AAAGTTCAAA | AATTAATCGA | AAGCAATGAA | TATTTTCGGC | AAAACGCTAA | GAAGAAAAAA | 900
| TAAATATTCT | TCATTCAAAG | GTGATGCTCA | CAAAACATTC | CAAACTTGCT | TTTAGATAAA | 960
| GAAATATCAC | AGAAGATTTC | TTCAGATACA | AAAGAAATTT | TTCAAATAAT | AAATATTTGA | 1020
| AAATACTAGG | AACAGATGTT | ACTGAATTTA | AATTAAAAAA | TGATGAAAAA | GCATATTTTT | 1080
| CTCCTGTAGT | TGATTTTGAA | AACAGAGAGA | TTTTAGGTTA | TTCGATTTCT | AAATCGCCTA | 1140
| ATTTAAGAAT | GGTTGGTAAA | ATGTTAGAAA | ACGTAGAAGA | GAATGGCCAC | AGCTTAAAAA | 1200
| ATGTATTATT | ACATTCTGAT | CAAGGATGAC | AATACACTCA | TCAAGATTAT | ATTGATTATT | 1260
| TGAAAGAAAA | ACAAACAACT | CAAAGCATGT | CAAGAAAGGG | AAATTGTTTA | GACAATAGTC | 1320
| CTACTGAATG | TTTATTTAGT | GTTATAAAAA | GAGAATTTTG | ATTTGGAGAA | GAAAAGAAAT | 1380
| TTAATAGTTT | TAAAGAATTT | AAAACTGCTT | TAGGAGATAT | ATTTCATATT | ATAATAATGA | 1440
| CAGAATTGTT | AATAAATTAA | AAGACTTAGT | CCTGTCCAAT | ACAGGAATAA | GTCCAAACAT | 1500
| AATTAAAAAG | TCCAATTTTT | GGGGTTCATA | CCATTTGTG | GAATTTTCT | TTTTGCCAA | 1560
| TTTTACCAA | AGCACTATAA | AACAGGCTTT | TTAGAATTTT | TCAAGCATTT | CCATTGTTT | 1620
| TTAGGATAT | TTTTTAAATC | GCAAATTTAA | CAAATTTTCT | TATAGATGCT | TCTATTTCTT | 1680
| GTTCTGATTT | TTTAAGACCT | ATTTTTTGA | TTAAACCATA | TTCAATGAAA | AATAAAATTA | 1740
| ATAAATAAAG | AGAAAGAATT | GTGAGTATTG | AAAAGACACA | AATTAAAACT | CAAAGTAAAG | 1800
| TTGTATATGT | GATTGATGGT | GCCGCTTTAT | TTTGTCAAGC | ATAAGCGATT | ACAGTTATGA | 1860
| TCAATAGAAT | TATCATAAAA | ATAAATAGGA | GTCCAAAAGC | TTTAATATTC | ATTTGATTTC | 1920
| TAAGATTTAA | ATGATCTAAA | TTGCTTTTGT | ACACTTTTTT | ATAAGCTTCT | ACTTTTTCTT | 1980
| CAAAAGAATA | TTTTTTCTTT | TGCGTTTTTT | ATTTCTTGAT | CCATAACTTT | CTCCTAATCA | 2040
| AAAGTAACAT | TCTTTAAGTT | TTTGATTCAA | TTCAATATAT | ATTTATATGT | TCGGTCAAAA | 2100
| TCTATTTTTT | TATCAACTTT | AAAGTTTTTA | TTATCAGCAA | TTTGAGCTTC | TATGTTATAA | 2160
| GCTTCAGTTT | CGCTCAAATC | ATCCTTTGAT | TCAATATCAA | TATTGAATTC | | 2210

(2) INFORMATION FOR SEQ ID NO:3:

(i) SEQUENCE CHARACTERISTICS:
        (A) LENGTH: 1405 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Mycoplasma fermentans
        (B) STRAIN: incognitus (vii) IMMEDIATE SOURCE:
        (B) CLONE: IS element (xi) SEQUENCE DESCRIPTION: SEQ ID NO:3:

| | | | | | |
|---|---|---|---|---|---|
| TAGAGTGAAC | CCCAAATTCC | GGACTTTTTG | GAAAGGGGTT | CATTTTTATG | CAATTTAAAT | 60
| TTAAAAAAGT | AAAAAGAAAC | AAATGAAATA | GAGATATAAA | AGGTTATTTA | AAATTAAAAC | 120
| TTGATCAAAA | GATAAAAATT | ATCGAGTTAT | ATTTTCAAGA | ATTTAGTATT | TTAGAAATAT | 180
| CTAAAATAAT | GGAAAACTCT | TATTCAGCAT | GCTATTCAGT | AATAGAAAAA | TACAAAAAGT | 240
| TTGGTTATAA | TTCTTTTGCT | ATGGAAAAGA | AAAAGGAAG | AAAATCTAAA | ATAAATTTAG | 300
| ATGCTCAAAA | GGCAACAAAT | TTTAAAATCA | ATATTGAAAA | TAAAATAGAA | AATAAAGATT | 360

| | | | | | | |
|---|---|---|---|---|---|---|
|TATTAATTAA|ACAATTAAAG|GAAGAAAATA|AAATACTCAA|ATTGGAGAAT|GCGATAGCAA|420|
|AAAAAGTGAG|CGCCTTGGTT|CAATTGAAAG|ACTCACTAAC|AAAGAAAAAT|TCCAAATAAC|480|
|AATTGAACTA|AGGCAAGAAT|TTAAAAAGCT|ATTTTTTATT|AAATTAATAT|TAGAAAAAAT|540|
|TAAATTGAAA|AAGTCAACTT|TTTATGAGAT|ATTAAAATCA|CAAATAAAC|CTGATAAAGA|600|
|TGAAAATTTA|AAAAAGGTTA|TTTTTGACTT|ATTTAACTAT|AATAAAGGAC|TATACGGTTA|660|
|TAGACGTATT|ACTTTGCTT|TAAGAAATAA|AGGAATAATA|ATCAATCATA|AAAAAGTTCA|720|
|AAAATTAATC|GAAAGCAATG|AATATTTCG|GCAAACGCT|AAGAAGAAAA|AATAAATATT|780|
|CTTCATTCAA|AGGTGATGCT|CACAAAACAT|TCCAAACTTG|CTTTTAGATA|AAGAAATATC|840|
|ACAGAAGATT|TCTTCAGATA|CAAAGAAAT|TTTTCAAATA|ATAAATATTT|GAAAATACTA|900|
|GGAACAGATG|TTACTGAATT|TAAATTAAAA|AATGATGAAA|AAGCATATTT|TTCTCCTGTA|960|
|GTTGATTTTG|AAAACAGAGA|GATTTTAGGT|TATTCGATTT|CTAAATCGCC|TAATTTAAGA|1020|
|ATGGTTGGTA|AAATGTTAGA|AAACGTAGAA|GAGAATGGCC|ACAGCTAAA|AAATGTATTA|1080|
|TTACATTCTG|ATCAAGGATG|ACAATACACT|CATCAAGATT|ATATTGATTA|TTTGAAAGAA|1140|
|AAACAAACAA|CTCAAAGCAT|GTCAAGAAAG|GGAAATTGTT|TAGACAATAG|TCCTACTGAA|1200|
|TGTTTATTTA|GTGTTATAAA|AAGAGAATTT|TGATTGGAG|AAGAAAAGAA|ATTTAATAGT|1260|
|TTTAAAGAAT|TTAAAACTGC|TTTAGGAGAT|ATATTTCATA|TTATAATAAT|GACAGAATTG|1320|
|TTAATAAATT|AAAAGACTTA|GTCCTGTCCA|ATACAGGAAT|AAGTCCAAAC|ATAATTAAAA|1380|
|AGTCCAATTT|TTGGGGTTCA|TACCA| | | |1405|

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycoplasma fermentans
        ( B ) STRAIN: incognitus ( v i i ) IMMEDIATE SOURCE:
        ( B ) CLONE: left inverted repeat ( x i ) SEQUENCE DESCRIPTION: SEQ ID NO:4:

TAGAGTGAAC CCCAAATTCC GGACTTTTT          29

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycoplasma fermentans
        ( B ) STRAIN: incognitus ( v i i ) IMMEDIATE SOURCE:

( B ) CLONE: right inverted repeat ( x i ) SEQUENCE DESCRIPTION: SEQ ID NO:5:

```
AAAAAGTCCA ATTTTTGGGG TTCATACCA                                          29
```

( 2 ) INFORMATION FOR SEQ ID NO:6:

( i ) SEQUENCE CHARACTERISTICS:
        ( A ) LENGTH: 429 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycoplasma fermentans
        ( B ) STRAIN: incognitus ( v i i ) IMMEDIATE SOURCE:
        ( B ) CLONE: ORF-1

( x i ) SEQUENCE DESCRIPTION: SEQ ID NO:6:

```
ATGCAATTTA AATTTAAAAA AGTAAAAAGA AACAAATGAA ATAGAGATAT AAAAGGTTAT         60
TTAAAATTAA AACTTGATCA AAAGATAAAA ATTATCGAGT TATATTTTCA AGAATTTAGT        120
ATTTTAGAAA TATCTAAAAT AATGGAAAAC TCTTATTCAG CATGCTATTC AGTAATAGAA        180
AAATACAAAA AGTTTGGTTA TAATTCTTTT GCTATGGAAA AGAAAAAAGG AAGAAAATCT        240
AAAATAAATT TAGATGCTCA AAAGGCAACA AATTTTAAAA TCAATATTGA AAATAAAATA        300
GAAAATAAAG ATTTATTAAT TAAACAATTA AAGGAAGAAA ATAAAATACT CAAATTGGAG        360
AATGCGATAG CAAAAAAAGT GAGCGCCTTG GTTCAATTGA AAGACTCACT AACAAAGAAA        420
AATTCCAAA                                                                429
```

( 2 ) INFORMATION FOR SEQ ID NO:7:

( i ) SEQUENCE CHARACTERISTICS:
        ( A ) LENGTH: 309 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycoplasma fermentans
        ( B ) STRAIN: incognitus ( v i i ) IMMEDIATE SOURCE:
        ( B ) CLONE: ORF-2

( x i ) SEQUENCE DESCRIPTION: SEQ ID NO:7:

```
ATGGTTGGTA AAATGTTAGA AAACGTAGAA GAGAATGGCC ACAGCTTAAA AAATGTATTA         60
TTACATTCTG ATCAAGGATG ACAATACACT CATCAAGATT ATATTGATTA TTTGAAAGAA        120
AAACAAACAA CTCAAAGCAT GTCAAGAAAG GGAAATTGTT TAGACAATAG TCCTACTGAA        180
TGTTTATTTA GTGTTATAAA AAGAGAATTT TGATTTGGAG AAGAAAAGAA ATTTAATAGT        240
TTTAAAGAAT TTAAAACTGC TTTAGGAGAT ATATTTCATA TTATAATAAT GACAGAATTG        300
TTAATAAAT                                                                309
```

( 2 ) INFORMATION FOR SEQ ID NO:8:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycoplasma fermentans
        ( B ) STRAIN: incognitus ( v i i ) IMMEDIATE SOURCE:
        ( B ) CLONE: ORF-3

( x i ) SEQUENCE DESCRIPTION: SEQ ID NO:8:

```
ATGAATATTA AAGCTTTTGG ACTCCTATTT ATTTTTATGA TAATTCTATT GATCATAACT      60
GTAATCGCTT ATGCTTGACA AAATAAAGCG GCACCATCAA TCACATATAC AACTTTACTT     120
TGAGTTTTAA TTTGTGTCTT TTCAATACTC ACAATTCTTT CTCTTTATTT ATTAATTTTA     180
TTTTTCATTG AATATGGTTT AATCAAAAAA ATAGGTCTTA AAAAATCAGA ACAAGAAATA     240
GAAGCATCTA TAAGAAAATT TGTTAAATTT GCGATT                               276
```

( 2 ) INFORMATION FOR SEQ ID NO:9:

( i ) SEQUENCE CHARACTERISTICS:
        ( A ) LENGTH: 143 amino acids
        ( B ) TYPE: amino acid
        ( D ) TOPOLOGY: linear ( i i ) MOLECULE TYPE: peptide ( v i ) ORIGINAL SOURCE:
        ( A ) ORGANISM: Mycoplasma fermentans
        ( B ) STRAIN: incognitus ( v i i ) IMMEDIATE SOURCE:
        ( B ) CLONE: ORF-1

( x i ) SEQUENCE DESCRIPTION: SEQ ID NO:9:

```
Met Gln Phe Lys Phe Lys Lys Val Lys Arg Asn Lys Trp Asn Arg Asp
 1               5                  10                  15
Ile Lys Gly Tyr Leu Lys Leu Lys Leu Asn Gln Lys Ile Lys Ile Ile
                20                  25                  30
Glu Leu Tyr Phe Gln Glu Phe Ser Ile Leu Glu Ile Ser Lys Ile Met
                35                  40                  45
Glu Asn Ser Tyr Ser Ala Cys Tyr Ser Val Ile Glu Lys Tyr Lys Lys
        50              55                  60
Phe Gly Tyr Asn Ser Phe Ala Met Glu Lys Lys Lys Gly Arg Lys Ser
 65                  70                  75                  80
Lys Ile Asn Leu Asp Ala Gln Lys Ala Thr Asn Phe Lys Ile Asn Ile
                85                  90                  95
Glu Asn Lys Ile Glu Asn Lys Asp Leu Leu Ile Lys Gln Leu Lys Glu
               100                 105                 110
Glu Asn Lys Ile Leu Lys Leu Glu Asn Ala Ile Ala Lys Lys Val Ser
           115                 120                 125
Ala Leu Val Gln Leu Lys Asp Ser Leu Thr Lys Lys Asn Ser Lys
           130                 135                 140
```

( 2 ) INFORMATION FOR SEQ ID NO:10:

( i ) SEQUENCE CHARACTERISTICS:
    ( A ) LENGTH: 103 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Mycoplasma fermentans
    ( B ) STRAIN: incognitus ( v i i ) IMMEDIATE SOURCE:
    ( B ) CLONE: ORF-2

( x i ) SEQUENCE DESCRIPTION: SEQ ID NO:10:

```
Met Val Gly Lys Met Leu Glu Asn Val Glu Glu Asn Gly His Ser Leu
1               5                   10                  15

Lys Asn Val Leu Leu His Ser Asp Gln Gly Trp Gln Tyr Thr His Gln
            20                  25                  30

Asp Tyr Ile Lys Tyr Leu Lys Glu Lys Gln Thr Thr Gln Ser Met Ser
            35                  40                  45

Arg Lys Gly Asn Cys Leu Asp Asn Ser Pro Thr Glu Cys Leu Phe Ser
50                  55                  60

Val Ile Lys Arg Glu Phe Trp Phe Gly Glu Glu Lys Lys Phe Asn Ser
65                  70                  75                  80

Phe Lys Glu Phe Lys Thr Ala Leu Gly Asp Ile Phe His Ile Ile Ile
            85                  90                  95

Met Thr Glu Leu Leu Ile Asn
            100
```

( 2 ) INFORMATION FOR SEQ ID NO:11:

( i ) SEQUENCE CHARACTERISTICS:
    ( A ) LENGTH: 92 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Mycoplasma fermentans
    ( B ) STRAIN: incognitus ( v i i ) IMMEDIATE SOURCE:
    ( B ) CLONE: ORF-3

( x i ) SEQUENCE DESCRIPTION: SEQ ID NO:11:

```
Met Asn Ile Lys Ala Phe Gly Leu Leu Phe Ile Phe Met Ile Ile Leu
1               5                   10                  15

Leu Ile Ile Thr Val Ile Ala Tyr Ala Trp Gln Asn Lys Ala Ala Pro
            20                  25                  30

Ser Ile Thr Tyr Thr Thr Leu Leu Trp Val Leu Ile Cys Val Phe Ser
            35                  40                  45

Ile Leu Thr Ile Leu Ser Leu Tyr Leu Leu Ile Leu Phe Phe Ile Gly
        50                  55                  60

Tyr Gly Leu Ile Lys Lys Ile Gly Leu Lys Lys Ser Gly Gln Gly Ile
65                  70                  75                  80

Gly Ala Ser Ile Arg Lys Phe Val Lys Phe Ala Ile
            85                  90
```

( 2 ) INFORMATION FOR SEQ ID NO:12:

( i ) SEQUENCE CHARACTERISTICS:
    ( A ) LENGTH: 57 amino acids
    ( B ) TYPE: amino acid
    ( D ) TOPOLOGY: linear (i i) MOLECULE TYPE: peptide (v) FRAGMENT TYPE: internal (v i) ORIGINAL SOURCE:
  (A) ORGANISM: Escherichia coli (v i i) IMMEDIATE SOURCE:
  (B) CLONE: IS3

(x i) SEQUENCE DESCRIPTION: SEQ ID NO:12:

```
Asn Val Ile Val His Thr Asp Arg Gly Gly Gln Tyr Cys Ser Ala Asp
 1               5                  10                  15
Tyr Gln Ala Gln Leu Lys Arg His Asn Leu Arg Gly Ser Met Ser Ala
                20                  25                  30
Lys Gly Cys Cys Tyr Asp Asn Ala Cys Val Glu Ser Phe Phe His Ser
            35                  40                  45
Leu Lys Val Glu Cys Ile His Gly Glu
        50                  55
```

(2) INFORMATION FOR SEQ ID NO:13:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Mycoplasma fermentans
    (B) STRAIN: incognitus (v i i) IMMEDIATE SOURCE:
    (B) CLONE: RS 47 Primer (x i) SEQUENCE DESCRIPTION: SEQ ID NO:13:

GAATTCTTTA ATTGAGTTGC TC     22

(2) INFORMATION FOR SEQ ID NO:14:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Mycoplasma fermentans
    (B) STRAIN: incognitus (v i i) IMMEDIATE SOURCE:
    (B) CLONE: RS 49 Primer (x i) SEQUENCE DESCRIPTION: SEQ ID NO:14:

TCCAAAAAGT CCGGAATTTG GGG     23

(2) INFORMATION FOR SEQ ID NO:15:

(i) SEQUENCE CHARACTERISTICS:
    (A) LENGTH: 24 base pairs ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Myccoplasma fermentans
        ( B ) STRAIN: incognitus ( v i i ) IMMEDIATE SOURCE:
        ( B ) CLONE: RW004 Primer ( x i ) SEQUENCE DESCRIPTION: SEQ ID NO:15:

GGACTATTGT CTAAACAATT TCCC        24

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycoplasma fermentans
        ( B ) STRAIN: incognitus ( v i i ) IMMEDIATE SOURCE:
        ( B ) CLONE: RW005 Primer ( x i ) SEQUENCE DESCRIPTION: SEQ ID NO:16:

GGTTATTCGA TTTCTAAATC GCCT        24

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mycoplasma fermentans
        ( B ) STRAIN: incognitus ( v i i ) IMMEDIATE SOURCE:
        ( B ) CLONE: RW006 Probe ( x i ) SEQUENCE DESCRIPTION: SEQ ID NO:17:

GCTGTGGCCA TTCTCTTCTA CGTT        24

PATHOGENIC MYCOPLASMA

The invention described herein was made in the course of work under a grant or award from the United States Department of the Army.

CROSS-REFERENCE TO RELATED APPLICATIONS

This is a continuation-in-part of U.S. patent application Ser. No. 265,920, filed Nov. 2, 1988, now abandoned, which is a continuation-in-part of U.S. patent application Ser. No. 875,535, filed Jun. 18, 1986, now abandoned.

BACKGROUND OF THE INVENTION

1. Field of the Invention

The present invention relates to a novel strain of mycoplasma isolated from a patient with AIDS. The mycoplasma is closely related to a species of human mycoplasma, *M. fermentans*. Upon characterization of this mycoplasma, it may be classified as a unique strain within the species *M. fermentans* incognitus. This novel strain of nycoplasma is referred to hereinafter as the incognitus strain or *M. fermentans* incognitus.

The invention also relates to use of the mycoplasma *M. fermentans* incognitus as well as all strains of *M. fermentans* in detecting specific antibodies in sera of patients with AIDS or an acute fulminant systemic disease and/or animals and its use as a vaccine against infection by the mycoplasma. The invention further relates to incognitus strain-specific antibodies and cross-reactive which later break up into individual cells that are capable of passing through membrane filters of pore size 0.45 $\mu$m or even 0.22 $\mu$m.

A trilaminar cytoplasmic membrane contains sterols, phospholipid and proteins. Therefore, the cells are generally susceptible to polyene antibiotics and to lysis by digitonin.

Replication of the Mycoplasma genome may precede cytoplasmic division resulting in multinucleate filaments before individual cells are delimited by constriction. Budding can also occur.

Most Mycoplasma species are facultatively anaerobic, and all known species are chemoorganotrophic. The fermentative species of Mycoplasma utilize sugars such as glucose, while non-fermentative species can utilize arginine.

Known mycoplasmas may be grown on complex media, such as Hayflick medium, while fastidious mycoplasmas may be grown on diphasic SP-4 medium. The colonies are usually of the "fried egg" type, i.e., an opaque, granular central region, embedded in the agar, surrounded by non-granular surface growth. The optimal growth temperature of mammalian strains is 36°-37° C.

Many species of Mycoplasma produce weak or clear haemolysis which appears to be due to the secretion of $H_2O_2$. This $H_2O_2$ secretion is believed to be responsible for some aspects of the mycoplasmas' pathogenicity. Known mycoplasmas are commonly sensitive to chloramphenicol and tetracyclines.

The Mycoplasma genus currently consists of more than 60 known species which are differentiated on the basis of various tests, including utilization of glucose and mannose, arginine hydrolysis, phosphatase production, the "film and spots" reaction and haemadsorption. *M. fermentans* antibodies (i.e. antibodies to homologous antigenic determinants), including monoclonal antibodies of each, which are useful in detecting incognitus strain antigens in infected tissue of patients or animals. The invention also relates to incognitus strain-specific DNA probes which are useful in detecting incognitus strain genetic materials in infected tissues of patients or animals. Incognitus strain genetic materials may also be detected in infected humans or animals by using specific incognitus strain DNA sequences a homologous *M. fermentans* DNA sequences and the polymerase chain reaction ("PCR") (U.S. Pat. No. 4,683,202 incorporated herein by reference).

The ability to monitor AIDS or other acute fulminant systemic disease status can be of great value. In addition to improving prognostication, knowledge of the disease status allows the attending physician to select the most appropriate therapy for the individual patient, e.g. highly aggressive or less aggressive therapy regimens. Because of patient distress caused by more aggressive therapy regimens, it is desirable to distinguish those patients requiring such therapies. It has been found that *M. fermentans* incognitus is more directly associated and functional deficits of the infected organ systems and is capable of distinguishing such patients.

Mycoplasma is a genus of cell wall-less sterol-requiring, catalase-negative pathogens commonly found in the respiratory and urogenital tracts of man and other animals. The cells of Mycoplasma are typically non-motile and pleomorphic, ranging from spherical, ovoid or pear-shaped to branched filamentous forms. Filaments are the typical forms in young cultures under optimal conditions, which subsequently transform into chains of coccoid cells Mycoplasmas are the smallest and simplest free-living organisms known. Mycoplasmas are not obligatory intracellular microorganisms and are usually found extracellularly, but are often found intracellularly in the infected tissues (Mycoplasma, Eds. Wolfgang, J. J., Willette, H. P., Amos, D. B., Wilfert, C. M., *Zinsser Microbiology* 19th Ed. 1988, Appleton and Lange, 617-623). The term mycoplasma apparently was first used by B. Frank in 1889 (Frank B., *Dent. Bot. Ges.*, 7, 332 (1889) and Krass, C. J. et al., *Int. J. Syst. Bacteriol.* 23, 62 (1973)). Frank, after careful microscopic observation, began writing about invasion of plants (legume) by these microorganisms and stated: "the changed character of the protoplasm in the cortical cells arising from infection, I will designate as mycoplasma". Later, he had more explicitly defined mycoplasma as a mixture of small fungus-like microorganisms and cell protoplasm (Frank, B., *Landwirt. Jahrb.* 19, 523 (1890)). The description reflected the difficulty of differentiating this unique microorganism from the infected host cells morphologically.

Even today with electron microscopy, it is still often difficult to differentiate the mycoplasmas from the cellular protoplasmic processes or the subcellular organelles of the infected host, because ultrastructurally, these microorganisms have protoplasm-like internal structures and are bounded by only an outer limited membrane (unit membrane) without a cell wall. Thus, there have been few electron microscopic studies of mycoplasmas identified directly in the infected tissues of animals or humans.

It has been reported that ultrastructural examination of infected tissues has failed to localize the microbe, even in tissues where very high titers ($>10^9$/gm) of microorganisms were recovered in culture (Elizan, T.

S. et al., *Pro. Soc. Exp. Biol. Med.* 139, 52 (1972) and Schwartz, J. et al., *Pro. Soc. Exp. Biol. Med.* 139, 56 (1972)). Therefore, morphologically, the microbe might be mimicking certain normal cellular or subcellular structures in the infected host tissues and preventing direct identification.

In addition to the natural difficulty of morphological differentiation between the microorganisms and the protoplasm of infected cells, the often poorly preserved formalin-fixed clinical materials present further limitations to any attempt to directly visualize mycoplasma organisms in the tissues.

DESCRIPTION OF THE BACKGROUND ART

Acquired Immune Deficiency Syndrome (AIDS) is a devastating disease that has afflicted over 70,000 people worldwide (AIDS Weekly Surveillance Report—United States, Centers for Disease Control, Aug. 29, 1988). The disease is clinically characterized by a set of typical syndromes which manifests itself by the development of opportunistic infections such as pneumocystic carinii pneumonia (PCP), toxoplasmosis, atypical mycobacteriosis and cytomegalovirus (CMV). Further characteristics of the AIDS associated syndromes are the clinical manifestation of neuropsychiatric abnormalities, of AIDS encephalopathy (Naura, B. A., et at., *Ann.Neuro* 19, 517 (1986)), kidney failure of AIDS nephropathy, heart failure of AIDS cardiomyopathy infections and certain uncommon malignancies such as Kaposi's sarcoma or B-cell lymphoma (Durack, D. T., *N.Eng.J.Med.* 305, 1465 (1981); Reichert, C. M., et al., *Am.J.Path.* 112, 357 (1983); Ziegler, J. L., et al., *N.Eng.J.Med.* 311, 565 (1984)).

Through co-cultivation of AIDS patients' peripheral blood cells with mitogen-stimulated normal human lymphocytes or permanent human T-cell lines, a number of laboratories have isolated T-cell-tropic human retroviruses (HTLV-III/LAV), Barre-Sinoussi, F., et al., *Science* 220, 868 (1983); Gallo, R. C., et al., *Science* 224, 500 (1984). Epidemiologically, the newly isolated retroviruses have been shown to be highly associated with patients of AIDS and/or AIDS-related complex (ARC). Schupback, J., et al., *Science* 224, 503 (1984); Sarngadharan, M. G., et al., *Science* 224, 506 (1984). In vitro studies with HTLV-III/LAV have demonstrated T-cell tropism and cytopathic changes. Barre-Sinoussi, F., et al., supra; Popovic, M., et al., *Science* 224, 497 (1984). HTLV-III/LAV is believed to be the causative agent of AIDS.

However, the establishment of an animal model of AIDS by HTLV-III-LAV injection has not been successful. Gajdusek, D.C., et al., *Lancet* I, 1415 (1984). The chimpanzee is the only primate other than man found to be susceptible to infection by HTLV-III/-LAV. However, overt AIDS manifested by the development of opportunistic infections and/or unusual malignancies has not yet been seen, despite evidence for persistent infection and/or viremia in experiments on this species. Gajdusek, D.C., et al. *Lancet* I, 55 (1985). Thus, the human retroviruses have not fulfilled Koch's postulates, i.e., producing transmissible AIDS-like diseases in experimental animals. HTLV-III/LAV is not associated with the unusual malignancies such as B-cell lymphoma and Kaposi's sarcoma, commonly found in patients with AIDS. Shaw, G. M., et al., *Science* 226: 1165–1171, 1984; Delli Bovi, P. et al., *Cancer Research*, 46: 6333–6338, 1986; Groopman, J. E., et al., *Blood* 67: 612–615, 1986. Furthermore, HIV infected patients often show a wide variation in times of disease incubation and speed of disease progression. It is not known whether any specific infectious agent other than HIV can be responsible for the complex pathogenesis often seen in this disease. One such candidate, initially identified as a virus or virus-like infectious agent in parent application Ser. No. 265,920 has now been discovered to be the mycoplasma *M. fermentans* (incognitus strain).

Although a viral etiology of developing these malignancies has long been suggested, conventional approaches for isolating infectious viral agents have not been fruitful. The presence of a transforming gene or transforming genes (oncogenes) has been associated with Kaposi's sarcoma (Lo. S., et al., *Am. J. Path.*, 118, 7 (1985)). A transformant carrying the transforming gene can cause tumors in mice. However, there is no further characterization of this transforming gene except for the presence of human repetitive DNA sequences. The transforming gene has not been shown to be associated with any viral or virus-like agent. An ongonege of AIDS Kaposi Sarcoma was similarly identified following DNA transfection into NIH/3T3 cells and was later characterized in detail (Delli Bovi O. et al., *Proc Natl Acad Sci* 84, 5660 (1987) and Delli Bovi P. et al., 50, 729 (1987). The oncogene was found to be a rearranged human protooncogene of the fibroblast growth factor (FGF) family.

SUMMARY OF INVENTION

The present invention relates to a novel strain of the mycoplasma *M. fermentans* which has been isolated from Kaposi's sarcoma of a patient with AIDS. This novel strain of mycoplasama has been designated the incognitus strain of *M. fermentans* or *M. fermentans* incognitus. The invention further relates to the use of this incognitus strain of *M. fermentans* as well as other strains of *M. fermentans* with homologous antigenic determinants for the detection of specific antibodies in sera of human patients and animals, and for vaccines against mycoplasmas. The invention also relates to antibodies, including monoclonal antibodies, to *M. fermentans* incognitus and to homologous antigenic determinants of *M. fermentans* and their use in detecting *M. fermentans* incognitus antigens in the infected tissue of human patients and animals. The invention further relates to sequencing the DNA of the *M. fermentans* incognitus and the manufacture of DNA probes based on such sequencing and homologous sequences of *M. fermentans* for use in the direct detection of the unique DNA sequences in the tissues of human patients and animals.

The present invention further relates to the detection of the presence of *M. fermentans* incognitus in patients which are HIV-positive or have other acute fulminant systemic disease as an indication of the prognosis of the disease, which can be used to determine the appropriate therapy regimen. The presence of *M. fermentans* incognitus is determined as described above.

The *M. fermentans* incognitus DNA is detected in the spleen, liver, brain, lymph nodes, kidney, placenta, lungs, adrenal glands, heart and peripheral blood mononuclear cells of patients with AIDS, or from Kaposi's sarcoma tissue from patients with AIDS. The *M. fermentans* incognitus DNA is capable of transfecting and transforming NIH/3T3 cells. *M. fermentans* incognitus is a transmissible virus-like infectious agent in cell cultures, experimental animals and humans. The DNA of the transformants does not contain human repetitive DNA sequences. Two transformants are identified as Sb51 and Kb43. These transformants are persistently infected by the *M. fermentans* incognitus. *M. fermentans* incognitus is then isolated from the transformants.

The majority of *M. fermentans* incognitus cells have a size of about 140 nm to about 280 nm, with an overall range of 100-900 nm. Introduction of *M. fermentans* incognitus into nude mice and immunocompetent mice (Balb/c) results in a significant morbidity and mortality of the infected animals and the manifestation of many symptoms such as B-cell tumor, spindle cell tumor or immunodeficiency. Similar diseases are transmitted from animal to animal by introduction of infected tissues.

*M. fermentans* incognitus was also found to infect non-human primates (monkeys). *M. fermentans* incognitus antigens were identified in the infected monkey's sera, and *M. fermentans* incognitus DNA was found in DNA isolated from tissues of the infected monkeys.

*M. fermentans* incognitus and other strains of *M. fermentans* having homologous antigens are capable of detecting antibodies in sera of patients with AIDS, ARC or non-AIDS patients with this mycoplasma infection. Any method for detecting an antigen-antibody reaction may be utilized, including enzyme-linked immunosorbent assay (ELISA), immunoradiometric assay, direct and indirect immunofluorescent assay, Western blot technique, and the like. In addition, *M. fermentans* incognitus-specific antibodies (as well as antibodies to homologous antigens of other *M. fermentans* strains) are raised in experimental animals or developed in monoclonal antibodies which are capable of detecting *M. fermentans* incognitus- related antigens in infected tissues. Furthermore, the probes having *M. fermentans* incognitus-specific or homologous *M. fermentans* DNA sequences can be used in the direct detection of *M. fermentans* incognitus DNA in infected tissues, or specific *M. fermentans* incognitus or homologous *M. fermentans* DNA sequences can be used in the polymerase chain reaction ("PCR") to identify *M. fermentans* incognitus DNA in infected tissues. Since antibodies or antisera are successfully raised against *M. fermentans* incognitus, the *M. fermentans* incognitus or homologous antigens of *M. fermentans* antigens can be utilized to prepare vaccines which may be used to protect animals, including humans, against infection by *M. fermentans* incognitus or other mycoplasmas.

BRIEF DESCRIPTION OF THE DRAWINGS

FIG. 5A shows the genetic map of a repetitive segment of a 2.2 Kb Eco RI fragment of *M. fermentans* incognitus.

FIG. 5B shows the nucleotide sequence of a repetitive segment of a 2.2 Kb Eco RI fragment of *M. fermentans* incognitus.

FIG. 10A shows an electron micrograph of thin sections of *M. fermentans* incognitus cells in the cytoplasm of degenerating Sb51 cells.

FIG. 10B shows an electron micrograph of membrane bound *M. fermentans* incognitus.

FIG. 10C shows an electron micrograph of a partially disrupted *M. fermentans* incognitus at high magnification.

FIG. 12A shows immunocytochemical staining of Sb51 cells with non-AIDS serum.

FIG. 12B shows immunocytochemical staining of NIH/3T3 cells with AIDS serum.

FIG. 12C shows immunocytochemical staining of Sb51 cells with AIDS serum.

Figures 19A, 19B, 19C, 19D, 19E, 19F, 19G, 19H:
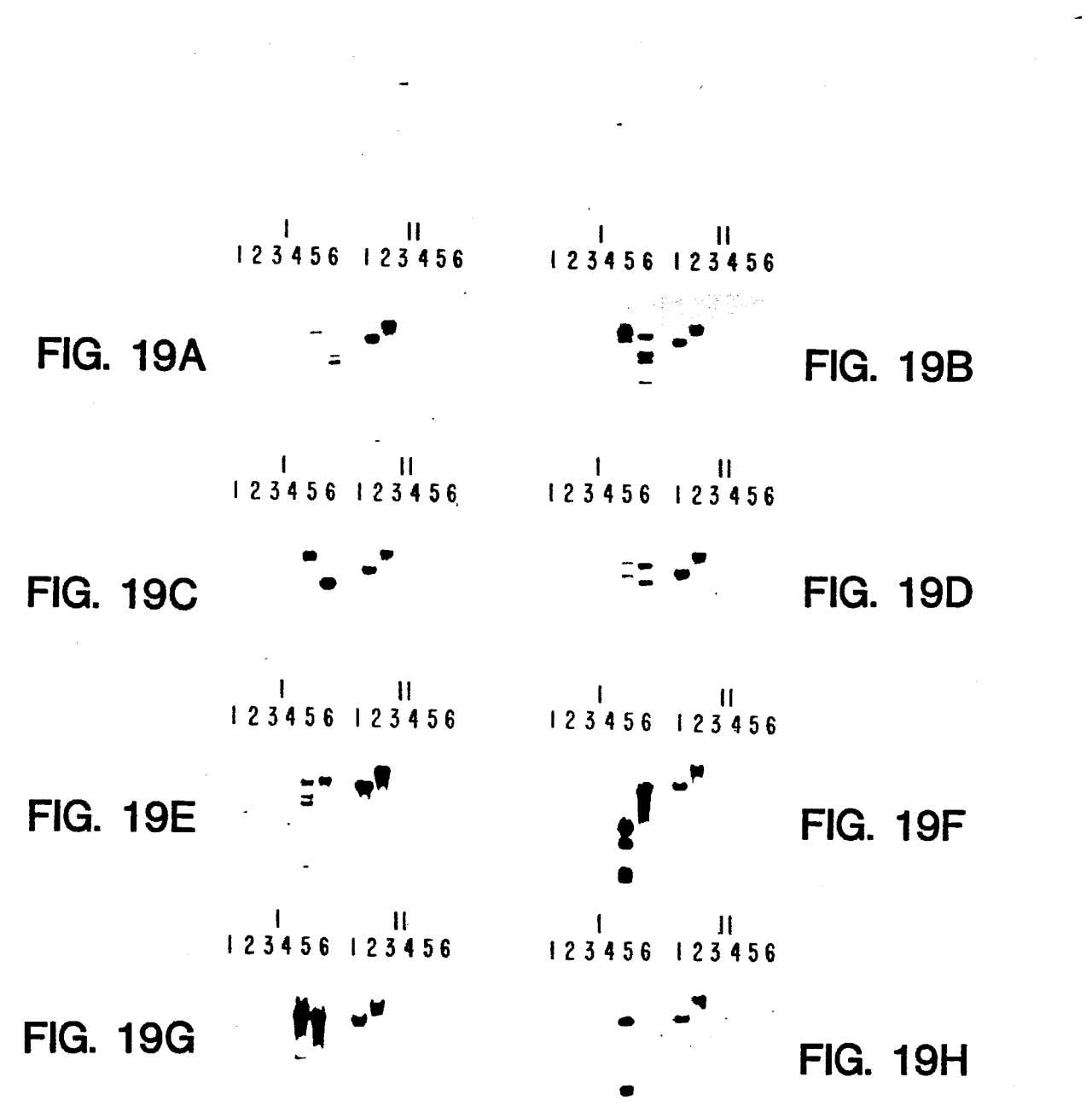

FIG. 19A shows Southern blot hybridizations to compare *M. fermentans* incognitus DNA to DNA from known human herpes viruses, vaccinia virus, MCMV and HVS. The samples were probed with A) HSV-1 pHSV-106.

FIG. 19B shows the Southern blot of FIG. 19A using B) VZV pEco A.

FIG. 19C shows the Southern blot of FIG. 19A using C) EBV pBam W.

FIG. 19D shows the Southern blot of FIG. 19A using D) CMV pCMH-35.

FIG. 19E shows the Southern blot of FIG. 19A using E) HBLV pZVH-70.

FIG. 19F shows the Southern blot of FIG. 19A using F) Vaccinia pEH-1.

FIG. 19G shows the Southern blot of FIG. 19A using G) MCMV pAMB-25.

FIG. 19H shows the Southern blot of FIG. 19A using H) HVS pT 7.4.

FIG. 24A$_1$ shows an electron micrograph of the margin of necrosis of an adrenal gland highly positive for *M. fermentans* incognitus-specific antigens.

FIG. 24A$_2$ is a higher magnification of FIG. 24A$_1$.

FIG. 24B$_1$ shows an electron photomicrograph of the peripheral zone of necrosis in lymph node highly positive for *M. fermentans* incognitus-specific antigens.

FIG. 24B$_2$ shows an electron photomicrograph of the peripheral zone of necrosis in lymph node highly positive for *M. fermentans* incognitus-specific antigens.

FIG. 24B$_3$ is higher magnification of FIG. 24B$_1$.

FIG. 27A shows an electron micrograph of an AIDS thymus immunostained positively for *M. fermentans* incognitus-specific antigens showing mononuclear lymphohistiocytes.

FIG. 27B shows an electron micrograph of an AIDS thymus immunostained positively for *M. fermentans* incognitus-specific antigens showing mononuclear lymphohistiocytes.

FIG. 27C shows an electron micrograph of an AIDS thymus immunostained positively for *M. fermentans* incognitus-specific antigens showing mycoplasma-like particles.

FIG. 27D shows an electron micrograph of an AIDS thymus immunostained positively for *M. fermentans* incognitus-specific antigens showing mycoplasma-like particles.

DETAILED DESCRIPTION OF THE INVENTION

A. Definitions

Figure 1A:
FIG. 1A shows an electron photomicrograph of *M. fermentans* incognitus.
Figure 1B:
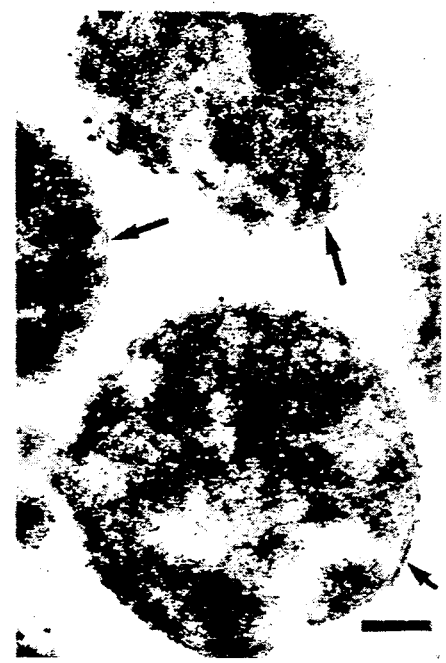
FIG. 1B shows an electron photomicrograph of *M. fermentans* prototype strain (PG18).

In order to provide a clear and consistent understanding of the specification and the claims, including the scope given to such terms, the following terms as used herein are defined below.

The term "AIDS-like syndrome" is used to describe a set of physiologic conditions or clinical presentations which are commonly used to identify individuals who are suspected of having the disease AIDS, but who have not had confirmation of the disease by blood test. The physiologic conditions are those that are common to individuals with blood test-confirmed AIDS, and include the development of opportunistic infections such as pneumocystic carinii pneumonia (PCP), atypical mycobacterial infection, toxoplasmosis and cytomegalovirus (CMV), the clinical manifestation of progressive weight loss, persistent diarrhea, neuropsychiatric abnormalities of AIDS encephalopathy, kidney failure of AIDS nepthropathy, heart failure of AIDS cardiomyopathy, respiratory distress syndrome and infections and uncommon malgnancies such as Kaposi's sarcoma or B-cell lymphoma.

The term "substantial sequence homology" is used to describe substantial functional and/or structural equivalence between sequences of nucleotides or amino acids. Functional and/or structural differences between sequences having substantial sequence homology will be de minimus.

B. Previous Related Applications

The present invention relates to a novel strain of infectious mycoplasma (*M. fermentans* incognitus) isolated from patients with AIDS. The recognition of this pathogen as a mycoplasma has been a slowly evolving process as evidenced by the history of the present specification.

The predecessor patent applications (Ser. No. 875,535, filed Jun. 18, 1986 and Ser. No. 265,920, filed Nov. 2, 1988) identified the subject pathogen as a virus and a virus-like infectious agent (VLIA), respectively. However, continuing study of the pathogen has resulted in the present identification of the pathogen as an infectious mycoplasma. Ser. Nos. 265,920 and 875,535 are incorporated herein by reference.

The presently identified mycoplasma like many other mycoplasmas has many of the characteristics of a virus, which resulted in its identification as such in the original patent application (Ser. No. 875,535, filed Jun. 18, 1986). Further research then showed characteristics which were not typical of classic viruses, thus the characterization as a VLIA in Ser. No. 265,920, filed Nov. 2, 1988. Additional research has now revealed characteristic traits of a mycoplasma as fully explained below.

C. Deposits

A mycoplasma (*M. fermentans* incognitus) according to the invention, in persistently infected cells, is deposited with the American Type Culture Collection under Deposit No. CRL 9127, deposited on Jun. 17, 1986. *M. fermentans* incognitus, itself is also deposited with the American Type Culture Collection under Deposit No. 53949, deposited on Sep. 29, 1989.

Deposit is for the purpose of completeness but is not intended to limit the scope of the present invention to the materials deposited since the description as further illustrated by the Examples fully enables the practice of the instant invention. Access to the cultures will be available during the pendency of the patent application to those determined by the Commissioner of Patents and Trademarks to be entitled thereto. All restrictions on availability of said cultures to the public will be removed irrevocably upon the grant of the instant application and said cultures will remain available permanently during the term of said patent 30 years or five years after last request, whichever is longer. Should any culture become nonviable or be destroyed, it will be replaced.

D. Physical Characteristics of M. fermentans incognitus

The M. fermentans incognitus cell is roughly spherical and about 140-200 nm in diameter, has an outer limiting membrane (about 8 nm thick), and has a buoyant density of about 1.17 g/ml to about 1.20 g/ml in a sucrose gradient. Although M. fermentans incognitus could be identified in the nuclei, mature M. fermentans incognitus cells are usually seen in the cytoplasm or associated with the plasma membrane of disrupted cytolytic cells.

Using Southern blot hybridization analysis, the M. fermentans incognitus was distinct from all known members of human herpes virus. M. fermentans incognitus was also distinct from vaccinia virus, monkey herpesvirus saimiri (HVS) and mouse cytomegalovirus (MCMV). M. fermentans incognitus can be transmitted from culture to culture by cell-free filtrate, after 0.22 micron filtration.

M. fermentans incognitus was also found to be distinct from any other known strain of Mycoplasma. One unique feature of M. fermentans incognitus is its ability to catabolize glucose both aerobically and anaerobically and also to hydrolyze arginine. M. fermentans incognitus cannot hydrolyze urea in a biochemical ssay. When grown in culture, M. fermentans incognitus produces a prominent alkaline shift in pH after an initial brief acidic shift. The only other human mycoplasma which is known to metabolize both glucose and arginine is the rarely isolated M. fermentans.

However, the incognitus strain differs from M. fermentans in that it appears to be is more fastidious in its cultivation requirements and has only been grown in a cell-free modified SP-4 medium. M. fermentans also grows in modified SP-4 medium, but at a much faster rate than M. fermentans incognitus. Furthermore, M. fermentans incognitus can be grown in a variety of commonly used mycoplasma media, whereas M. fermentans incognitus cannot.

When grown in the modified SP-4 medium, M. fermentans incognitus displays smaller spherical particle size than M. fermentans incognitus, and occasional filamentous morphology which is not seen with M. fermentans incognitus. Furthermore, M. fermentans incognitus forms only irregular and very small colonies with diffuse edges when grown on agar plates. The M. fermentans incognitus are cell wall-free and bound by a single triple layered membrane. The average size of an M. fermentans incognitus cell is about 180 nm, compared to an average size of about 460 nm for an M. fermentans cell.

FIG. 1 shows electron photomicrographs and colony morphology of M. fermentans incognitus and M. fermentans. Thin sections of concentrated M. fermentans incognitus (A) and M. fermentans incognitus (B) reveal pleophorphic microorganisms with trilaminar outer unit membrane as designated by the arrows. The bars in 1A and 1B represent 100 nm. M. fermentans incognitus (C) and M. fermentans (D) formed colonies of apparently different size and morphology after 14 days and 10 days of incubation, respectively. In these figures, the bar represents 50 μm and 20 μm, respectively.

E. Antigenic differentiation of M. fermentans incognitus and M. fermentans

Further differentiation of M. fermentans incognitus from prototype strain of M. fermentans (PG18) was displayed by antigenic analysis using both polyclonal and monoclonal antibodies, as well as DNA analysis of sequence homology and restriction enzyme mapping. These analyses showed that the incognitus strain is distinct from all other mycoplasmas, but is most closely related to previously isolated M. fermentans strains.

M. fermentans incognitus was distinguished from M. fermentans (PG18 strain) by comparing their specific antigenicity. Polyclonal rabbit antiserum (raised originally against VLIA-sb51) was found to react with both M. fermentans (PG18 strain) and M. fermentans incognitus, but not with any of the other mycoplasmas tested. However, in the same assay a larger amount of M. fermentans (PG18 strain) protein (>0.63 μg) was required to elicit a positive immunochemical response, and the positivity of the reaction rapidly disappeared when the M. fermentans (PG18 strain) protein was further diluted. In contrast, a 250-fold to 1000 fold lower concentration of M. fermentans incognitus protein still carried a sufficient amount of antigenic determinants to elicit positive reactions in the assay.

In a parallel assay, antiserum raised specifically against M. fermentans (PG18 strain) also reacted intensely with M. fermentans incognitus. The M. fermentans incognitus-specific antiserum reacted as effectively with the antigens of M. fermentans incognitus as with the antigens of M. fermentans (PG18 strain). There was approximately an equal amount of antigens which could be recognized by the M. fermentans incognitus antiserum in each unit of M. fermentans (PG18 strain) and M. fermentans incognitus proteins. Both M. fermentans and M. fermentans incognitus proteins could be diluted to 40 ng per well and still elicit a positive reaction.

However, when M. fermentans incognitus proteins and M. fermentans (PG18 strain) proteins were reacted with monoclonal antibodies raised specifically against M. fermentans incognitus, only M. fermentans incognitus proteins reacted positively. Six M. fermentans incognitus monoclonal antibodies (many with different isotypes) reacted with only M. fermentas incognitus, but not with M. fermentans. Therefore, M. fermentans incognitus carries additional specific antigens which can not be identified in the prototype of M. fermentans (PG18 strain).

FIG. 2 shows antigenic comparison of M. fermentans incognitus, M. fermentans and other human mycoplasmas in immunoblots. Upper blot (2A) was immunostained with rabbit antiserum raised specifically against M. fermentans incognitus. Lower blot (2B) was immunostained with mule antiserum raised specifically against M. fermentans (PG18 strain). The concentration of mycoplasma protein was dot-blotted decrementally (1:4 dilution) from lane 1 (10 μg) to lane 12 (2.5 pg). Row A (M. arginini), row B (A. laidlawii), row C (M. fermentans), row D (M. hominis), row E (M. orale), row F (M. hyorhinis), row G (M. pneumonia), row H (M.

*fermentans* incognitus). In FIG. 2C row A, B, C, D and F were immunostained with monoclonal antibodies D81E7, C69H3, F89H7, B109H8, F11C6 and C42H10, respectively. The concentration of mycoplasma protein was dot-blotted decrementally (1:10 dilution) from lane 1 (10 μg) to lane 8 (1 pg). Row a (*M. fermentans* incognitus) and Row b (*M. fermentans*).

F. DNA Homology

DNA was isolated from *M. fermentans* incognitus and ten other species of mycoplasmas (*M. orale*), *M. hyorhinis, M. pneumonia, M. arginini, M. hominis, M. fermentans, M. genitalium, M. salivarium, U. urealyticum* and *A. laidlawii*) and analyzed on Southern blots, being probed with $^{32}$P-labeled cloned *M. fermentans* incognitus DNA (psb-8.6, psb 2.2) or synthetic oligonucleotide RS48 (SEQ ID NO:1) a *M. fermentans* incognitus-specific sequence. An additional molecular clone, carrying a 3.3 kilobase insert of *M. fermentans* incognitus DNA (MI-H 3.3) was also used as a probe.

Although some homology with psb-2.2 was observed in the *M. orale* genome, no homology with RS48 (the specific DNA sequences occurring at one terminal end of psb-2.2) and no homology with psb-8.6 or MI-H 3.3 were identified in the *M. orale* genome. Although DNA homology with psb-8.6, psb-2.2, RS48 and MI-H 3.3 were all found in the *M. fermentans* (PG18 strain) genome, the restriction patterns revealed by these probes were different between *M. fermentans* (PG18 strain) and *M. fermentans* incognitus.

FIG. 3 shows a comparison of DNA homology and restriction patterns between *M. fermentans* incognitus and other human mycoplasmas. The blots were probed with $^{32}$P nick-translated psb-8.6 (3A) and psb-2.2 (3B), $^{32}$P end-labeled RS48 (3C), $^{32}$P labeled MI-H 3.3 (3D) and $^{32}$P end-labeled cDNA probe of *E. coli* ribosomal RNA (3E). Each lane contained 0.2 microgram of EcoRI enzyme pre-digested DNA from *Acholeplasm laidlawii* (lane 1), *M. arginini* (lane 2), *M. hominis* (lane 3), *M. hyorhinis* (lane 4), *M. pneumoniae* (lane 5), *M. orale* (lane 6), *M. fermentans* (PG18 strain) (lane 7) and *M. fermentans* incognitus (lane 8). Arrows indicate the positions of standard size marker 23, 9.4, 6.7, 4.4, 2.3, and 2.0 kb, respectively.

Furthermore, there is significant homology between the ribosomal RNA (r-RNA) genes of procaryotive mycoplasmas and those of *Escherichia coli* bacterium. The same blot which was consecutively probed with RS48 and MI-H 33 was reprobed with $^{32}$P-labeled cDNA of *E. coli* or r-RNA, after removing the previously incorporated probe by boiling the filter. The analysis of r-RNA genes revealed both a difference in numbers and size of the hybridization bands with each different species of mycoplasma tested. The EcoRI restriction pattern of the r-RNA genes for *M. fermentans* incognitus and *M. fermentans* (PG18 strain) appeared to be identical, but were different from any other mycoplasma tested.

G. Immunofluorescence Staining

Figure 4A:
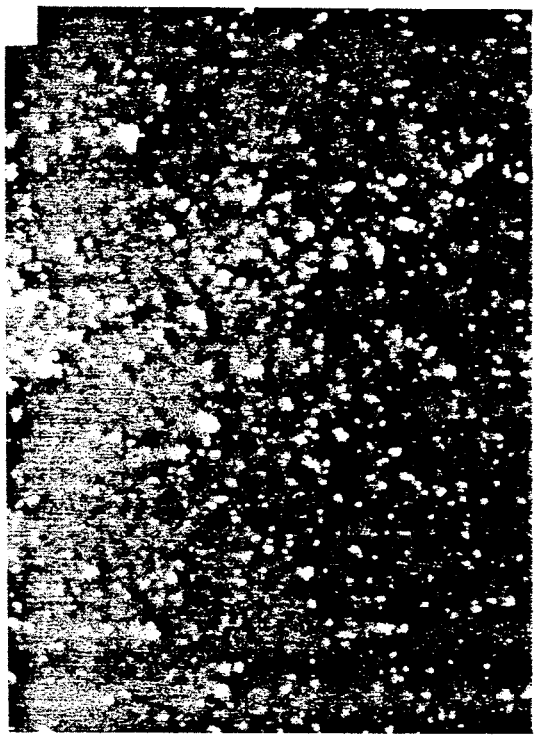
FIG. 4A shows direct immunofluorescence staining of *M. fermentans* incognitus using FITC conjugated monoclonal antibody D81E7 (X900).
Figure 4B:
FIG. 4B shows direct immunofluorescence staining of *M. fermentans* using FITC conjugated monoclonal antibody D81E7 (X900).

Further support for the conclusion that *M. fermentans* incognitus differs from any other mycoplasma came from a study of direct immunofluorescence staining. An FITC probe was conjugated to the purified *M. fermentans* incognitus monoclonal antibodies, and again revealed positive staining only in *M. fermentans* incognitus, but not in *M. fermentans* (PG18 strain) or six other species of human mycoplasmas. FIG. 4 shows direct immunofluorescence straining of *M. fermentans* incognitus (A) and *M. fermentans* (PG18 strain) (B) using FITC conjugated monoclonal antibody D81E7 (X900).

H. *M. fermentans* incognitus Infection

A high prevalence of *M. fermentans* incognitus infection has been found in patients with AIDS by using the polymerase chain reaction. The genetic material specific for *M. fermentans* incognitus has been isolated from spleens, Kaposi's sarcoma, livers, lymph nodes, peripheral blood mononuclear cells and brains of patients with AIDS.

Furthermore, *M. fermentans* incognitus infection has been found in previously healthy non-AIDS subjects with an acute fatal disease. The *M. fermentans* incognitus infection in these patients was directly identified in the necrotizing lesions in lymph nodes, spleens, livers, adrenal glands, heart and brain.

The pathogensis of *M. fermentans* incognitus infection is unusual in that despite fulminant tissue necrosis, there is lymphocyte depletion and an apparent lack of cellular immune response or inflammatory reaction in the infected tissues. It is believed that infection of *M. fermentans* incognitus either has concomittantly caused damage to key components of the hosts' immune system, or this pathogen has special biological properties which enable it to elude immunosurveillance of the infected hosts.

Coinfection with *Mycoplasma fermentans* (incognitus strain) enhances the ability of human immunodeficiency virus type-1 (HIV-1) to induce cytopathic effects on human T lymphocytes in vitro. Syncytium formation of HIV-infected T cells was essentially eliminated in the presence of *M. fermentans* (incognitus strain), despite prominent cell death. However, replication and production of HIV-1 particles continued during the coinfection. Furthermore, the supernatant from cultures coinfected with HIV-1 and mycoplasma may be involved in the pathogenesis of acquired immunodeficiency syndrome (AIDS). Abstract from *Science* 251, 1074 (1991). Since the presence of *M. fermentans* incognitus is most often associated with AIDS and other acute fulminant disease states and more profoundly affects the course of its disease, it can be used to determine the prognosis of these diseases, which information can be utilized for designing therapy regimes. Without being bound by any proposed mechanism, it is believed that antibodies against ORF-1 (see below) may react against CD4+ lymphocytes resulting in an auto-antibody response against CD4 on T cells thus enhancing the cytopathic effects of HIV-1 on T cells.

I. DNA Characteristics of *M. fermentans* incognitus

*M. fermentans* incognitus was originally isolated from Kaposi sarcoma tissue of an AIDS patient. The DNA genome of the *M. fermentans* incognitus is greater than 150 kilobase (kb) pairs and carries repetitive sequences. An 8.6 kb pair cloned probe (psb-8.6) and a 2.2 kb pair cloned probe (psb-2.2) of *M. fermentans* incognitus detected specific sequences of DNA in Sb51 cells and *M. fermentans* incognitus infected cells, but not in DNA of uninfected NIH/3T3 cells.

The cloned probes (psb-8.6 and psb-2.2) can be obtained from an EcoRI partial digest of *M. fermentans* incognitus enriched DNA which is cloned into bacteriophage lambda charon 28. The lambda-recombinant clones are screened by differential plaque hybridization with $^{32}$P-labeled DNA derived from gradient banded

*M. fermentans* incognitus. The insert of the phage clone is then recloned into the EcoRI site of Bluescript KS (M 13−) vector (Stratogene) to produce the cloned probes, psb-8.6 and psb-2.2.

By nucleic acid analysis, the *M. fermentans* incognitus has been compared with large DNA viruses of the herpes group such as herpes simplex virus type I and II (HSV-I and II), human cytomegalovirus (CMV), Epstein-Barr virus (EBV), Varicella-Zoster virus (VZV) and human B-lymphocytic virus (HBLV) or human herpesvirus-6 (HHV-6), vaccinia virus, Herpesvirus saimiri (HVS) of monkeys and mouse cytomegalovirus (MCMV). Part of the *M. fermentans* incognitus genomic DNA has been molecularly cloned. The entire sequence of a cloned *M. fermentans* incognitus psb-2.2 DNA has been obtained and is shown as SEQ ID NO:2.

To obtain the genetic materials of *M. fermentans* incognitus, the Kaposi's sarcoma tissue is minced into small pieces and treated with collagenase. The tissue suspension is then treated with a proteinase, such as proteinase K. Genetic materials are obtained after phenol extraction, phenol/chloroform/ isoamylalcohol extraction, and chloroform/isoamylalcohol extraction. High molecular weight DNA is visibly observed after ethanol precipitation of the genetic materials. The genetic materials are dissolved and contain high molecular weight DNA and RNA of various sizes.

The isolated genetic materials from Kaposi's sarcoma are utilized to transfect NIH/3T3 cells or other proper recipient cells in accordance with the procedure of Graham, F. L., et al., Virology 52, 456 (1973). In this procedure, the nucleic acid is precipitated with calcium phosphate and incubated with NIH/3T3 cells. The precipitated nucleic acid is removed and the cells trypsinized. The trypsinized cells are reseeded and treated with glycerol before splitting, as described by Copeland, N. G., et al., *Cell* 16, 347 (1979). The subcultures are fed with Dulbecco's medium with fetal bovine serum (FBS) and re-fed at three- to four-day intervals.

Foci of morphologically transformed cells become evident in about two weeks. The phenotypical transformation is characterized by rapid overgrowth of the transfected cells which pile up in multilayers and form grossly visible foci. Transformation efficiency is about 0.01–0.02 identifiable foci per microgram of donor nucleic acid. Transformed colonies are harvested after three weeks, and are cultured in monolayers. The DNA of transformants contain human repetitive DNA sequences.

Genetic materials are isolated from the primary transfectants as previously described, and used to transfect fresh NIH/3T3 cells. Transformation is again seen using the genetic materials with a slightly higher transformation efficiency. This demonstrates that the genetic materials isolated from tissues of AIDS patients contain active transforming elements. This is the first description ever of mycoplasmal DNA transfecting cells.

The nucleotide sequence of the *M. fermentans* incognitus EcoRI 2.2 kb DNA (plasmid psb 2.2) is shown in SEQ ID NO:2. This plasmid has a segment of unique sequences which occurs repeatedly in the *M. fermentans* incognitus genome.

By sequence analysis, a genetic element of 1405 base pairs (SEQ ID NO:3) with unique structural characteristics was identified. These unique structural characteristics strongly resemble bacterial insertion sequence (IS) elements. The IS-like element occurs repeatedly in the *M. fermentans* incognitus genome.

In analyzing the *M. fermentans* incognitus EcoRI 2.2 kb DNA, one pair of inverted repeats (IR) consisting of 29 bp with seven mismatches was found. These IR are SEQ ID NO:4 (left IR) and SEQ ID NO:5 (right IR). Immediately outside and flanking these 29-bp IR is a 3-bp direct repeat (DR), TTT. The element framed by these two 29-bp IR contains 1405 bp (SEQ ID NO:3). Many pairs of IR that have eight or more contiguous nucleotides are also found within this 1405-bp element. There are two potential stem-and-loop (s&l) structures, L and R, in the element (see FIG. 5) (SEQ ID NO:3). L($\Delta G = -16.8$ kcal/mol) is located exactly at the left terminus of the element, while R ($\Delta G = -14.4$ kcal/mol) is located very near the right terminus. Both of the potential s&l structures are followed by a stretch of T residues pointing toward the interior of the element. These s&l structures with T resides strongly resemble transcription terminators (Rosenberg and Court, *Annu. Rev. Genet.*, 13 319 (1979), which would prevent transcription from the outside into the element (Syvanen, *Annu. Rev. Genet.*, 18 271 (1984)). The structures may also be responsible for the strong polarity of this element (Grindley and Reed, *Annu. Rev. Biochem.*, 54 863 (1985)). Similar transcription terminators have been found at the termini of several bacterial IS elements. These unique structures are probably maintained for specific benefit of the IS elements and play an important role in the regulation of transposition.

Mycoplasma DNAs are extremely rich in A and T. It has already been shown in the codon usage of ribosomal protein genes of *M. capricolum* that synonymous nucleotide substitution and conservative amino acid substitution can occur (Muto et al., *Nucleic Acids Res.*, 12 8209 (1984)). It has also been reported that TGA, instead of being a stop codon, is a Trp codon in many species of mycoplasma (Yamao et al., *Proc. Natl. Acad. Sci. USA*, 82 2306 (1985)); Inamine et al., *J. Bacteriol.*, 172 504 (1990)). According to this unique character of codon usages in mycoplasma, three potential ORFs, ORF-1, ORF-2, and ORF-3 (SEQ ID NO:6, 7 and 8, respectively) have been identified in the 2.2-kb DNA. ORF-1 and ORF-2 are located inside the element and ORF-3 is located on the complementary strand 100-bp away from the element.

ORF-1 (SEQ ID NO:6) begins immediately after the s&l structure L at nucleotide 176 and ends at nucleotide 604, and could encode a protein of 143 amino acids (SEQ ID NO:9). There is a possible Shine Delgarno (SD) sequence, AAGGGG (nucleotides 161–166), which precedes the start codon of ORF-1 by 9-bp, and is located inside the s&l structure L (FIG. 5, SEQ ID NO:2 and 3, respectively). There is no consensus sequence for the −10 and −35 promoter regions, however, the left IR may provide a promoter function which has been previously shown in the *E. coli* IS1 element (Machida et al., *J. Mol. Biol.*, 177 229 (1984)).

ORF-2 (SEQ ID NO:7) begins at nucleotide 1149 and ends at nucleotide 1457, immediately in front of the s&l structure R, and could encode a protein of 103 amino acids (SEQ ID NO:10). There is a promoter-like region which has a −35 region (TTGATT) at nucleotides 1090–1095 and a −10 region (TAGGTT) at nucleotides 1114–1119 located upstream from ORF-2 (FIG. 5, SEQ ID NO:2 and 3, respectively). ORF-3 (SEQ ID NO:8), between nucleotide 1912 and 1637 (on the complementary strand), could encode a 92-amino acids protein (SEQ ID NO:11) (FIG. 5, SEQ ID NO:2 and 3, respectively).

A computer search of the National Biomedical Research Foundation (NBRF) Protein Data Bank has revealed a 40% homology (49% with conservative replacements) between a region of the deduced amino acid sequence of ORF-1 (SEQ ID NO:9; amino acid 101-140) and *Streptococcus pyogenes* Pep M5 protein (amino acids 23-65). The biological function of antiphagocytosis in this pathogenic bacteria is known to be associated with Pep M5 protein (Fox, *Bacteriol. Rev.*, 38 57 (1974)). The search also revealed that 75% of the amino acids are identical between a region of the deduced amino acid sequence of ORF-1 (SEQ ID NO:9, amino acid 117-128) and the sequence in the extracelluar V4 domain of human T-cell surface glycoprotein CD4 molecule (amino acid 319-329). Another extracellular domain (V1) of the same CD4 molecule is critical for recognition by HIV envelope glycoprotein (Arthos et al., *Cell*, 57 469 (1989)). The significance of the homologies of ORF-1 with Pep M5 protein and the CD4 molecule on human T cells is not clear at this time, but this 75% homology between the amino acid sequence of ORF-1 and CD4 is enough difference to result in the production of antibody to the ORF-1 antigen. However, this antibody may then attack both the ORF-1 antigen and the CD4 receptors due to their similarity.

In a similar analysis, a 43% homology (55% with conservative replacements) between a region of the deduced amino acid sequence of ORF-2 (SEQ ID NO:10, amino acid 18-74) and the deduced amino acid sequence of the putative transposase of *E. coli* IS3 (SEQ ID NO:12, amino acid 189-245) was found. In addition, the ratio of basic to acidic amino acid in protein predicted by ORF-2 is around 2. Thus, this basic protein encoded by ORF-2 highly resembles the *E. coli* putative transposase which is believed to be essential for transpositional recombination (Grindley and Reed, *Annu. Rev. Biochem.*, 54 863 (1985)). No significant homology was found between ORF-3 and sequences in the NBRF Protein Data Bank. Also there is no significant homology between the nucleotide sequence of 2.2-kb DNA (SEQ ID NO:2) and the nucleotide sequences in the GenBank database.

Figure 5C:
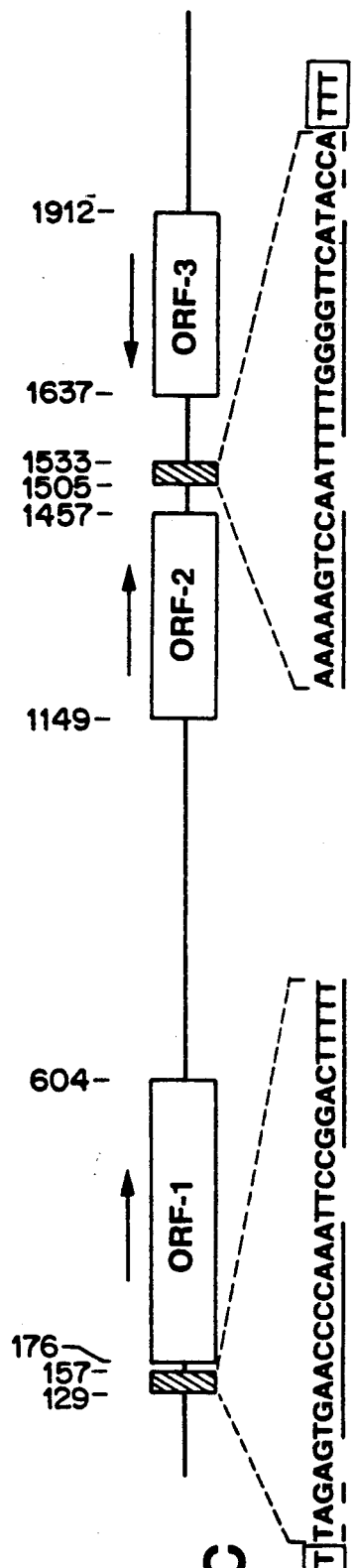
FIG. 5C shows the genetic map of a repetitive segment of a 2.2 Kb Eco RI fragment of *M. fermentans* incognitus.

It has been shown that this cloned DNA (psb-2.2; ID SEQ NO:2) contains a unique sequence which occurs more than ten times in the genome of *M. fermentans* incognitus (Lo et al., Am. J. Trop. Med. Hyg., 40 213 (1989)) (also FIG. 6). To precisely define the boundary of this repetitive element, a series of ten oligos, B through K, were synthesized and used as probes. Each probe contained 20-24 nucleotides of a specific sequence from a selected segment in 2.2-kb DNA (FIG. 5). The nt positions of the synthetic oligo, B through K, used as serial probes to identify the boundary of the IS-like repetitive element in the *M. fermentans* incognitus genome (see FIG. 4) as follows: B (1659-1678), C (1531-1550), D (1514-1533), E (1454-1477), F (1228-1247), G (681-700), H (328-347), I (129-148), J (115-135), and K (44-65) of SEQ ID NO:2. Among the ten oligos, D to I are a series of representative sequences within the 1405-bp IS-like element, and I and D represent sequences within the left and right terminal IR, respectively. B, C, J, and K represent sequences outside the element. Both J and C represent the sequence of the junction areas of the element and actually carry a part of the sequence of the left and right IR, respectively. Each of these synthetic oligo probes was end-labeled with $^{32}$P and used individually to probe *M. fermentans* incognitus genomic DNA predigested with either EcoRI or HindIII.

The hybridization patterns of multiple bands produced by probes D to I, which carry representative sequences of the various segments in the IS-like element, were essentially the same. In EcoRI digestion, there are eleven identical bands with sizes ranging from 2.20 to 8.90 kb (FIG. 6, D-I, lanes b). When using HindIII digestion, there are twelve identical bands with sizes ranging from 1.95 to 9.10 kb (FIG. 6, D-I, lanes a, b). This pattern of multiple hybridization bands matches exactly with that produced when psb-2.2 DNA is nick-translated and used as a probe (FIG. 6A).

Figures 6A, 6B, 6C, 6D, 6E, 6F:
FIG. 6 shows the analysis of repetitive elements following probing with A) psb-2.2 and B-K of FIG. 5A.
Figures 6G, 6H, 6I, 6J, 6K:
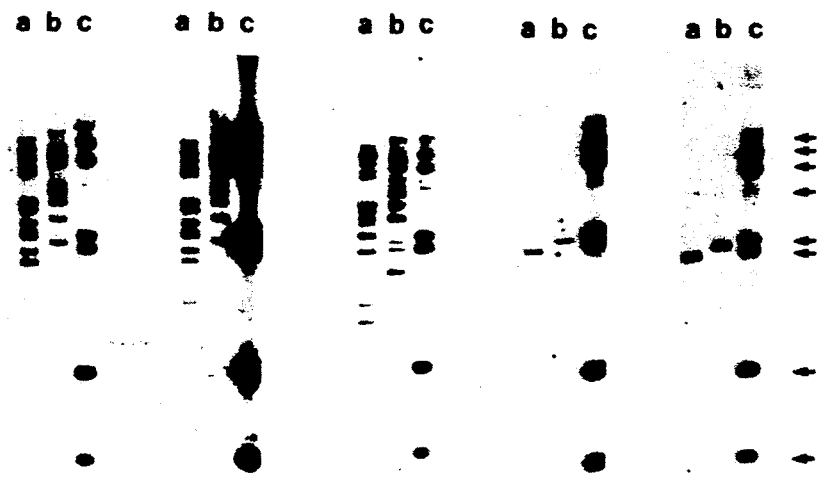

In contrast, the probes B, C, J and K produced a completely different pattern with only a single hybridization band of 2.2-kb in EcoRI digestion or a 1.95-kb fragment in HindIII digestion (FIG. 6B, C, J and K). Probes I (20-mer) and J (21-mer) overlap 7 nucleotides within the left IR; the former produced the typical pattern of multiple bands (FIG. 6I), however, the latter only produced a single band (FIG. 6J).

It was also noted that probes D(20-mer) and C(20-mer) overlap by 3 nucleotides within the right IR; the former produced the typical pattern of multiple bands (FIG. 6D), however, the latter only produced a single band (FIG. 6C). Thus, the 1405-bp IS-like element (SEQ ID NO:3) which is located between nucleotides 129 and 1533, is the repetitive element which occurs more than ten times in the genome of *M. fermentans* incognitus. This finding suggests that the IS-like element is a mobile element. Such mobility suggests the use of this IS-like element as a means for inserting other sequences into other cells (i.e. the IS-like-element can be used as a cloning vector). The presence of mulitiple gene copies may result from transposition.

The evidence which supports the conclusion that the 1405-bp element is an IS-like element is: (1) the size of the element (1405-bp) being in the range of previously identified bacterial IS elements (800-2500 bp); (2) the presence of 29-bp IR, with seven mismatches located at both of the termini of the element; (3) the presence of a 3-bp DR immediately flanking outside both of the terminal IR; (4) two ORFs (ORF-1 and ORF-2) which could potentially encode two basic proteins; part of the deduced amino acid sequence of ORF-2 being homologous to part of the putative transposase of IS3, and (5) the presence of multiple copies in the genome of *M. fermentans* incognitus. Several other unique structural features found in the 1405-bp element which are also present in bacterial IS elements are: (i) the s&1 structure located close to at least one terminus; (ii) the presence of a large number of sequences with properties of IR, and (iii) part (9 bp) of the sequence in one of the terminal IR found again as a repeat sequence (either direct or indirect) near the other terminal IR (see SEQ ID NO:2 & 3).

J. Detection of *M. fermentans* incognitus DNA by PCR

A polymerase chain reaction (PCR) assay to detect *M. fermentans* was designed on the basis of specific nucleotide (nt) sequences found at one terminus of the cloned incognitus strain of *M. fermentans* DNA psb-2.2 (SEQ ID NO:2). Primers (RS47 (SEQ ID NO:13) and RS49 (SEQ ID NO:14)) were chosen to produce an amplified DNA fragment of 160 bp. (See Examples 16 and 19.) The PCR assay detected very specifically the mycoplasmas of *M. fermentans* species but not other human or non-human mycoplasmas, bacteria or eucaryotic cell DNA that we tested. However, this highly specific assay using these primers failed to detect some mycoplasmas of the *M. fermentans* species. Ten fg of DNA consistently yielded a positive 160 bp amplified band in DNA isolated from the incognitus strain of *M. fermentans*, from a strain (k7) previously islated from the bone marrow of a patient with leukemia/lymphoma and from other *M. fermentans* strains (MT-2) isolated from contaminated human lymphocyte cultures. A thousand fold higher amount of DNA (10 pg) isolated from the prototype strain of *M. fermentans* (PG-18, and ATCC #19989) as well as DNA from two recent clinical isolates from patients with AIDS tested negative for the diagnostic DNA fragments. Thus, the specific gene arrangement used in this PCR assay was apparently not universally present in the DNA of all *M. fermentans* species.

A more sensitive PCR assay which is able to detect all the different strains or clinical isolates of *M. fermentans*, yet remains highly selective or specific, was then developed based on the presence of multiple copies of an insertion sequence-like (IS-like) genetic element in *M. fermentans*. The actual copy number of the IS-like element found in the genomes of different strains or isolates of *M. fermentans* may vary and range from 5 to more than 10 copies. A new set of primers (RW004 (SEQ ID NO:15) and RW005 (SEQ ID NO:16)) used to produce an amplified fragment of 206 bp in our new PCR assay.

Using the new set of primers and RW006 (SEQ ID NO:17) as a probe, the reaction consistently detected 1 fg of DNA in all *M. fermentans* species tested (FIG. 7) including the prototype strain PG-18 and new clinical isolates from patients with AIDS, whose DNA (up to 10-pg) tested negative in the PCR reaction using the old set of primers. Sensitivity of this newly developed PCR assay was further verified by successfully detecting 1 fg of the *M. fermentans* DNA in the presence of 1 ug of non-specific human background DNA. Specificity of the reaction has also been examined by attempting to amply the DNAs isolated from other human or non-human mycoplasmas, common tissue culture contaminating mycoplasmas, Gram-positive or Gram-negative bacteria, mouse, monkey and human cell culture and/or tissue. The reaction does not produce the specific 206 bp DNA fragment.

The present study shows that we have developed a highly selective assay to detect *M. fermentans* by PCR with remarkable sensitivity. The assay detects all the different strains and the new clinical isolates of *M. fermentans* that the previous PCR assay using primers RS47 and RS49 failed to detect and appears to be 10 times more sensitive. The limitation of reaction sensitivity per assay for our current PCR is 0.1 to 1 fg *M. fermentans* DNA within a background of 1 ug of human DNA instead of 1 to 10 fg of microbe DNA in our previous PCR assay. Thus, a molecular technique selectively detecting a single microorganism of *M. fermentans* is available.

K. Infection and Transfection with *M. fermentans* incognitus

*M. fermentans* incognitus is isolated from the transformants, such as Sb51. In general, Sb51 cell pellets are lysed by freezing and thawing to release *M. fermentans* incognitus particles. The large *M. fermentans* incognitus particles are pelleted through a sucrose barrier and banded in a sucrose isopycnic gradient. The intact *M. fermentans* incognitus particles have a density of about 1.17 to about 1.20.

*M. fermentans* incognitus can be introduced into mice. In general, the *M. fermentans* incognitus isolated from $5\times10^6$ Sb51 cells is injected either intravenously or intraperitoneally into six-week-old mice. Nude mice or immunocompetent mice can be infected. Infection of nude mice with *M. fermentans* incognitus results in significant mortality of the infected animals. Many symptoms similarly seen in patients with AIDS are induced by the infected mice. Thus, at necropsy, the infected mice often showed prominent systemic lymphadenopathy, neuropathy or lymphoid depletion with varying degrees of plasmacytosis. Signs of immune deficiency with profound cutaneous infection in some of the animals were noted. Disseminated pruritic skin rashes were also common. There were proliferative lesions of spindle cells in the cutaneous tissue and deep viscera. The immunocompetent mice (Balb/c) infected by *M. fermentans* incognitus were found to be subsequently infected by *Pneumocystis carinii*, which is evidence of the immunnodeficient state of these infected animals.

Similar diseases are transmitted from animal to animal by injecting filtrated lysates of spleen, lymph nodes or whole blood from the diseased animals. *M. fermentans* incognitus is also identified in the cytoplasm of the cytopathic cells. Some of the infected mice were found to produce prominent antibody against *M. fermentans* incognitus.

When silver leaf monkeys are inoculated with *M. fermentans* incognitus, the monkeys show wasting syndromes and die within seven to nine months after inoculation. At necropsy, the monkeys do not show evidence of opportunistic infections, acute inflammatory lesions or malignancy. *M. fermentans* incognitus-specific DNA can be directly detected in necropsy tissues of the monkeys, by use of polymerase chain reaction method. *M. fermentans* incognitus infection can be identified in spleen tissue, liver tissue, kidney tissue and brain tissue of the monkeys. Some of the infected monkeys produced antibody to *M. fermentans* incognitus.

L. Detection of *M. fermentans* incognitus Antigens

The *M. fermentans* incognitus pathogen is useful for the detection of antibodies in the sera of patients or animals infected with *M. fermentans* incognitus. Some of these patients who are infected with *M. fermentans* incognitus will be patients who have been diagnosed as having AIDS or ARC,Cchronic Fatigue Syndrome, Wegener's Disease, Sarcoidosis, respiratory distress syndrome, Kibuchi's disease, antoimmune diseases such as Collagen Vascular Disease and Lupus and chronic debilitating diseases such as Alzheimer's Disease. In one procedure, presistently *M. fermentans* incognitus infected cells are grown in low cell density on sterile glass slides. Sera from suspected patients, and normal subjects are examined in an immunoperoxidase staining procedure such as that described by Hsu, S-M., et al., *Am.J.Clin.Path.* 80, 21 (1983). Using this assay, 23 of 24 sera from AIDS patients showed strong positivity. Serum from the other AIDS patient showed weak positivity. Twenty-six of 30 sera from non-AIDS normal subjects showed no reactivity. The other four non-AIDS patients showed mild to weak reactivity, but much weaker than that of AIDS patients. In addition, some of the sera from experimentally infected animals, as described above, also contained antibodies which reacted with the persistently *M. fermentans* incognitus-infected cells in this assay procedure. Similarly, *M. fermentans* infected cells can also be used in this procedure to detect antibodies in sera of infected patients as a result of homologous antigens.

In addition to this procedure, any other procedure for detecting an antigen-antibody reaction can be utilized to detect antibodies to *M. fermentans* incognitus or *M. fermentans* in the sera of AIDS patients or patients with ARC. Such procedures include, but are not limited to, ELISA, Western-blot, direct or indirect immunofluorescent assay and immunoradiometric assay. Such assay procedures for the detection of antibodies in sera of AIDS patients or patients with ARC have been described in U.S. Pat. No. 4,520,113, incorporated herein by reference, which uses HTLV-III/LAV as the antigen. Similar procedures employing *M. fermentans* incognitus or *M. fermentans* can be used. A diagnostic kit for the detection of *M. fermentans* incognitus-specific or *M. fermentans*-specific antibodies can be prepared in a conventional manner using *M. fermentans* incognitus or *M. fermentans*. It is expected that assays utilizing these techniques, especially Western-blot, will provide better results, particularly fewer false-positives.

A final procedure for detecting the presence of *M. fermentans* incognitus or other *M. fermentans* strains in suspected patients is by testing for DNA in conventional methods, preferably using probes based on the sequence of the IS-like element (SEQ ID NO:3). A preferred method is the PCR assay described above.

M. Production of Antibodies to *M. fermentans* incognitus

Antibodies against *M. fermentans* incognitus (or *M. fermentans*) can be produced in experimental animals such as mice, rabbits and goats, using standard techniques. Alternatively, monoclonal antibodies against *M. fermentans* incognitus (or other strains of *M. fermentans*) antigens can be prepared in a conventional manner. Homologous antibodies are useful for detecting antigens to *M. fermentans* incognitus in infected tissues such as lymph nodes, spleen, Kaposi's sarcoma, lymphoma tissue, brain and peripheral blood cells, as well as sera, of patients with AIDS. Any procedure useful for detecting an antigen-antibody reaction, such as those described above, can be utilized to detect the *M. fermentans* incognitus antigens in tissues of patients infected by the mycoplasma.

Rabbit antiserum has been prepared using *M. fermentans* incognitus. The antiserum positively immune stains brain and lymph node tissue from AIDS patients. To produce the antiserum, sucrose gradient banded *M. fermentans* incognitus or any form of concentrated mycoplasma is used with complete adjuvant and administered to rabbits by intraperitoneal and subcutaneous injections at multiple sites. Serum collected from the rabbits is then preabsorbed with NIH/3T3 cells, mouse liver powder and normal human peripheral mononuclear cells isolated from Ficoll-Hypaque gradients. Monoclonal antibodies may also be prepared by conventional procedures.

The antibodies are useful for detecting cells which have been infected by *M. fermentans* incognitus. This capability is useful for the isolation of *M. fermentans* incognitus from other tissues. For example, additional *M. fermentans* incognitus can be isolated by co-cultivating infected tissue from patients with AIDS and a suitable recipient cell line or cells, such as lymphocytes. The infected cells are assayed or recognized by the antibody, and *M. fermentans* incognitus can be obtained from the infected cells as described above. An affinity column can also be prepared using the antibodies and used to purify the *M. fermentans* incognitus from the infected cell lysate.

N. Vaccines

The *M. fermentans* incognitus pathogen, antigens of *M. fermentans* incognitus or homologous antigens of other *M. fermentans* strains can be utilized as a vaccine in a conventional manner to induce the formation of protective antibodies or cell-mediated immunity. The antigens can be isolated from *M. fermentans* incognitus (or other strains) or can be produced by conventional recombinant DNA techniques. The vaccines are prepared by usual procedures, such as by in vitro cell cultures, by recombinant DNA techniques, and by application of the usual and prescribed controls to eliminate bacterial and/or viral contaminations, according to well known principles and international standard requirements.

Preferably an inactivated, i.e., attenuated or killed, vaccine is utilized. The *M. fermentans* incognitus pathogen is isolated from the infected cells grown in monolayers. *M. fermentans* incognitus is killed by known procedures or modifications thereof, e.g., by the addition of betapropiolactone, Formalin or acetylethyleneimine, by ultraviolat radiation, or by treatment with psoralen or psoralen derivatives and long-wavelength ultraviolet light. Alternatively, *M. fermentans* incognitus is attenuated by conventional techniques and isolated.

The vaccine of the invention may contain one or more suitable stabilizers, preservatives, buffering salts and/or adjuvants. The vaccine may be formulated for oral or parenteral administration. Compositions in the form of an injectable solution contain a proper titer of *M. fermentans* incognitus as the active ingredient, and may also contain one or more of a pH adjuster, buffer, stabilizer, excipient and/or an additive for rendering the solutions isotonic. The injectable solutions may be prepared to be adapted for subcutaneous, intramuscular or intravenous injection by conventional techniques. If desired, the solutions may be lyophilized in a usual manner to prepare lyophilized injections.

The dosage of *M. fermentans* incognitus administered will, of course, depend on the mode of administration and the interval of administration. An optimal dose of the active ingredient and an optimal interval of administration can easily be determined by routine preliminary tests known in the art.

The antigens of mycoplasmas such as other strains of *M. fermentans* which share antigenic determinants with *M. fermentans* incognitus can also be used as vaccines to induce the formation of protective antibodies or cell-mediated immunity to *M. fermentans* incognitus. It has been found that antigens of other mycoplasmas share many antigenic determinants with *M. fermentans* incognitus, but lack the pathogenicity of *M. fermentans* incognitus. One such mycoplasma which can then be used in a vaccine against *M. fermentans* incognitus is *M. fermentans*. Other mycoplasmas useful in vaccines against *M. fermentans* incognitus can be determined using conventional techniques for comparing nucleotide sequences for sequence homology.

O. Other Disease States in Which *M. fermentans* incognitus Has Been Implicated In addition to AIDS, *M. fermentans* incognitus has been implicated in a number of other Disease states including Chronic Fatigue Syndrome, Wegener's Disease, Sarcoidosis, respiratory distress syndrome, Kikuchi's disease, autoimmune diseases such as Collagen Vascular Disease and Lupus, and chronic debilitating diseases such as Alzheimer's Disease. *M. fermentans* incognitus may be either a causative agent of these diseases or a key co-factor in these diseases.

P. Treatment of *M. fermentans* incognitus Infection

*M. fermentans* incognitus is known to be sensitive to a number of antibiotics, including doxycycline, quinalones such as ciprofloxacin, chloramphenicol and tetracycline. Therefore, effective treatment of any of the above implicated diseases should include administration of antibiotics to which *M. fermentans* incognitus is sensitive.

When using the effective antibiotics as the active ingredients of pharmaceutical compositions, the pharmaceutical compositions may be administered by a variety of routes including oral, intravenous, aerosol and parenteral. The amount of active ingredient (antibiotic) necessary to treat an *M. fermentans* incognitus infection will depend on the body weight of the patient, but will usually be from about 0.001 to about 100 mg/kg of body weight, two to four times daily.

Q. Enhancement of HIV-1 Cytocidal Effects in CD4+ Lymphocytes by *M. fermentans* incognitus Coinfection with Mycoplasma fermentans (incognitus strain) enhances the ability of human immunodeficiency virus type-1 (HIV-1) to induce cytopathic effects on human T lymphocytes in vitro. Syncytium formation of HIV-infected T cells was essentially eliminated in the presence of *M. fermentans* (incognitus strain), despite prominent cell death. However, replication and production of HIV-1 particles continued during the coinfection. Furthermore, the supernatant from cultures coinfected with HIV-1 and mycoplasma may be involved in the pathogenesis of acquired immunodeficiency syndrome (AIDS). Abstract from *Science* 251, 1074 (1991). Since the presence of *M. fermentans* incognitus is most often associated with AIDS and other acute fulminant disease states and more profoundly affects the course of its disease, it can be used to determine the prognosis of these diseases, which information can be utilized for designing therapy regimes.

The presence of *M. fermentans* incognitus in patient tissue or cell sample is determined by conventional techniques such as immunoassays, PCR analysis and DNA hybridizations as more fully described herein.

The present invention is further illustrated by reference to the following examples. These examples are provided for illustrative purposes, and are in no way intended to limit the scope of the invention.

EXAMPLE 1

Isolation of Genetic Materials from AIDS Patients and Cell Culture

Kaposi's sarcoma tissue was obtained from a patient with AIDS who died of fulminant *Pneumocystis carinii* pneumonitis. At autopsy, extensive Kaposi's sarcoma involving skin, both lungs, parietal pleura, gastrointestinal tract, pancreas, liver, kidney and lymph nodes was found. The tissue used to extract genetic material was derived from Kaposi's sarcoma in the patient's retroperitoneal lymph nodes, five to six hours after death. Permanent paraffin sections confirmed near-total effacement of lymph node architecture by Kaposi's sarcoma.

Splenic tissue was obtained from a second patient with AIDS who also died of *P. carinii* pneumonitis. No tumor (i.e., Kaposi's sarcoma or lymphoma) was identified at autopsy. Paraffin sections of the splenic tissue used to extract genetic material showed congestion and lymphocyte depletion.

The splenic or Kaposi's sarcoma tissue (1-2 g) was minced into small pieces and treated with collagenase (5 mg/ml) in 1 ml phosphate-buffered saline (PBS) at 37° C. for 15 minutes. The tissue suspension was then treated with proteinase K (250 g/ml) in 10X volume of 150 mM NaCl, 10 mM Tris (pH 7.5), 0.4% SDS, at 65° C. for 30 minutes and at 37° C. for ten hours. Phenol extraction (twice) followed by phenol/chloroform-/isoamylalcohol (25:24:1) and chloroform/isoamylalcohol (24:1) extraction were used to purify genetic material. Grossly visible high molecular weight DNA was easily observed after ethanol precipitation. The genetic materials were redissolved in aqueous phase (1 mM Tris, 1 mM EDTA) after overnight air-drying. The recovered genetic materials contained high molecular weight DNA and 30–40% RNA of various size. The procedures of isolating genetic materials from the cultures of the primary transformants and normal human fibroblasts (ATCC, CRL-1521) were similar. The pellets of 10–20$\times 10^6$ cells were mixed directly with 10X volume of proteinase K (250 g/ml) in the same buffer without collagenase treatment.

EXAMPLE 2

Transfection of NIH/3T3 Cells

The transfection procedures were slightly modified from that of Graham et al., supra. Approximately 30 micrograms of nucleic acid isolated from Kaposi's sarcoma tissue, splenic tissue, normal human fibroblast, or salmon sperm were precipitated with calcium phosphate in each 60 mm Petri dish culture (containing about $5\times 10^5$ NIH/3T3 cells). The DNA precipitate was removed after cells were incubated at 37° C. for 12 hours. After an additional 24 hours, each plate of cells was trypsinized and reseeded into four to five 60 mm Petri dishes. The cells received five minutes of 15% glycerol treatment in 10% fetal bovine serum (FBS, Gibco) Dulbecco's modified Eagle's medium (DMEM) before the splitting as described by Copeland et al., supra. The subcultures were fed with Dulbecco's medium with 5% FBS and re-fed with this medium at intervals of three to four days. Foci of morphologically transformed cells became evident in two weeks. Colonies were harvested after three weeks.

NIH/3T3 cells transfected with genetic material derived from both spleen and Kaposi's sarcoma tissue of AIDS patients produced morphologically transformed colonies which were visible within two weeks. The phenotypical transformation was characterized by the rapid overgrowth of the transfected cells which piled up in multilayers and formed grossly visible foci. Transformation efficiency was approximately 0.01 to 0.02 identifiable foci per microgram of donor nucleic acid. In contrast, no transformed foci were identified in parallel cultures using DNA from salmon sperm or nucleic acid from human fibroblasts. The transformants were recovered from these phenotypically malignant foci after two weeks and cultured in monolayers. Transformants retained their tendency of piling up in multilayers and reached more than three-fold higher cellular density than normal NIH/3T3 fibroblasts.

EXAMPLE 3

Confirmation of NIH/3T3 Cell Transformation

To confirm that transformation of the NIH/3T3 cells was mediated by active transforming genetic elements, the primary transformants' capacity to transmit their malignant phenotypes of rapid cell growth and pile-up (lack of cell-cell contact inhibition) in high cellular density in subsequent cycles of transfection was examined. Thus, a second cycle of transfection, as described above, was performed using genetic material which was isolated as previously described from some of the primary transfectants. A higher efficiency of transformation was observed in the second cycle of the transfection assay (up to 0.05 foci per microgram of donor nucleic acid). These results indicate that genetic materials isolated from spleen and Kaposi's sarcoma tissues of the AIDS patients contained active transforming elements that induce malignant transformation of rapid cell growth upon transfection and retransfection of phenotypically normal cells. DNA from first and second stages of transformation clones selected for further studies were then characterized with respect to the presence of human DNA repetitive sequences by probing with $^{32}P$ nick-translated Blur 8-plasmid. No human repetitive DNA sequences were detected in these transformants.

EXAMPLE 4

Analysis of Transformants

Normal NIH/3T3 and transformant clones were all routinely maintained in monolayer cultures with 10% FBS-supplemented Dulbecco's media. Autoclavable slides (Cell-line Asso. Inc.) were previously sterilized and overlaid with trypsinized cell suspension ($1 \times 10^5$ cells/ml) in square petri dishes. The cultures were incubated at 37° C. in a 5% $CO_2$ incubator for 48 to 72 hours. The culture slides were washed three times with cold PBS, air-dried and stored at 4° C. Immunocytochemistry was performed within two to three days on these stored slides.

The monolayers were scraped directly from the cultures. The cells were harvested by centrifugation of 1,000 rpm for 10 minutes. The cell pellets were fixed overnight at 4° C. in 2.5% glutaraldehyde in phosphate buffer and post-fixed with 1% $OsO_4$. The fixed tissues were then processed by standard methods and embedded in Maraglass 655. The grids with ultra-thin sections were double-stained with uranylacetate and lead citrate. The specimens were then examined under an electron microscope with 60 kv or 100 kv voltage. Negative staining of the virus-like particles in the culture supernatants was performed. Briefly, the particles in the culture supernatant were pelleted through a 5 ml 20% sucrose barrier in SW41 centrifugation tubes, at 40,000 rpm for one hour. The pellets were then resuspended in 1/50 to 1/100 volume of Tris-normal saline (pH 7.4, 0.05M Tris). The suspensions were directly put on formvar coated grids and negatively stained with 2% phosphotungstic acid (PTA) (pH 7.2).

Two of the transformants (Sb51 and Kb43, from different patients) were studied in detail. These two transformants were obtained from the second cycle transfections with genetic materials from Kaposi's sarcoma spleen and tissues, respectively. Sb51 cells persistently infected with *M. fermentans* incognitus were deposited with the ATCC under No. CRL 9127 under the Budapest Treaty on Jun. 17, 1986. The cells grew in high cellular density with no significant cytopathic changes. However, occasional lytic plaques, with cells showing cytopathic changes, were noted after the transformants reached saturated density. Many physiologic factors, including incubation temperatures and culture media, were found to affect the degree of lytic plaque formation. For example, a reduction in the temperature to 32° C. results in higher lytic plaque formation. Sb51 cells tended to pile-up in a monolayer culture. Foci of rapid cell overgrowth and pile-up into multicellular layers can best be appreciated under low-power light microscopy with a dark background. Cytopathic changes commonly occurred in the centers of the high cell density foci. Detachment of the cytolytic cells in the center of hyperplastic foci was evident. There were prominent cytopathic effects among the densely-packed cells on the peripheral edges of the lytic plaque. These cells rounded up and appeared smaller in size with a shrunken configuration.

The monolayers of Sb51 and Kb43 which showed significant cytopathic changes in at least 30% of cells were examined by electron microscopy.

In those cells undergoing cytopathic changes numerous *M. fermentans* incognitus cells were seen, mainly in the cytoplasm of disrupted cells. Early cytopathic changes showing nuclear chromatin condensation and margination was seen at 15,000X magnification. Accumulation of *M. fermentans* incognitus nucleocapsids within the nucleus is prominent. Numerous *M. fermentans* incognitus particles of different maturation stages were seen in the cytoplasm at 45,800X magnification. Most of the mature *M. fermentans* incognitus cells in the cytoplasm are lined up along the plasma membrane while others are free. The *M. fermentans* incognitus cells were roughly spherical enveloped particles of heterogenous sizes. The majority of mature *M. fermentans* incognitus cells were 140–280 nm, with an overall range of 100–900 nm. The intact *M. fermentans* incognitus particle had a well-defined outer limited membrane about 8 nm thick and tightly packed internal nucleocapsids. Occasionally, the nucleocapsids were seen to condense into compact cores inside the *M. fermentans* incognitus cell. Although the *M. fermentans* incognitus outer envelope was well-defined and thick, it was not rigid. Elongated, ovoid, and pleomorphic forms with protrusions were not uncommonly identified among the *M. fermentans* incognitus cells (at 45,800X magnification).

To further confirm the ultrastructure and morphology of *M. fermentans* incognitus, the unsectioned *M. fermentans* incognitus were examined by pelleting *M. fermentans* incognitus particles from Sb51 and Kb43 culture supernatants through a 20% sucrose gradient barrier. The particles were resuspended in Tris-normal saline at 1/100 of original volume. The precipitated particles were directly examined under electron microscopy following negative stainings with PTA. Some preparations of the intact *M. fermentans* incognitus particles were briefly fixed with 0.5% Formalin to preserve the *M. fermentans* incognitus morphology as well as to avoid possible infectious problems in the laboratory. The negative staining preparations of *M. fermentans* incognitus usually revealed more surface detail together with their internal structure. There was some heterogeneity in both particle size and shape. Some *M. fermentans* incognitus cells often appeared to be elongated or had irregular bulging protrusions (when viewed at 101,800X magnification. The internal component consisted of strands arranged more or less parallel to each other and to the long axis of the particle. The internal nucleocapsid strands appeared to be better preserved in the particles fixed with low concentrations of Formalin. The well-defined envelope revealed inconspicuous spikes on the external surface. At high magnification (370,000X), *M. fermentans* incognitus demonstrated complex membranous envelopes. The released nucleocapsids appear to be uncoiled.

EXAMPLE 5

PCR Assay for *M. fermentans* incognitus

An assay of urine sediments prepared in Example 6 is illustrative of a PCR assay. The amplification of selective DNA sequences was performed with thermostable Taq DNA polymerase (Native Taq; Perkin Elmer Cetus, Norwalk, Conn.) (10) in the automated Perkin-Elmer Cetus DNA thermal cycler (Norwalk, Conn.). One ml of urine sediment prepared and filtered as described in Example 6 was first centrifuged at 1,500 x g for 15 min. Nine-hundred ul of the supernatant was removed. Proteinase K was added to the remaining 100 ul sample (final concentration of 200 ug/ml) and the sample was digested at 56° C. for 2 hrs. Before PCR analysis the digested samples were heated at 95° C. for 10 min. Each 10 ul urine sediment sample to amplified was adjusted to a total volume of 160 ul with PCR buffer containing a final concentration of 50 mM KCl, 20 mM Tris-HCl (pH 8.3), 1 mM $MgCl_2$, 0.001% gelatin, each primer (RW004 (SEQ ID NO:15) and RW005 (SEQ ID NO:16) (R. Y-H Wang et al., Abstr. Gen. Meet. Am. Soc. Microbio. 1991, G-5, p. 134) at 0.5 uM, each dNTP at 250 uM and 2.5 U of Taq DNA polymerase. It has been found that these primers are preferred over the RS47 and RS49 primers used in PCR assays below (Example 16 and 19). The samples were overlaid with 3 drops of mineral oil (50 ul). Samples were denatured at 94° C. for 35 sec, annealing of primers at 56° C. for 45 sec and extension at 72° C. for 1 min. The annealing time was increased by one sec/cycle during the amplification. After the final cycle, the annealing time was increased to 5 min, followed by extension for 5 min. Twenty ul aliquots from each amplified sample were removed and analyzed on a 6% polyacrylamide gel in 1X Tris-borate-EDTA buffer (Maniatis et al., *Molecular Cloning: a laboratory manual.* Cold Spring Harbor Laboratory, Cold Spring Harbor, N.Y. (1982)). The gels were stained with ethidium bromide and the DNA visualized by UV fluorescence. The fractionated DNA was electroblotted onto a Zeta-Probe membrane (Bio-Rad, Richmond, Calif.) at 100 volts for 2 hrs., in 0.5X Tris-acetate-EDTA buffer (Maniatis et al., supra), followed by denaturation and fixation in 400 mM NaOH, 2 mM EDTA for 10 min. at room temperature. The Zeta-Probe membrane was rinsed 3 times with 2X SSC in 20 mM Tris-HCl (pH 7.5) and air dried for 10 min. Prehybridization was carried out in 30% formamide, 4X SSC, 5X Denhardt's, 20 mM Tris-HCl, (pH 7.5), 2 mM EDTA, 1% SDS and 350 ug/ml of denatured salmon sperm DNA at 30° C. Hybridization was in the same mixture but containg the oligonucleotide probe RW006 (SEQ ID NO:17) (Wang et al., *Abstr. Gen. Meet. Am. Soc. Microbiol.* 1991, G-5. p. 134) which was 5'end labeled with $^{32}P$-ATP, and was conducted overnight at 30° C. After hybridization the membrane was washed at 45° C. in 2X SSC, 0.5% SDS four times (30 min. each).

Figure 8A:
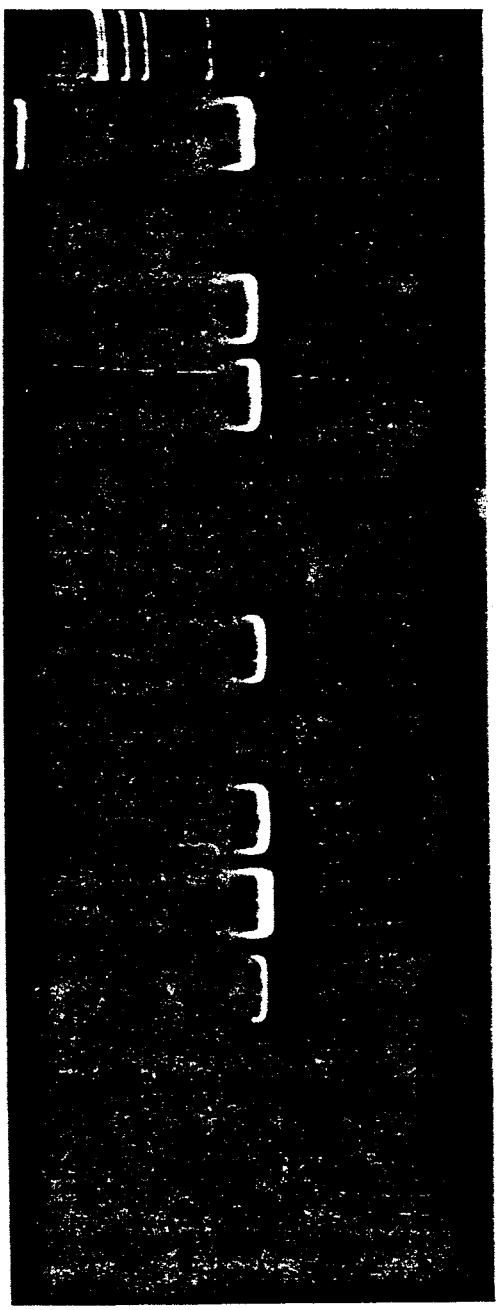
FIG. 8A shows detection of *M. fermentans* incognitus from urine specimens following PCR stained with ethidium bromide.
Figure 8B:
FIG. 8B shows detection of *M. fermentans* incognitus from urine specimens following PCR stained with Probe RU006.

Forty-three urine sediments obtained from 40 HIV positive patients and 50 urine sediments obtained from HIV negative healthy control individuals were tested for the presence of *M. fermentans* specific DNA sequences by using the PCR assay. Primer pairs of synthetic oligonucleotides, designated RW004 (SEQ ID NO:15) and RW005 (SEQ ID NO:16) containing specific sequences within the insertion sequence (IS)-like genetic element found in multiple copies in *M. fermentans* mycoplasmas were used to amplify a 206 bp segment of the IS-like DNA. Ten of 43 urine sediments obtained from HIV positive patients with varying stages of AIDS disease, tested positive for the presence of *M. fermentans* DNA. In contrast, none of the 50 urine sediments obtained from HIV negative non-AIDS controls tested positive. FIG. 8 shows the PCR results of representative samples from HIV negative controls (FIG. 8, lanes b and c) and HIV positive patients' urine sediments (FIG. 8, lanes d-m). Lane n contained one femtogram *M. fermentans* incognitus DNA diluted into one microgram of human placental DNA and lane o contained pUC18 DNA digested with MspI, serving as size markers. A distinct band could be observed in the ethidium bromide stained gel at a position corresponding to the 206 bp fragment amplified in *M. fermentans* control DNA (FIG. 8A, lane n), and in positively amplified AIDS patients' urine sediments (FIG. 8A, lanes d-f, h, k and l). The RW006 (SEQ ID NO:17) probe hybridized strongly to all positively amplified samples (FIG. 8B, lanes d-f, h, k, l, and n).

Figure 7A:
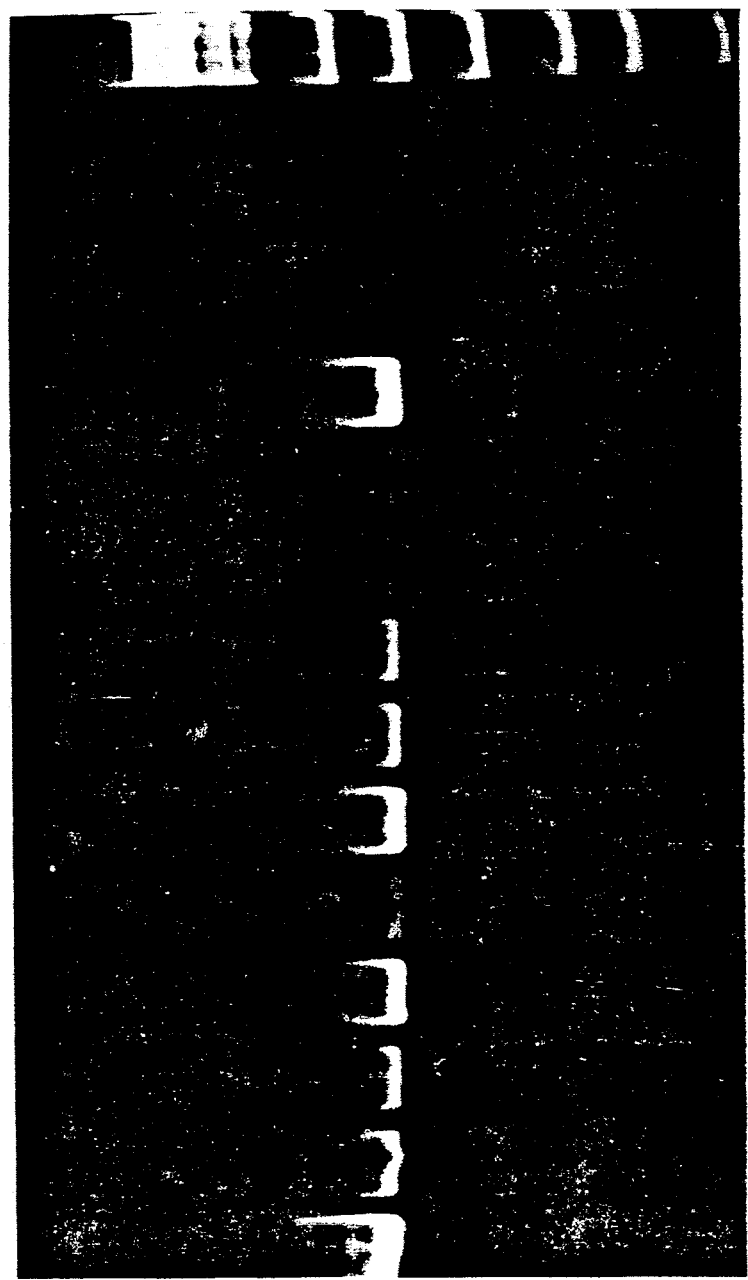
FIG. 7A shows detection of *M. fermentans* from urine specimens following PCR stained with ethidium bromide.
Figure 7B:
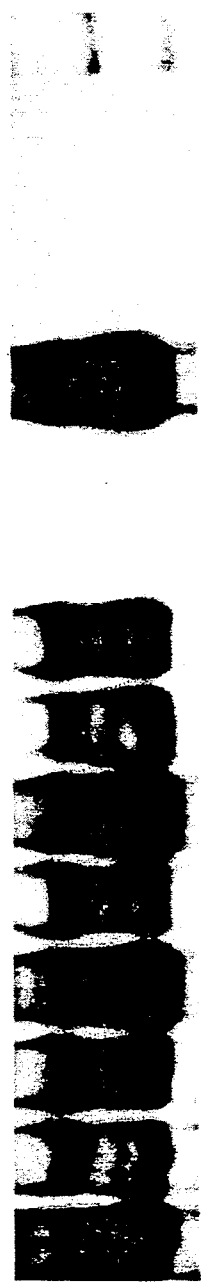
FIG. 7B shows detection of *M. fermentans* from urine specimens following PCR stained with Probe RU006.

Using a similar procedure, *M. fermentans* species including the prototype strain PG-18 and new clinical isolates from patients with AIDS, which had tested negative in previous PCR reactions were analyzed in a PCR reaction using RW004 (SEQ ID NO:15) and RW006 (SEQ ID NO:16) as primers. The assay consistently deteted 1 fg of DNA in all species (FIG. 7). Specificity of the reaction has also been examined by attempting to amply the DNAs isolated from other human or non-human mycoplasmas, common tissue culture contaminating mycoplasmas, Gram-positive or Gram-negative bacteria, mouse, monkey and human cell culture and/or tissue. The reaction does not produce the specific 206 bp DNA fragment (Table 1).

TABLE 1

SPECIFICITY OF PCR FOR *M. FERMENTANS* USING UNIQUE SEQUENCES WITHIN THE IS-LIKE GENETIC ELEMENT

| Sources | Concentration of DNA tested | Positivity |
|---|---|---|
| Mycoplasmas | | |
| *M. fermentans* | | |
| ATCC 19989 | 1 fg | + |
| incognitus strain | 1 fg | + |
| PG-18 | 1 fg | + |
| K-7 | 1 fg | + |
| MT-2 | 1 fg | + |
| and nine clinical isolates | 1 fg | + |
| *M. hominis* (ACTCC 15488) | 1 ng | − |
| *M. orale* (ATCC 23714) | 1 ng | − |
| and one clinical isolate | 1 ng | − |
| *M. salivarium* (ATCC 23064) | 1 ng | − |
| and two calinical isolates | 1 ng | − |
| *M. buccale* | 1 ng | − |

TABLE 1-continued

SPECIFICITY OF PCR FOR *M. FERMENTANS* USING UNIQUE SEQUENCES WITHIN THE IS-LIKE GENETIC ELEMENT

| Sources | Concentration of DNA tested | Positivity |
|---|---|---|
| *M. pneumoniae* (ATCC 15531) | 1 ng | — |
| *M. genitalium* (ATCC 33530) | 1 ng | — |
| *M. arginini* (ATCC 23838) | 1 ng | — |
| *M. pirum* | 1 ng | — |
| *M. alvi* | 1 ng | — |
| *M. moatsii* | 1 ng | — |
| *M. sualvi* | 1 ng | — |
| *M. iowae* | 1 ng | — |
| *M. arthritidis* | 1 ng | — |
| *M. hyorhinis* (ATCC 17981) | 1 ng | — |
| *Acholeplasma laidlawii* (ATCC 23206) | 1 ng | — |
| *Ureaplasma urealyticum* (ATCC 27618) | 1 ng | — |
| Bacteria | | |
| *E. coli* | 1 ug | — |
| *Streptococcus pneumoniae* | 1 ug | — |
| *Clostridium perfringens* | 1 ug | — |
| Mouse | | |
| NIH/3T3 | 1 ug | — |
| Spleen (Balb/c) | 1 ug | — |
| Liver (Balb/c) | 1 ug | — |
| Brain (Balb/c) | 1 ug | — |
| Monkey | | |
| Vero cells (ATCC CCL18) | 1 ug | — |
| Spleen (green monkey) | 1 ug | — |
| Liver (green monkey) | 1 ug | — |
| Brain (green monkey) | 1 ug | — |
| Human | | |
| CCRF-cem (ATCC CCL119) | 1 ug | — |
| Placenta (nl. delivery) 4X | 1 ug | — |
| PBMC (nl. donor) 50X | 1 ug | — |

EXAMPLE 6

Direct Isolation of AIDS-associated Myoplasma From Infected Tissues of AIDS Patients Urine was collected in sterile containers and concentrated 10-fold by centrifugation (3000×g for 15 min. at 4° C.) and resuspended in 1/10 of the original urine. The resulting urine sediments were diluted 1:10 in modified SP-4 media (Lo et al. (1989(a), *Am. J. Trop. Med. Hyg.* 41: 586–600) and then filtered through a 0.22 um filter.

The filtered urine sediments (10 ml), previously diluted in modified SP-4 media, were cultured in 25 cm² tissue culture flasks and also cultured with a further 1:10 aerobically and in GasPak jars (BBL, Microbiology Systems, Cockeysville, Md.) anaerobically. Flasks showing a color change were subcultured to modified SP-4 agar to confirm the mycoplasma growth. Speciation of various mycoplasma colonies obtained was assayed by immunofluorescence of colonies on agar using species-specific FITC-conjugated antibodies (Del Guidice et al. (1967), *J. Bacteriol.* 93:1205-1209).

Restriction endonuclease cleavage and Southern blot hybridization of genomic DNA from prototype strains and new clinical isolates of *M. fermentans* was carried out basically as previously described (Lo et al. (1989a), supra; Lo et al. (1989b). *Am. J. Trop. Med. Hyg.* 41:213–226). DNA was isolated from cultures of each isolate or strain of *M. fermentans*, purified by standard methods, and digested with either EcoRI or HindIII restriction enzymes (Gibco-BRL, Gaithersburg, Md.). The enzyme digests of NDA, after electrophoresis in 1% agarose, were transferred to a Zeta-Probe membrane by the Southern blot method. Each filter was prehybridized in 50% formamide, 4 x SSC, 5 x Denhardts', 20 mM Tris-HCl (pH 7.5), 2 mM EDTA, 1% SDS, and 250 ug/ml denatured salmon sperm DNA for at least 4 hrs at 42° C. and hybridized with $^{32}P$ nick-translated psb-2.2 DNA (Hu et al. (1990). Gene 93:67–72) at 42° C. in the prehybridization solution as described, (Lo et al. (1989b), supra). After hybridization the blots were washed at 55° C. in x 2 SSC, 0.5% SDS, 10 mM Tris-HCl (pH 7.5) for 120 min. with 4 changes and then washed at 50° C. in 0.5 x SSC, 0.1% SDS for 60 min. with 2 changes before autoradiography (Lo et al. (1989b), supra).

Figure 9:
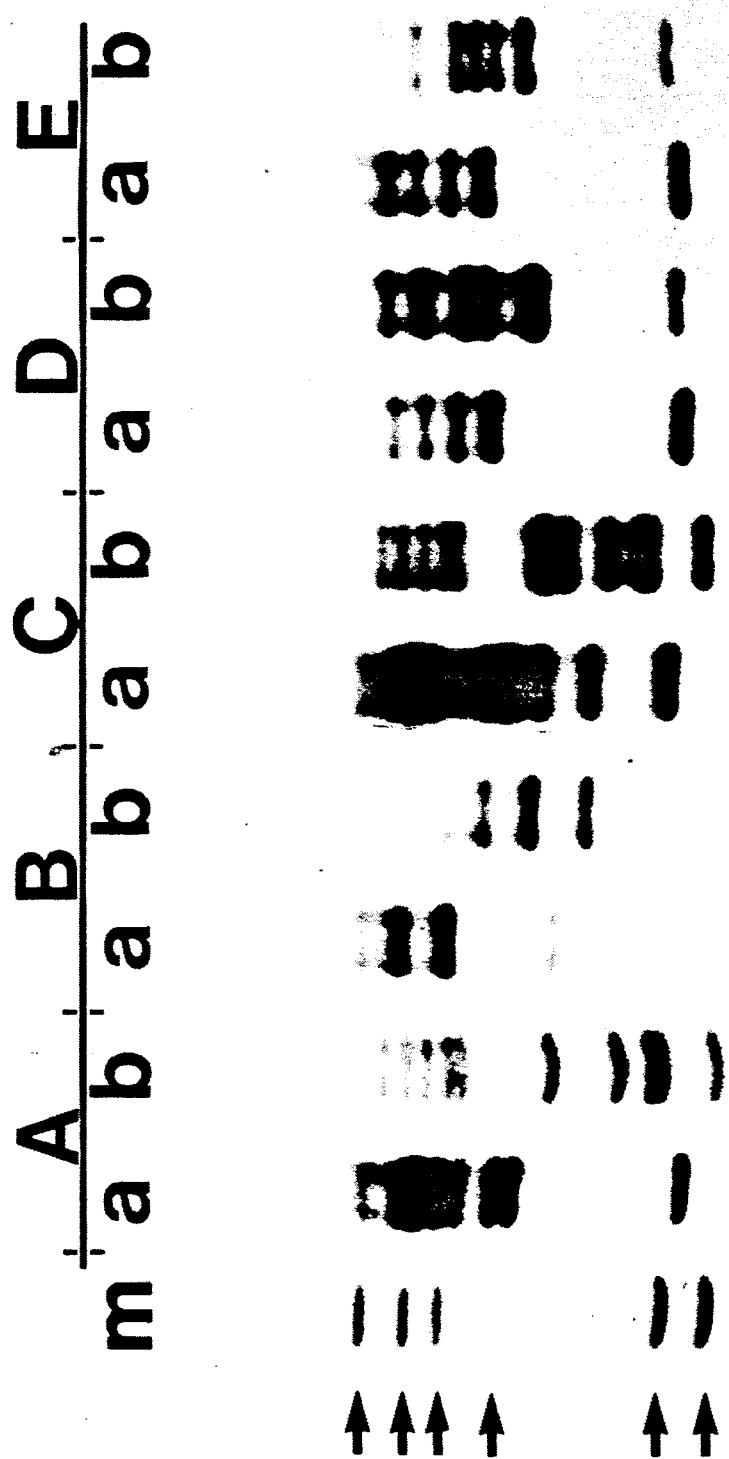
FIG. 9 shows analysis of genomic DNA from various strains or isolates of *M. fermentans*.

*M. fermentans* was isolated and grown in modiifed SP-4 media from 3 of the AIDS patients' urine sediments which tested positive in the PCR assay of Example 5. DNA was prepared from cultures of the new clinical isolates and compared with that of representative *M. fermentans* strains in Southern blot analysis. The DNASs were digested with EcoRI (a lanes) or HindIII (b lanes), fractionated in an agarose gel and hybridized with $^{32}P$-labeled psb-2.2 (FIG. 9). Lane m is HindIII digested lambda phage DNA used as marker of 23.1, 6.6, 4.4, 2.3 and 2.0 kb, respectively. The new clinical isolates (FIG. 9, D and E) have similar but distinct restriction enzyme patterns from K7 strain (FIG. 9,A) PG18 prototype strain (FIG. 9,B), original *M. fermentans* incognitus (FIG. 9,C) which indicates that they are indeed independent isolates.

*M. fermentans* mycoplasmas were successfully isolated and grwon in mycoplasma culture from 3 urine sediments derived from 2 HIV positive individuals (Table 1). Five *Ureaplams Urealyticum* and two *M. hominis* were also isolated from the 43 cultures of AIDS patients' urine sediments. Fifty urine sediments similarly prepared from age-matched HIV negative healthy controls did not grow *M. fermentans* mycoplasmas. In this study, 23 *Ureaplasma Urealyticum* and *M. hominis* were isolated from the 50 control urine sediments (Table 2).

TABLE 2

Isolation of Different Species of Mycoplasma and *Ureaplasma urealyticum* from Urine of HIV positive AIDS patients and HIV negative non-AIDS controls

| | Source of Urine | |
|---|---|---|
| Species | HIV Positive AIDS Patients | HIV Negative Controls |
| *M. fermentans* | 3/43[a] (7.0%)[b] | 0/50 (0%) |
| *M. fermentans* | 2/43 (4.7%) | 1/50 (2.0%) |
| *U. urealyticum* | 5/43 (11.6%) | 23/50 (46.0)% |

[a]Number of isolates over number of samples cultured
[b]Percentage of isolation

EXAMPLE 7

Isolation and Gradient Banding of *M. fermentans* incognitus

Sb51 cells grown as monolayers were briefly trypsinized and pelleted by centrifugation at 1,000 rpm for 10 minutes. The cell pellet was resuspended with an equal volume of Dulbecco's medium. The cells were lysed by five cycles of freezing and thawing to release the cell-associated *M. fermentans* incognitus particles. The particles were pelleted through a 20% sucrose barrier in a SW41 centrifuge tube by centrifugation at 40,000 rpm for 45 minutes. The particles were resuspended in PBS and banded in a sucrose isopycnic gradient (20% to 60%). Electron micrographs of the *M. fermentans* incognitus cells in the cytoplasm of degenerating Sb51 cells is shown in FIG. 10. The *M. fermentans* incognitus particles were localized at a density of about 1.17 to about 1.20 (FIGS. 10(B) and 10(C)). The *M. fermentans* incognitus particles were directly identified by electron microscopy with PTA negative staining.

EXAMPLE 8

Production of Antibodies Against *M. fermentans* incognitus

*M. fermentans* incognitus particles were isolated as described in Example 7 from $5 \times 10^6$ Sb51 cells, and mixed with Freund's adjuvant. Rabbits were injected with the immunogen twice at a two- to three-month interval. A good antibody response to *M. fermentans* incognitus was obtained after the second immunization.

EXAMPLE 9

Infection of Mice by *M. fermentans* incognitus

*M. fermentans* incognitus was isolated as described in Example 7, from $5 \times 10^6$ Sb51 cells, and resuspended in a small amount of PBS. The *M. fermentans* incognitus suspension was injected into either a six-week-old NIH (Nu) male mouse or a six-week-old Balb/c male mouse. The injection was performed either intravenously or intraperitoneally. Sixty percent of the nude mice who received intravenous or intraperitoneal injections of the *M. fermentans* incognitus preparation showed evidence of skin rashes with areas of erythematous changes and conjunctivitis in 10 to 12 days. One animal also showed prominent periorbital edema. These signs disappeared after two to three weeks. All the animals appeared to recover from the acute infection. Two animals then developed pruritic skin rashes after six weeks. These two animals and the other two animals died or became too sick, and had to be sacrificed in three months. Therefore, 40% of the animals had died in the first three months following injection. One animal which did not develop recognizable skin lesions showed systemic lymphadenopathy and paralysis. The animal appeared to be wasting and experienced complete paralysis of its hind legs. One animal had several purplish skin lesions which were slightly raised. At necropsy, all lymph nodes in these animals showed lymphocyte depletion. Only very small lymph nodes were identified on gross examination. In contrast, disseminated lymphadenopathy was seen in the inguinal, axillary, cervical, mediastinal and mesentery lymph nodes. The animal also developed hepatosplenomegaly. Histologic sections of the lymph nodes revealed prominent plasmacytosis. Areas of sinus histiocytosis were also noted. The plasma cell effaced normal lymph node architecture and diffusely infiltrated the sinus. Lymph nodes in all the other animals showed lymphocyte depletion. Only small lymph nodes could be identified grossly.

Histologic sections of purplish skin lesions revealed spindle cell proliferation. The spindle cells appeared to infiltrate cutaneous adipose tissue as well as underlying muscles. Extravasation of red blood cells was seen in some areas. Mitotic figures were identified, but not prominent. Histologic examination of the liver of the animal also revealed spindle cell proliferation in the periportal areas. The homogeneous tumor cells exhibited more epithelioid appearance. Numerous red blood cells were trapped in the intercellular slits. Electron microscopic examination of the infiltrating spindle cells in the skin lesions revealed cells with cytopathic changes. An accumulation of *M. fermentans* incognitus nucleocapsids were seen in many of the nuclei, and some in the cytoplasm. The morphology and the characters of these *M. fermentans* incognitus nucleocapsids were similar to those observed in Sb51 cells previously described. Mature *M. fermentans* incognitus cells were also identified in some of the disrupted cells. Both nucleocapsids and *M. fermentans* incognitus cells were often seen in dilated cisternae of smooth endoplasmic reticulum. Electron microscope studies of the periportal spindle cell lesions in the liver similarly revealed prominent infection of *M. fermentans* incognitus.

Balb/c mice infected with the *M. fermentans* incognitus also appeared to be sensitive to the *M. fermentans* incognitus pathogen. Three of seven animals died in the first three months following infection. Two more animals died in the fourth month following infection. None of the control animals showed any disease in four months. Clinical evaluation of skin rashes and lymphadenopathy while these animals were alive was much more difficult. At necropsy, all of the animals were found to be lymphocyte-depleted. The animals had very small lymph nodes and spleens. Lymph nodes were often unrecognizable grossly. The lungs of these animals were found to have severe pneumonitis. M-Ag and toluene blue staining revealed *P. carinii*. Therefore, these animals were believed to be severely immunodeficient. Two of the animals who survived for more than four months were found to have antibody in their sera which recognized Sb51 cells but not NIH/3T3 parental cells. Immunoperoxidase reaction of the sera showed positive reactions in both the nuclei and the cytoplasm of Sb51 cells indicating the presence of *M. fermentans* incognitus.

EXAMPLE 10

Infection of Non-Human Primates with the *M. fermentans* incognitus

Figure 11:
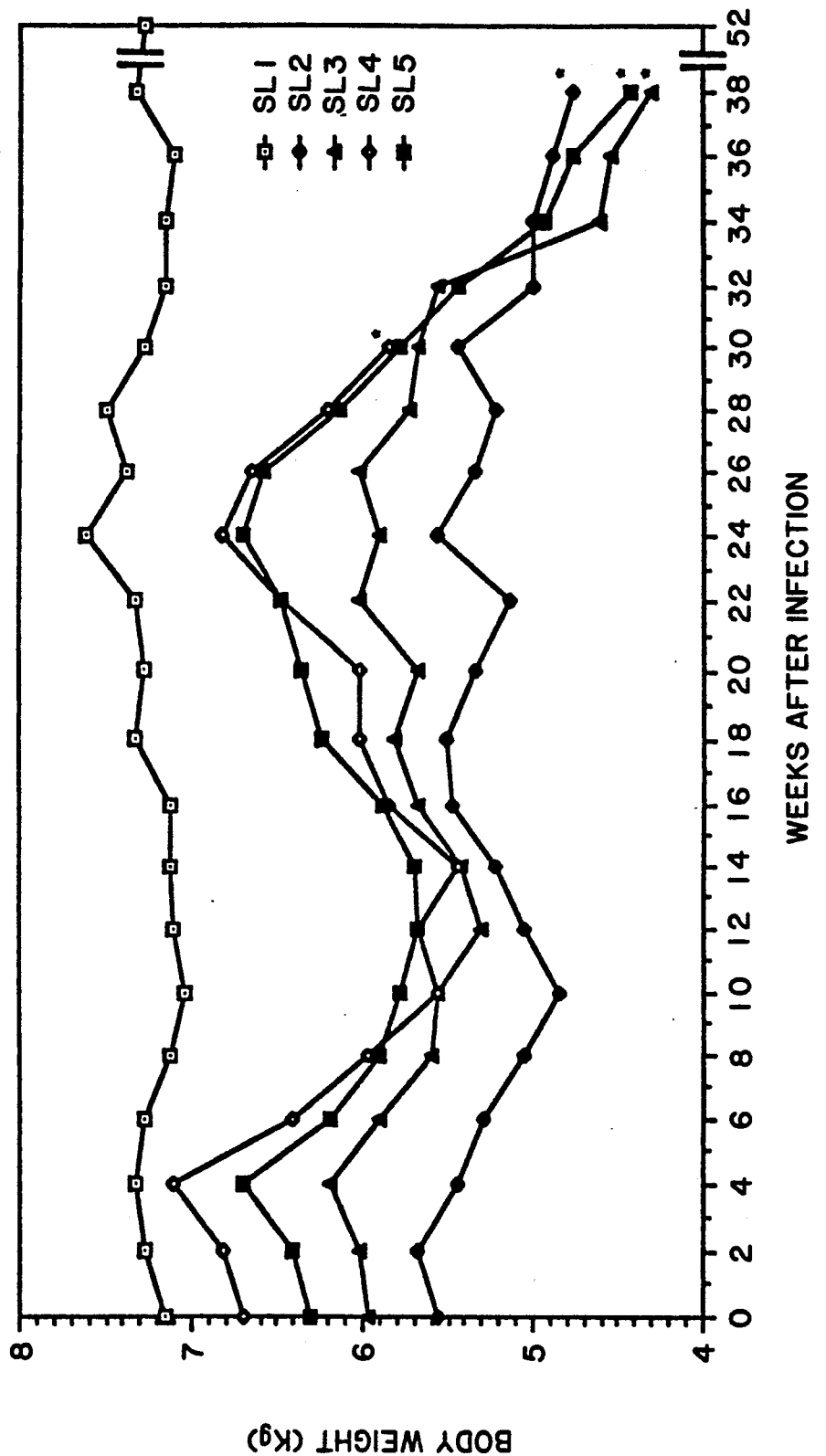
FIG. 11 shows a graph of body weight of monkeys over time, after innoculation with *M. fermentans* incognitus.

Four silver leaf monkeys (presbytis cristatus) were inoculated (intraperitoneally) with partially purified *M. fermentans* incognitus (see Example 7 above). All four monkeys displayed a wasting syndrome as shown in FIG. 11, and died within seven to nine months. A control monkey which had been inoculated with a preparation derived from normal NIH/3T3 cells did not exhibit the wasting syndrome and did not die during the seven- to nine-month period.

The monkeys were followed daily for signs of illness, and examined once every two weeks for body weight, body temperature and general physical condition. Serial blood samples were also collected every two weeks for blood cell counts and antibody and antigen assays.

Two weeks after *M. fermentans* incognitus inoculation, one monkey showed signs of a flu-like syndrome which persisted for six weeks. This same monkey later developed facial/neck edema (between week 8 and week 12), poor skin tones, and dermatities associated with alopecia (after week 18). This was the first monkey to succumb, expiring at the 29th week after *M. fermentans* incognitus inoculation. The animal had apparently been afebrile throughout the whole course, except at the time of the 16th week after *M. fermentans* incognitus inoculation.

Body weights of all *M. fermentans* incognitus inoculated monkeys fluctuated. However, a progressive weight loss was noted among these animals in the last 14 weeks of the experiment (FIG. 11). No diarrhea was detected for any of the animals. Two of the monkeys also had transient lymphadenopathy at 4 to 14 weeks and 4 to 20 weeks after *M. fermentans* incognitus inoculation, respectively. Three monkeys appeared to have persistent low grade fever in the earlier course of the experiment, but no significant febrile response could be detected in the later stages (the last month). The moribund animals revealed paradoxical hypothermia in the final periods. One monkey revealed signs of tremor, rigidity and imbalance in the terminal stage. The clinical signs strongly suggested a neurological illness. Accurate assessment, however, was hampered by the obvious physical weakness of the animal which may have been due to the prominent weight loss.

At necropsy, no malignant tumor or opportunistic infection could be identified in any *M. fermentans* incognitus inoculated animal. Histopathology of the lymph nodes obtained from these monkeys revealed features of lymphocyte depletion. There was spindle cell proliferation in the perinodal areas, but typical diagnosis of Kaposi's sarcoma could not be made.

One animal revealed persistent and significant leukocytosis that lasted for about three months (between 16 to 28 weeks after inoculation). In contrast, two other monkeys showed prominent leukopenia in the terminal stage. Differential cell count revealed that their lymphocytes were 448, and 410 per microliter, respectively. Both red blood cell and platelet counts fluctuated. Transient periods of low platelet counts were observed during the course of the study for all animals. However, no animal was thrombocytopenic in the terminal stage.

To study if the *M. fermentans* incognitus inoculated animals developed an immune response and produced specific antibodies, the serum samples obtained from serial bleedings during the course of the experiment were examined. Sucrose gradient-banded *M. fermentans* incognitus was used as the antigen in the Western blot antibody analysis. Seroconversions which were defined by definite changes of the immunoreactive patterns and development of new reactive bands on the blot strips after *M. fermentans* incognitus inoculation, occurred unusually late. Only one monkey had a prominent antibody response, which however, occurred as late as seven months after *M. fermentans* incognitus inoculation. Another monkey had a transient antibody response for two months (six months to eight months after *M. fermentans* incognitus inoculation) which apparently disappeared in the terminal stage, one month before the animal expired. The other two monkeys had a poor and very late immune response which again only occurred in the terminal stage, 4 to 6 weeks before the animals expired. No antibody response could be detected in the control monkey. Estimated molecular weights for the newly developed major protein bands which revealed a positive reaction with the first monkey's sera obtained seven months post *M. fermentans* incognitus inoculation, were 97, 88, 84, 32.5 and 27.5 kilodaltons, respectively.

*M. fermentans* incognitus antigens in the animals' sera obtained during the course of the experiment were also measured. By sandwiched radioimmunoassay using rabbit antiserum raised against *M. fermentans* incognitus antigens, periodic *M. fermentans* incognitus antigenemia was detected in the three monkeys which failed to produce a prominent antibody response. The first monkey to succumb showed the most prominent, early and persistent *M. fermentans* incognitus antigenemia.

To further confirm that these animals inoculated with *M. fermentans* incognitus suffered a fatal systemic infection by *M. fermentans* incognitus, DNA obtained from various tissues taken at necropsy was directly examined. In this study, the highly sensitive polymerase chain reaction (PCR) method of selective DNA amplification was used. Primer pairs (RS47 (SEQ ID NO:13)/RS49 (SEQ ID NO: 14)) of synthetic oligonucleotides with *M. fermentans* incognitus-specific sequences and Taq DNA polymerase were used for 35 reaction cycles of *M. fermentans* incognitus-specific DNA amplification. The primer pairs RS47/RS49 were previously shown to span the first 160 bp region at one terminal end of *M. fermentans* incognitus DNA of psb-2.2 (SEQ ID NO:2). The presence of *M. fermentans* incognitus-specific DNA in the amplified products was confirmed by blot hybridization using synthetic oligonucleotide probe (RS48 (SEQ ID NO:1)) 5' end-labeled with $^{32}P$. The typical positive hybridizations for *M. fermentans* incognitus-specific DNA products revealed diagnostic 160 bp DNA fragments with sequence homology to RS48 (SEQ ID NO:1) representing a central segment of the intervening sequences between RS47 (SEQ ID NO:13) and RS49 (SEQ ID NO:14). In the PCR, *M. fermentans* incognitus DNA was found in spleen, liver, brain and kidney of the *M. fermentans* incognitus inoculated animals, but not in the tissues of the control animal.

The necropsy tissues of two monkeys' livers as well as a monkey which appeared to contain the most abundant amount of *M. fermentans* incognitus DNA also stained positively with *M. fermentans* incognitus-specific rabbit antiserum. Direct examination by electron microscopy of these tissues revealed *M. fermentans* incognitus particles. Clusters of *M. fermentans* incognitus particles could most frequently be found in the cytoplasm of hepatocytes and degenerating Kuffer cells. The nearly spherical particles were 140-280 nm in diameter, had well-defined outer limiting membranes and a densely packed granular or thin tubular internal structure. Occasionally, these *M. fermentans* incognitus particles were seen in the nuclei of cells with prominent pathological changes. Some *M. fermentans* incognitus particles were also noted in the extracellular tissue matrix. The necropsy tissues of liver and apleen obtained from the control monkey which did not contain *M. fermentans* incognitus DNA did not stain with *M. fermentans* incognitus-specific antiserum and did not have similar *M. fermentans* incognitus particles.

In an attempt to reisolate *M. fermentans* incognitus from *M. fermentans* incognitus-inoculated monkeys, the peripheral blood mononuclear cells obtained from the moribund monkeys were co-cultivated with normal human peripheral blood mononuclear cells (PBMC), NIH/3T3 cells and monkey BSC cells. Supernatants of the cultures were assayed for the presence of *M. fermentans* incognitus-specific antigens and DNA once every week. The cultures were maintained for three months without evidence of *M. fermentans* incognitus growth. All the cultures were also examined for the presence of reverse transcriptase enzyme activity representing growth of retroviruses. Homogenates of necropsy tissues such as liver and spleen were also inoculated into NIH/3T3 cells and monkey BSC cells. No *M. fermentans* incognitus was successfully recovered in any of these attempts.

EXAMPLE 11

Detection of Antibodies Against *M. fermentans* incognitus

Sera from AIDS patients and from normal subjects were analyzed by the immunoperioxidase straining procedure as described by Hsu et al., supra. Briefly, persistently infected Sb51 cells or normal NIH/3T3 cells were grown in low cell density on sterile glass slides. The culture slides were fixed in acetone at room temperature for five minutes. After washing in Tris-buffered saline (TBS), pH 7.6, 0.05M, the slides were first incubated with 1% normal horse serum containing 100 g/ml avidin (Sigma) for 30 minutes, and then incubated with saturated solution of biotin (Sigma) in TBS for an additional 15 minutes. This initial step has been shown to minimize any nonspecific reaction derived from avidin-biotin-peroxidase complex (ABC). The human antisera from AIDS patients or normal subjects were then used at 1:200 dilution followed by biotin-labelled goat anti-human immunoglobulin (Tago, Burlingame, Calif.) at 1:200 dilutions and ABC (Vector Lab., Burlingame, Calif.). Each incubation step was conducted for 30 minutes with extensive washing between steps. The color reaction was developed in DAB-Ni-$H_2O_2$ solution and counterstained with methyl green. Controls for the technique were performed by omitting the secondary antibody.

Sera of patients with AIDS produced positive immunochemical reactions with these infected cells, but not with normal NIH/3T3 cells (FIGS. 12(C) and 12(B), respectively). The reaction appeared to be positive in both nuclei and cytoplasm of Sb51 cells. However, many of the nuclei stained significantly stronger than the cytoplasm. A population of smaller round cells with apparently fewer cellular processes were found to be most heavily stained. Using this assay, 23 of 24 sera from AIDS patients, whether they presented with Kaposi's sarcoma, Kaposi's sarcoma with opportunistic infections, or opportunistic infections alone, were positive (Table 3). Serum from only one AIDS patient, with both Kaposi's sarcoma and opportunistic infections, showed weak positivity. Twenty-six of 30 non-AIDS normal human sera showed no reactivity to the infected Sb51 cells. One such negative reaction is shown in FIG. 12(A). The other four sera showed mild reactivity to these cells. However, staining intensity was significantly less than that seen in the reactions of AIDS patients' sera.

TABLE 3

Prevalence of Serum Antibodies to Sb51 Cells in AIDS Patients with Various Clinical Presentations

| Subjects | Risk Group Male Homosexual | Other | Total Number | Number Positive for Antibodies to $SB_{51}$ Cells** |
|---|---|---|---|---|
| Patients with AIDS | 23 | 1* | 24 | 23 |
| Kaposi's sarcoma | 8 | | 8 | 8 |
| Opportunistic infection | 5 | 1* | 6 | 6 |
| Kaposi's sarcoma and opportunistic infections | 10 | | 10 | 9 |
| Normal | | | 30 | 0** |
| Controls | | | | |

*Female, sexual partner of bisexual males.
**Four non-Aids control sera showed mild reactivity; all the other control sera did not elicit any reaction.

EXAMPLE 12

Identification of *M. fermentans* incognitus Infected Cells in Tissues of AIDS Patients Lymph node, spleen, Kaposi's sarcoma and brain tissues from AIDS patients were fixed in Formalin and processed in paraffin sections. An immunoperoxidase assay, such as described in Example 11, was performed using antisera from mice or rabbits prepared as described in Example 8 in place of the antisera from AIDS patients. *M. fermentans* incognitus infected cells were identified in virtually all of the tissues examined. Electron microscopy was performed to confirm the infection by *M. fermentans* incognitus. Mature *M. fermentans* incognitus cells were also seen in some of the cells of the infected tissues.

EXAMPLE 13

Transmission of Cell-Free *M. fermentans* incognitus

Sb51 cells (about $2 \times 10^7$ cells) were harvested following trypsinization. The cell pellet was resuspended in 2 ml of RPMI-1640 media with 10% sorbitol (w/v). The suspension was then subjected to five cycles of freezing and thawing followed by clarification of cell debris as described above. Supernatant containing *M. fermentans* incognitus was diluted in 20 ml of RPMI-1640 with 10% bovine calf serum and filtered through a 0.22 micron filter. The filtered supernatant was added to four 75-$cm^2$ tissue culture flasks containing 70% to 80% confluent normal NIH/3T3 cells, human embryo fibroblasts or monkey BSC cells (about 5 ml of filtered supernatant were added to each flask). The infected cultures were split one week later and replenished with fresh media. The cultures were kept for an additional week. At the end of two weeks, two flasks of cells were used for the next cycle of cell-free, *M. fermentans* incognitus transmission. The other two flasks were used for DNA extraction or antigen determination. Equal numbers of normal NIH/3T3 cells, instead of Sb51 cells, were cultured in parallel through each cycle of cell-free *M. fermentans* incognitus transmission as controls.

EXAMPLE 14

Molecular Cloning and Sequencing of *M. fermentans* incognitus

DNA was phenol extracted from sucrose-banded *M. fermentans* incognitus derived from Sb51 cells which were first lysed by 0.5% sodium dodecyl sulfate (SDS) and treated with proteinase K (200 mg/ml), for 1 hour at 60° C. then 3 hours at 37° C. The alcohol precipitated DNA was treated with RNase. An EcoRI partial digest of the *M. fermentans* incognitus-enriched DNA was cloned into bacteriophage lambda charon 28. The lambda-recombinant clones were screened by differential plaque hybridization, on duplicate sets of filters, with $^{32}$P-labeled DNA derived from gradient banded M. incognitus versus that of normal NIH/3T3 cells. One clone which had specifically hybridized to *M. fermentans* incognitus DNA probe, but not to 3T3 DNA probe was identified. The insert of the positive phage clone was recloned into the EcoRI site of Bluescript KS (M13) vector (Strategene). Two cloned probes, 8.6 kilobase (psb-8.6) and 2.2 kilobase (psb-2.2) were obtained. The specificity of probes psb-8.6 and psb-2.2 was further verified by Southern blot analysis of DNA isolated from *M. fermentans* incognitus and Sb51 cells versus normal NIH/3T3 cells. To obtain sequence information, single-standed DNA of clone psb-2.2 was prepared by infection of the cells with helper phage (Bluescript instruction manual, Stragegene). About 200 base sequences starting from the EcoRI site at one end of the insert fragment of psb-2.2 were obtained, using a dideoxynucleotide sequencing method. The base sequence is set forth in SEQ ID NO:2.

EXAMPLE 15

Southern Blot Hybridization of *M. fermentans* incognitus

Restriction endonuclease cleavage of *M. fermentans* incognitus or cellular DNA was carried out with a 10-fold excess of enzymes under the conditions recommended by the manufacturer (BRL).

The enzyme digests of DNA were subjected to gel electrophoresis in 1% agarose and transferred onto nitrocellulose membranes by the Southern blot method. Each filter was prehybridized at 42° C. for at least 4 hours in 50% formamide, 5x SSC (standard saline citrate), 0.2% SDS, 20 mM Tris-HCl (pH 7.5), 2 mM EDTA, 5x Denhart's solution, and 350 microgram/ml denatured salmon sperm DNA. Each filter was then hybridized with $10^7$ cpm of $^{32}$P-labeled probe (specific activity after hybridization, the blots were washed at 60° C. in 2x SSC, 0.5% SDS for 90 minutes with three changes and then wrapped in sheets of saran wrap and exposed to Kodak XAR film at −70° C. with intensifying screens for 2–20 hours depending upon the intensity of the hybridized signals. For the reuse of the membrane, the filters were boiled in 0.1x SSC, 0.1% SDS for 10 minutes to remove the previous *M. fermentans* incognitus probe after autoradiographic exposure, and rehybridized with $^{32}$P-labeled insert fragment of psb-8.6 as previously described.

Use of the filters and results of such use are presented in Example 19 below.

EXAMPLE 16

Analysis of Taq DNA Polymerase-Catalyzed PCR Amplification Products

The amplification of selective DNA sequences by Taq DNA polymerase chain reaction is known (U.S. Pat. No. 4,683,202). Briefly, each 100 microliter reaction mixture contained 1 microgram of human tissue DNA in 50 mM KCl, 10 mM Tris-HCl (pH 8.3), 1.5 mM MgCl$_2$, each primer (RS47 (SEQ ID NO:13) and RS49 (SEQ ID NO:14)) at 1 microM, each dNTP at 200 microM, gelatin at 100 micrograms/ml, and 2 units of Taq DNA polymerase. The mixtures were heated at 94° C. for 2 minutes before the addition of DNA polymerase. The samples were overlaid with 50 microliters of mineral oil and subjected to 35 cycles of selective DNA amplification. The thermal cycle was manually conducted in three separate water baths as follows: 1 minute at 52° C., 1 minute at 72° C., and 30 seconds at 94° C. After the amplification, the reaction was stopped by addition of EDTA (final concentration, 20 mM). Ten microliter aliquots from each sample product were removed and electrophoretically fractioned in a 6% polyacrylamide gel. The fractionated DNA was electroblotted onto a Zeta membrane (Bio/Rad) at 40 volts for 90 minutes, followed by denaturation and fixation in 400 mM NaOH, 2 mM EDTA for 10 minutes at room temperature. The Zeta membrane filter was rinsed three times with 2x SSC in 20 mM Tris-HCl (pH 7.5), and air dried for 10 minutes. Prehybridization of the blots was carried out as previously described except the solution contained 4x SSC and 1% SDS. A 22-base synthetic oligonucleotide probe (RS48 (SEQ ID NO:1)), was 5' end-labeled with $^{32}$P and hybridized to the filter at 30° C. for 16 hours in the prehybridization solution containing 30% formamide. The blots were washed at 34° C. in 2x SSC, 0.5% SDS for 45 minutes with three changes and at 37° C. for an additional 2 minutes.

Use of the blots and the results of such use are presented below in Example 19.

The preferred PCR assay utilizes primers RW004 and RW005 and probe RW006 as described in Example 5.

EXAMPLE 17

DNA and Antigen Dot-Blot Analysis of *M. fermentans* incognitus

After 11 cycles of cell-free *M. fermentans* incognitus transmission, the control and *M. fermentans* incognitus infected NIH/3T3 cells of Example 13 were subjected to *M. fermentans* incognitus isolation (see Example 7, above). Ten microliter and/or twenty microliter samples from each fraction of the isopycnic sucrose gradient were first diluted to 400 microliters with PBS and then dot-blotted onto nitrocellulose paper under vacuum. The dot was blocked with 5% non-fat milk and reacted with pre-immunized or post-immunized rabbit antiserum (1:400 in PBS) at 37° C. for 3 hours. The blot was then developed with alkaline phosphatase conjugated goat anti-rabbit IgG (1:5000, in PBS) at 37° C. for 1.5 hours, followed by the addition of the substrates Nitro Blue Tetrazolium (50 mg/ml in 70% dimethylformide) plus 5-Bromo-4 Chloro Indolyl phosphate (50 mg/ml) (Promega; Madison, Wis.). Between each of the above steps, the blots were washed five times with PBS and Tween 20 (1%), five minutes each wash. For homologous DNA detection, the dotted blots were alkaline treated, neutralized and probed with $^{32}$P-labeled nick-translated psb51-8.6 or psb51-2.2 probes as previously described in Example 14.

Use of the blots and the results of such use are presented below in Example 19.

EXAMPLE 18

Immunohistochemistry for Detecting *M. fermentans* incognitus Antigens in Infected Tissues Deparaffinized sections were incubated with 10% Bovine serum albumin (Sigma Chemical Co.) in Tris-buffered saline (TBS, 0.05M Tris, pH. 7.4 saline) for 39 minutes, rinsed briefly with TBS, and covered with rabbit antisera from Example 12 (1:100 dilution). Slides were refrigerated overnight. After returning to room temperature, the slides were rinsed with 1% albumin in TBS. Slides were then covered with secondary antisera. Biotin-labelled horse anti-rabbit immunoglobulin (Vector Lab., Burlingame, Calif.) was added at a 1:200 dilution as the secondary antisera, followed by the avidin biotinylated peroxidase complex (ABC) reagent (Vector Lab., Burlingame, Calif.). Each incubation step was conducted for 30 minutes with three TBS washes between steps. The color reaction was developed in Diaminobenzidine and $H_2O_2$ substrate and counterstained with hematoxylin.

Figure 13:
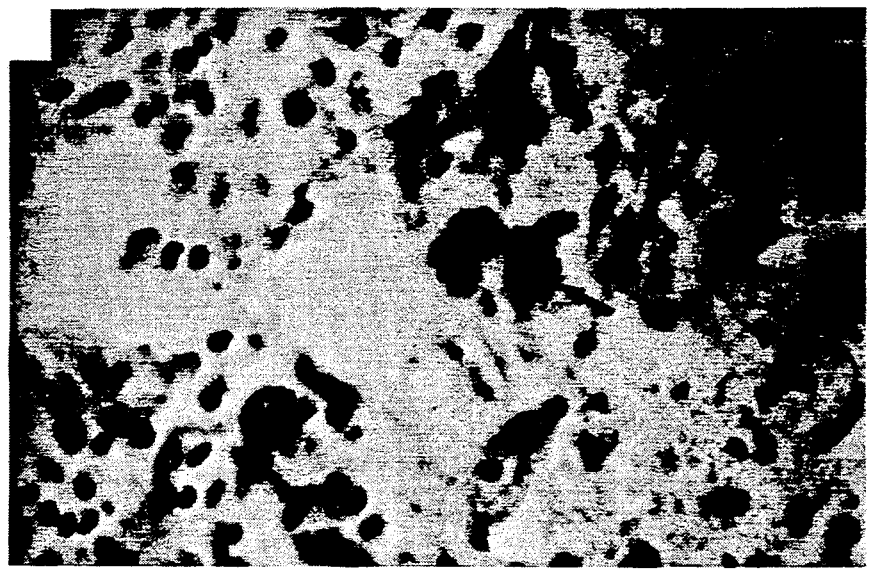
FIG. 13 shows the immunocytochemical staining of the subcapsular cortical sinus of a lymph node from a patient with AIDS.
Figure 14:
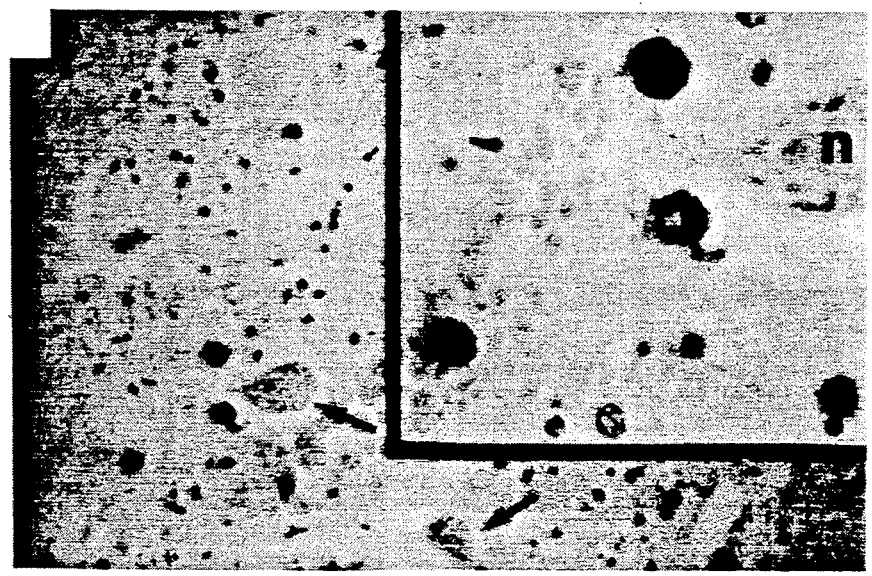
FIG. 14 shows the immunohistochemistry of the midbrain of the brain stem of a patient with AIDS.

Rabbit antiserum which reacted specifically with *M. fermentans* incognitus-Sb51 was used to stain formalin-fixed paraffin embedded lymph node and brain tissues of patients with AIDS. In the immunohistochemical study, reticuloendothelial cells or macrophages in the subcapsular sinus of a lymph node (Table 4, patient #1) were most often stained positively (FIG. 13). Brain from the autopsy of a patient with central nervous system symptoms and histopathologic evidence of subacute encephalitis without known etiology, contained many positively stained degenerating cells in lesions with diffuse infiltration of mononuclear lymphohistiocytes. Positive immunochemical reactivity was located in both nuclei and cytoplasm of swollen and disrupted cells. More peculiarly, brains from the autopsy of three other patients with CNS symptoms, but without histopathological evidence of encephalitis, also had numerous positively stained inclusion-like spherical structures (FIG. 14). The structures, most likely originating from neuroglial cells with unique pathological changes, were inconspicuous in routine hematoxylin and eosin stained sections.

DNA from two of the three brains were available for PCR study and had positive *M. fermentans* incognitus DNA information after selective gene amplification (Table 4, patient #2 and #3). The positively stained structures were more common in periventricular and perivascular areas. Normal rabbit serum (Gibco Co.) and the rabbit serum obtained before immunization with *M. fermentans* incognitus did not stain these brains. Furthermore, the immunochemical reactivity of the rabbit antiserum with either Sb51 cells or purified *M. fermentans* incognitus, but not with normal NIH/3T3 cells or spontaneously transformed NIH/3T3 cells. Eleven autopsy brain tissues obtained from non-AIDS patient were used as controls. Brains from autopsies of patients with fatal rickettsial infection, bacterial sepsis, disseminated mycobacteriosis and CNS metastatic disease served as controls. No positive reaction was observed in these control non-AIDS tissues.

TABLE 4

Clinico-Pathological Profiles of Patients with AIDS and Analysis of Specific DNA Amplification

| Subject | Clinical and/or Post Mortem Diagnosis | Tissue DNA for PCR | Lane Position in FIG. 14 | Results of DNA Amplification Analysis |
|---|---|---|---|---|
| 1. | 32 y.o.w. male homosexual, PCP candida esophagitis and cerebral toxoplasmosis | 1) Spleen<br>2) LN<br>3) Liver<br>4) Brain | A-1<br>A-2<br>A-3<br>A-4 | +++<br>+<br>++<br>− |
| 2. | 47 y.o.w. male homosexual, KS, and CMV infection, CNS syndrome | 1) Brain<br>2) Liver | A-5<br>A-6 | +++<br>+ |
| 3. | 24 y.o.w. male PCP, KS, and CNS syndrome | 1) Brain | B-1 | +++ |
| 4. | 37 y.o.w. male homosexual, PCP, and CMV infection and KS | 1) Spleen | B-2 | +++ |
| 5. | 45 y.o.w. male homosexual, KS, CMV and PCP infection | 1) KS | B-3 | ++ |
| 6. | 28 y.o.w. male homosexual with KS without OI | 1) PBMC | B-4 | − |
| 7. | 43 y.o.w. male homosexual with KS without OI | 1) PBMC | B-5 | + |
| 8. | 26 y.o.b. male homosexual with KS without OI | 1) LN | Not shown | − |
| 9. | 24 y.o.w. male homosexual with KS and myocarditis | 1) Spleen | Not shown | − |
| 10. | 31 y.o.w. male homosexual with KS, PCP, CMV and MAI infections | 1) Spleen | Not shown | + |
| 11. | Diffuse histiocytic malignant lymphoma | 1) Spleen | A-7 | − |
| 12. | Renal cell carcinoma | 1) Liver<br>2) Brain | A-8<br>A-9 | −<br>− |
| 13. | Chronic active hepatitis B. | 1) PBMC | B-6 | − |
| 14. | Metastic Ewing sarcoma in lung and liver. | 1) Ewing sarcoma | B-7 | − |
| 15. | Normal delivery placenta. | 1) Placenta | B-8 | − |

Figure 15A:
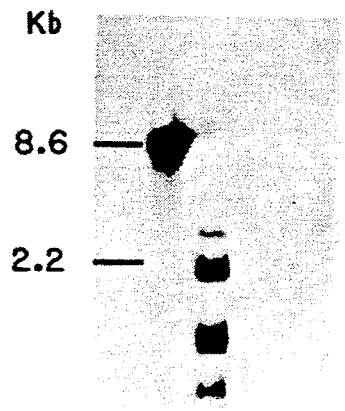
FIG. 15A shows blotted filters of DNA from Sb51 cells and control NIH/3T3 cells probed with psb-8.6.
Figure 15B:
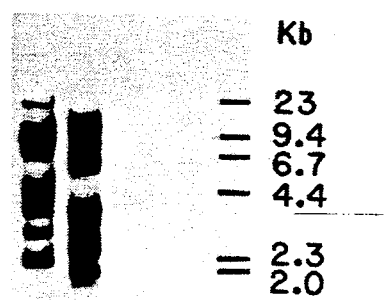
FIG. 15B shows blotted filters of DNA from Sb51 cells and control NIH/3T3 cells probed with psb-2.2.

Labels +++, ++, + and − denote high-level, intermediate level, low level and negative, respectively, for the relative intensities of the diagnostic band observed in the autoradiograms in FIG. 15.
OI - Opportunistic Infection
MAI - Mycobacterium Avium-Intracellular
KS - Kaposi's sarcoma
LN - Lymph node
PBMC - Peripheral Blood Mononuclear Cells
PCR - Polymerase-chain reaction

EXAMPLE 19

Figure 16:
FIG. 16 shows blotted filters of digested DNA from Sb51 cells, control NIH/3T3, cells, cell-free *M. fermentans* incognitus transmission in NIH/3T3 cells and DNA of partially purified *M. fermentans* incognitus probed with psb-8.6.

DNA Probes for the Direct Detection of *M. fermentans* incognitus DNA in Infected Tissues DNA was extracted from the fractions of Example 6 and digested with EcoRI enzyme. Two molecular clones carrying 8.6 kb and 2.2 kb inserts, designated psb-8.6 and psb-2.2, were obtained. When used as probes, these clones specifically hybridized to DNA of Sb51 cells (lanes 1, 2) but not to that of parental NIH/3T3 cells (lanes 3, 4) (FIG. 15). These cloned probes were used to assay infectivity of *M. fermentans* incognitus in cell cultures. The gradient banded *M. fermentans* incognitus from Sb51 cells infected normal NIH/3T3 cells after being filtered through at 0.22 micron filter. The psb-8.6 probe specifically hybridized to DNA of NIH/3T3 cells which were harvested after each round of cell-free *M. fermentans* incognitus transmission (FIG. 16). Blotted filter containing 10 ug EcoRI digested DNA from cells of sb$_{51}$ (lane 1), original, normal NIH/3T3 cells (lane 2), 7th cycle cell-free VLIA transmission control NIH/3T3 cells (lane 3), 11th cycle cell-free VLIA transmission control NIH/3T3 cells (lane 4), and 3rd cycle (lane 5), 5th cycle (lane 6), 7th cycle (lane 7), 9th cycle (lane 8), and 11th cycle (lane 9) of cell-free VLIA transmission in NIH/3T3 cells. Lane 10 contained DNA of partially purified VLIA. The blot was probed with p$^{32}$ labeled psb$_{51}$-8.6. Similarly, the psb-2.2 probe also specifically hybridized to DNA from *M. fermentans* incognitus infected NIH/3T3 cells in each cycle of passage, but not from control NIH/3T3 cells.

Figure 17A:
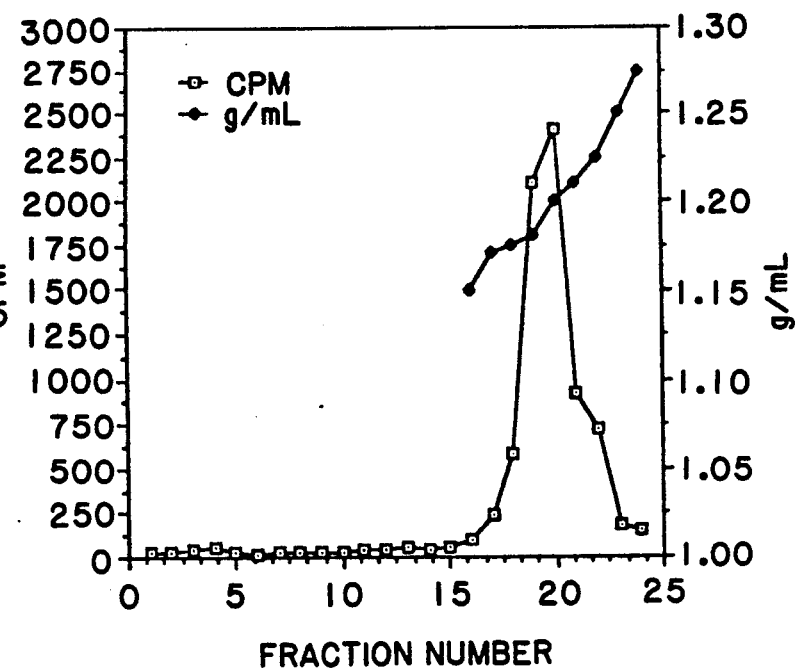
FIG. 17A shows a sucrose gradient banding of *M. fermentans* incognitus.
Figures 17B, 18A, 18B:
FIG. 17B shows DNA and antigen dot blot analysis of sucrose gradient-banded *M. fermentans* incognitus in which the blot was probed with $^{32}P$ in a labeled insert fragment of psb-8.6.
FIG. 18A shows DNA and antigen dot blot analysis of sucrose gradient-banded *M. fermentans* incognitus in which immunochemical staining using pre-immunized rabbit serum was performed.
FIG. 18B shows DNA and antigen dot blot analysis of sucrose gradient-banded *M. fermentans* incognitus in which immunochemical staining using post-*M. fermentans* incognitus immunization rabbit antisera was performed.
Figure 20A:
FIGS. 20A and 20B shows DNA amplification analysis of various tissue DNA isolated from patients with AIDS and control subjects without AIDS.
Figure 20B:
Figure 21A:
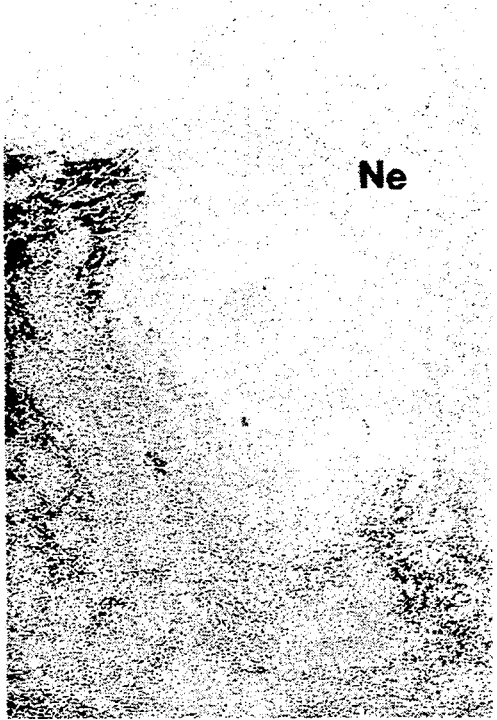
FIG. 21A shows *M. fermentans* incognitus-induced histopathological changes of fulminant necrosis in the spleen of a patient without AIDS dying of an acute systemic disease.
Figure 21B:
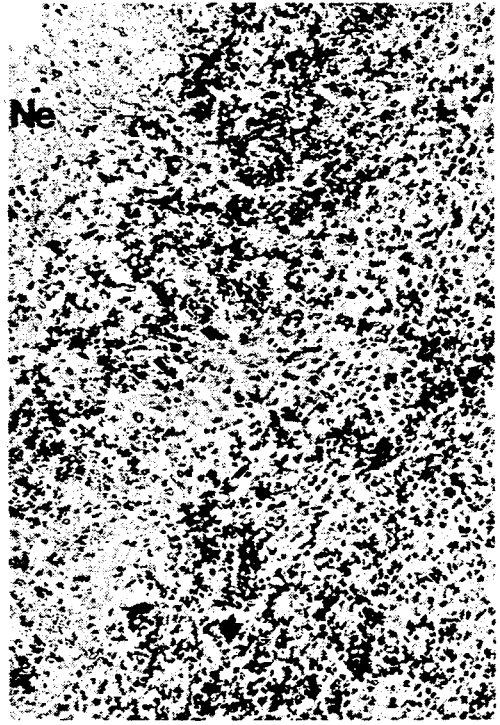
FIG. 21B shows the advancing margin of FIG. 21A.
Figure 21C:
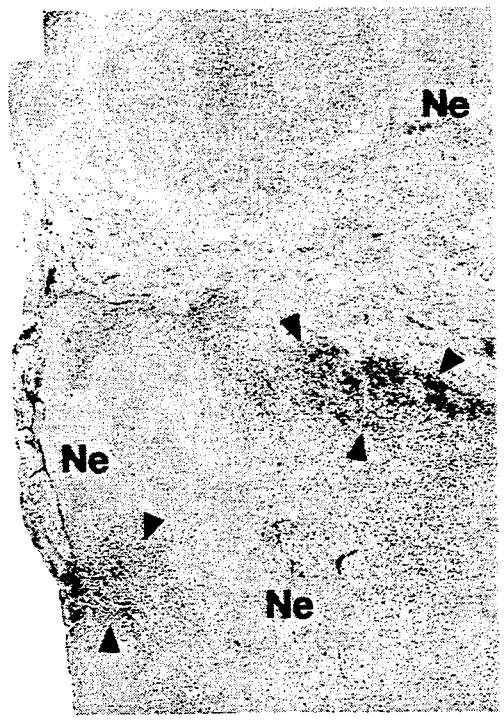
FIG. 21C shows *M. fermentans* incognitus-induced histopathological changes of fulminant necrosis in the lymph node of a patient without AIDS dying of an acute systemic disease.
Figure 21D:
FIG. 21D shows *M. fermentans* incognitus-induced histopathological changes of fulminant necrosis in the adrenal gland of a patient without AIDS dying of an acute systemic disease.
Figure 22A:
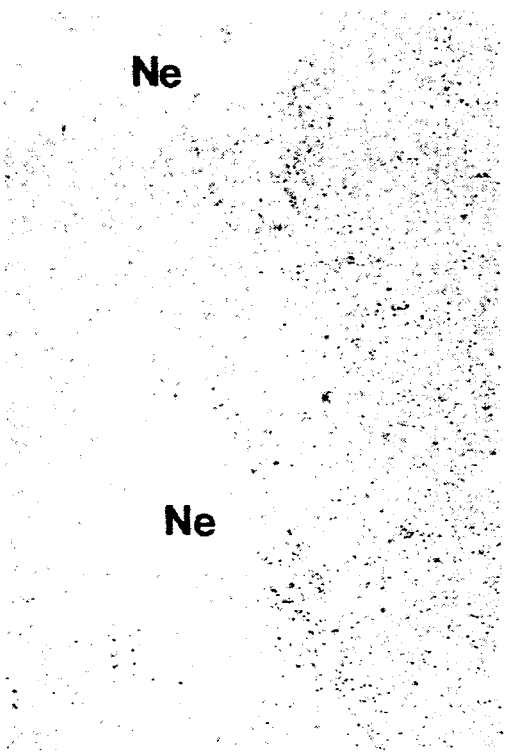
FIG. 22A shows the immunohistochemistry of *M. fermentans* incognitus-induced necrotizing lesions in the spleen using *M. fermentans* incognitus-specific rabbit antiserum.
Figure 22B:
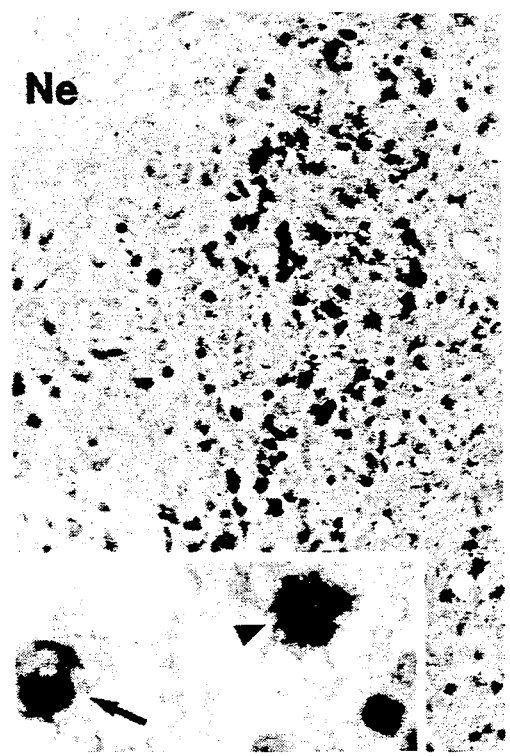
FIG. 22B shows the margin of microsis of FIG. 22A.
Figure 22C:
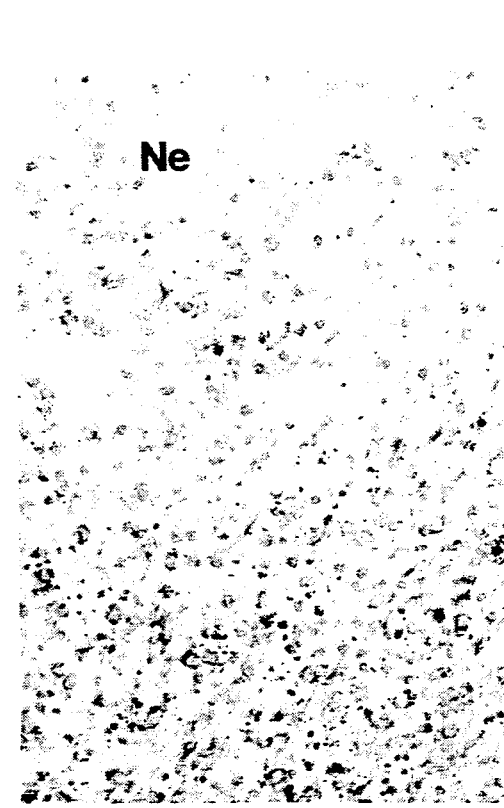
FIG. 22C shows the immunohistochemistry of *M. fermentans* incognitus-induced necrotizing lesions in the lymph node using *M. fermentans* incognitus-specific rabbit antiserum.
Figure 22D:
FIG. 22D shows the peripheral zone of necrosis of FIG. 22C.
Figure 22E:
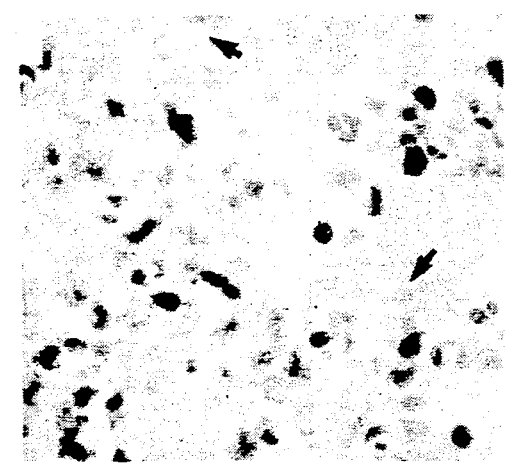
FIG. 22E shows the immunohistochemistry of *M. fermentans* incognitus-induced necrotizing lesions in the adrenal gland using *M. fermentans* incognitus-specific rabbit antiserum.
Figure 23A:
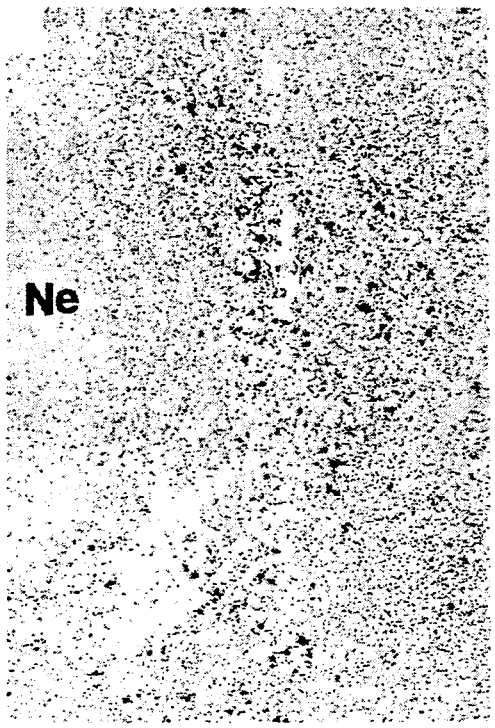
FIG. 23A shows in situ hybridization for *M. fermentans* incognitus nucleic acids in the necrotizing lesions of splenic tissue in the peripheral zone around necrosis.
Figure 23B:
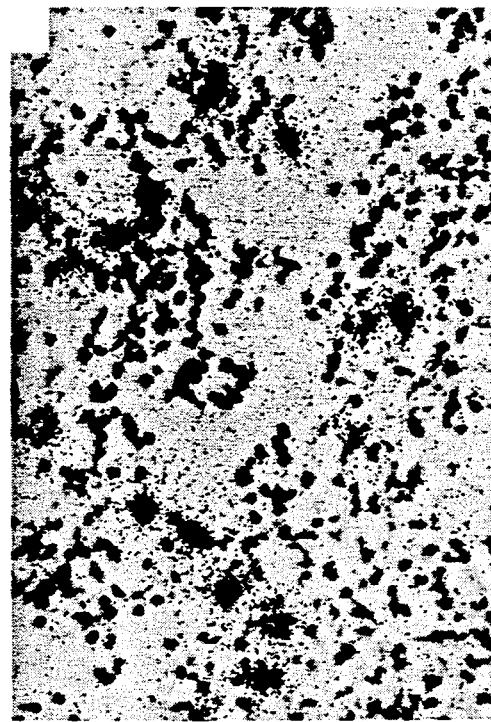
FIG. 23B shows a higher magnification of FIG. 23A.
Figure 23C:
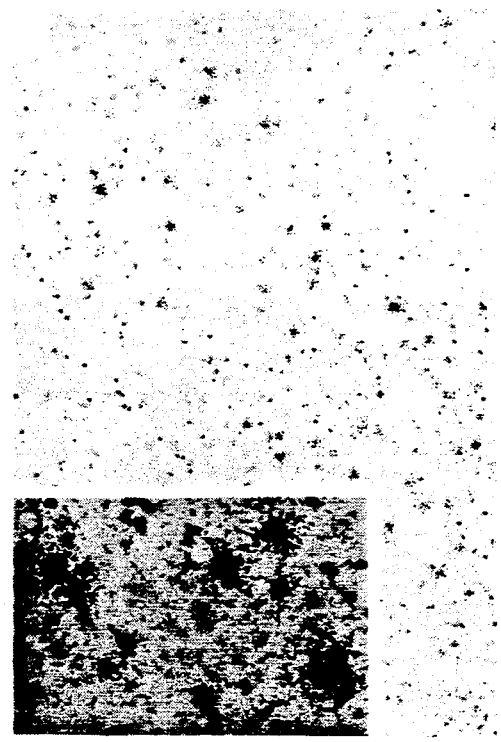
FIG. 23C shows an area of differing necrosis in splenic tissue.
Figure 23D:
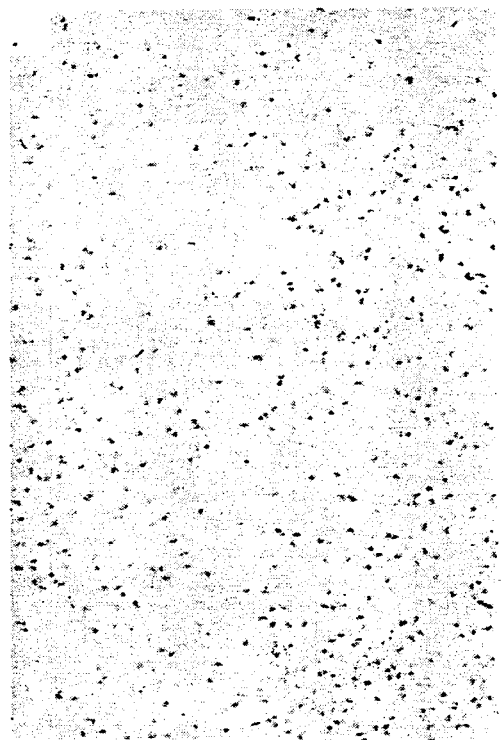
FIG. 23D shows an area of differing necrosis in splenic tissue.

The $^{32}$P-labeled psb-8.6 probe was also used for detection of *M. fermentans* incognitus in isopycnic sucrose gradients which were originally designed to band *M. fermentans* incognitus from Sb51 cells. *M. fermentans* incognitus isolated after 11 cycles of cell-free passage in NIH/3T3 cells had similar physical properties and was concentrated in the fractions of density between 1.17 and 1.20 (gm/ml) (FIG. 17A). The parallel control NIH/3T3 cultures following 11 cycles of cell-free transmission did not contain *M. fermentans* incognitus. Immunochemical staining by rabbit antiserum raised against *M. fermentans* incognitus originally isolated from Sb51 cells also revealed that *M. fermentans* incognitus was localized in these fractions (FIG. 18). FIG. 18A was stained using preimmunized rabbit serum and FIG. 18B was stained with post-VLIA immunizations rabbit antisera. Gel electrophoretic analysis of the end-labeled EcoRI or HindIII digests of the gradient-banded *M. fermentans* incognitus indicated a minimum molecular weight estimate for *M. fermentans* incognitus of greater than 150,000 bp.

To determine whether there was any significant homology of *M. fermentans* incognitus to large human DNA viral agents, Southern blot hybridizations were performed with each filter containing the restriction enzyme-treated DNA from purified *M. fermentans* incognitus, NIH/3T3, and one of the following viral genomic DNA: HSV-2, VZV, EBV, CMV, HBLV, vaccinia pox virus and mouse CMV virus. Each filter was hybridized to $^{32}$P-labeled corresponding viral DNA probe, then washed and analyzed by autoradiography. The incorporated viral probe was subsequently removed by boiling the filters before rehybridization with $^{32}$P-labeled insert fragment of psb-8.6. No cross-hybridizations of *M. fermentans* incognitus probe psb-8.6 occurred to any of the human herpesviruses, vaccinia pox virus or mouse CMV (FIG. 19). Southern blot hybridization comparing VLIA DNA to DNA from known human herpesviruses, vaccinia virus, MCMV, and HVS. Blotted filters contained DNA of VLIA (A-H, lanes 1, 2), normal NIH/3T3 (A-H, lanes 3, 4), HSV-2 (A, lanes 5, 6) VZV (B, lanes 5, 6), EBV (C, lanes 5, 6), CMV (D, lanes 5, 6), HBLV (E, lanes 5, 6), vaccinia virus (F, lanes 5, 6), MCMV (G, lanes 5, 6), and HVS pT (H, lane 5). DNA in lanes 1, 3, and 5 were digested by Eco RI: DNA in lanes 2, 4, and 6 were digested by Bam HI. HVS pT 7.4 (H, lane 5) was digested with Taq I. The $p^{32}$ labeled probes for set I were HSV-1 pHSV-106 (A), VZV pEco A (B), EBV pBam W (C), CMV pCMH-35 (D), HBLV pZVH-70 (E), vaccinia pEH-1 (F), MCMV pAMB-25 (G), and HVS pT 7.4 (H). Each blot (A-H) of set I was boiled to remove incorporated viral probe and then reprobed with $p^{32}$ labeled insert fragment of psb-8.6 (set II).

Conversely, while they hybridized to the homologous genomic DNA, one of the other viral probes hybridized to the lanes containing *M. fermentans* incognitus DNA digested with either EcoRI or BamHI. pHSV-106 originated from HSV type I hybridized to the genomic DNA of HSV type II, but not to the *M. fermentans* incognitus DNA.

A viral probe of 7.4 kb DNA (pT 7.4) from Herpesvirus saimiri (HVS) of squirrel monkeys was also examined. The viral probe did not hybridize to *M. fermentans* incognitus DNA. In some of the rehybridized filters, very weak bands resulting from incomplete removal of the previously hybridized viral probes could be noted. The weak signals served as useful reference points for the newly appearing bands obtained after rehybridization with psb-8.6 probe.

To investigate *M. fermentans* incognitus infection in humans, the recently developed, a sensitive method of selective DNA amplification, polymerase chain reaction (PCR) (U.S. Pat. No. 4,683,202) was used. (As discussed above in Example 5, it is preferred to use RW004 (SEQ ID NO:15) and RW005 (SEQ ID NO:16) as primers because a more sensitive assay is possible with these primers.) One end of the *M. fermentans* incognitus DNA in the psb-2.2 bluescript clone was sequenced. Primer pairs of synthetic oligonucleotides, designated as RS47 (SEQ ID NO:13) and RS49 (SEQ ID NO:14), with *M. fermentans* incognitus-specific sequences and Taq DNA polymerase were used for 35 reaction cycles of *M. fermentans* incognitus specific DNA amplification. The positions of RS47 (SEQ ID NO:13) and the complementary sequences of RS49 (SEQ ID NO:14) span the first 160 nucleotides of psb-2.2 *M. fermentans* incognitus DNA (SEQ ID NO:2). The amplified DNA carrying *M. fermentans* incognitus-specific genetic information revealed positive signals, when probed with $^{32}$P end-labeled synthetic oligonucleotides RS48 representing a segment of the intervening sequences between RS47 (SEQ ID NO:13) and RS49 (SEQ ID NO:14).

Ten patients with AIDS have been examined and were seropositive for HIV and had either typical opportunistic infections such as pneumocystic carinii pneumonia (PCP), toxoplasmosis, CMV infection or Kaposi's sarcoma (Table 4, subjects #1 to #10). Analysis of the amplified DNA products revealed that a diagnostic 160 bp DNA fragment and a slower migrating fragment(s) associated with a positive homologous signal, were identified in samples derived from seven of the ten AIDS patients tested. Representative results of nine positive samples and two negative samples obtained from seven AIDS patients are shown in FIG. 20. No positive signal could be detected in any of the six DNA samples derived from five control non-AIDS subjects (Table 4, subjects #11 to #15). As summarized in Table 4, patient #1 had *M. fermentans* incognitus genetic material in the lymph node, liver and spleen but not in the brain. However, both patients #2 and #3 had positive *M. fermentans* incognitus-specific DNA products in the brain samples.

EXAMPLE 20

Vaccine Containing Cells Infected by *M. fermentans* incognitus

Sixteen chimpanzees are divided into four groups. Group A is inoculated intravenously with 1 ml of the novel *M. fermentans* incognitus. Group B is inoculated with 1 ml of fluid containing $10^6$ *M. fermentans* incognitus-infected NIH/3T3 cells. Group C is inoculated with 1 ml of fluid containing $10^6$ inactivated *M. fermentans* incognitus-infected NIH/3T3 cells, and Group D is the control group and did not receive an inoculation.

All chimpanzees in Groups A and B developed symptoms of AIDS. However, none of the chimpanzees in Groups C and D developed the symptoms of AIDS. The chimpanzees of Group C are rendered immune to subsequent challenge of intravenous inoculation with 1 ml of *M. fermentans* incognitus or 1 ml containing $10^6$ *M. fermentans* incognitus-infected NIH/3T3 cells.

EXAMPLE 21

*M. fermentans* incognitus Identified In Non-AIDS Patients

Six patients from six different geographic areas who presented with acute flu-like ilnesses were studied. The patients developed persistent fevers, lymphadenopathy or diarrhea, pneumonia, and/or heart, liver, or adrenal failure. They all died in 1–7 weeks.

These patients had no serological evidence of HIV infection and could not be classified as AIDS patients according to CDC criteria. The clinical signs as well as laboratory and pathological studies of these patients suggested an active infectious process, although no etiological agent was found despite extensive infectious disease work-ups during their hospitalization.

Post-mortem examinations showed histopathological lesions of fulminant necrosis involving the lymph nodes, spleen, lungs, liver, adrenal glands, heart, and/or brain. No viral inclusion cells, bacteria, fungi, or parasites could be identified in these tissues using special tissue stains. However, the use of rabbit antiserum and the monoclonal antibodies raised against *M. fermentans* incognitus (Example 8), the pathogen shown to cause fatal systemic infection in primates (Example 10), revealed *M. fermentans* incognitus antigens in these necrotizing lesions. In situ hybridization using a $^{35}S$ labeled *M. fermentans* incognitus-specific DNA probe (Example 18) also detected *M. fermentans* incognitus genetic material in the areas of necrosis.

Furthermore, *M. fermentans* incognitus particles were identified ultrastructurally in these histopathological lesions. *M. fermentans* incognitus was associated with the systemic necrotizing lesions in these previously healthly non-AIDS patients with an acute fatal disease.

Typical areas of necrosis due to the *M. fermentans* incognitus infection of these patients are shown in FIG. 21. Most of the tissues which had massive necrosis showed only minimal lymphocytic or histiocytic response and few neutrophils (FIGS. 21A, B and C). FIG. 21A is a photomicrograph of splenic tissue (x 30.5). FIG. 21B shows the peripheral margin of necrosis of 21A (x 153). FIG. 21C is a photomicrograph of lymph node tissue (x 15.25). Occasionally, a chronic or acute inflammatory reaction could be identified in the areas of necrosis (FIG. 21D). FIG. 21D is a photomicrograph of adrenal gland tissue (x 153).

Representative samples of the immunostained tissues of these patients are shown in FIGS. 22A-D. FIG. 22A is a photomicrograph of spleen tissue (x 80). FIG. 22B is a higher magnification of the margin of necrosis of 22A (x 353). FIG. 22C is a photomicrograph of lymph node tissue (x 257). FIG. 22D is a higher magnification of cells with positive cytoplasmic staining of 22C (x 706). FIG. 22E is a photomicrograph of hemorrhagic necrosis in adrenal gland tissue (x 706). The areas which displayed the highest concentration of *M. fermentans* incognitus related antigens were often at the margin of necrosis. However, the necrotic center and peripheral unaffected areas had relatively low reactivity. Most of the positively stained cells were identified as lymphocytes or histiocytes in the lymph nodes and spleen, or reactive mononuclear cells in the liver, lungs, adrenal glands and heart.

Immunostaining of control tissues with necrotizing lesions from patients with cat scratch disease, Hodgkin's disease, malignant lymphoma, cryptococcal fungal infections and hemorrhagic splenic tissues of Hairy cell leukemia did not display a positive reaction. Serum obtained from the same rabbit before immunizaiton with *M. fermentans* incognitus antigens also failed to display a positive immunoreaction in the necrotizing lesions of the six patients.

Using a $^{35}S$ radiolabeled psb-2.2 *M. fermentans* incognitus DNA probe (Example 18), strong labeling of clusters of cells at the margins of necrosis of the affected tissues was observed. The affected tissues tested were formalin-fixed, paraffin-embedded spleen, lung, lymph node, adrenal gland liver and bone marrow. The intensity of the labeling, or the number of grains localized in the cells at the margin of necrosis was well above the level present at either the necrosis (FIGS. 23A and B). However, there were also clusters of apparently viable cells in the necrosis which were also strongly labeled (FIG. 23C). FIG. 23A shows strong labeling of cells at the peripheral zone of necrosis (x 76.5). FIG. 23B is a higher magnification of 23A (x 422). FIG. 23C shows the occasional positive labeling in an area of diffuse necrosis in the spleen (x 150). The inset of 23C is a higher magnification (x 422).

Formalin-fixed, paraffin-embedded liver and spleen tissues from a patient with pancreatic carcinoma were used as negative controls, and showed no labeling above background levels. A control probe of $^{35}S$ labeled cloning vector DNA, not containing psb-2.2 *M. fermentans* incognitus DNA did not label any of the tested tissues (FIG. 23D). FIG. 23D is the same area of FIG. 23C in the consecutive tissue section, hybridized with $^{35}S$ labeled cloning vector DNA not containing psb-2.2 *M. fermentans* incognitus DNA (x 150) (i.e., control for 23C).

Areas of the necrotizing lesions which immunostained most positively for *M. fermentans* incognitus specific antigens were examined by electromicroscopy. Particles with characteristic ultrastructural features of *M. fermentans* incognitus were directly identified in all the lesions. These particles in the areas of necrosis, morphologically resembled *M. fermentans* incognitus previously identified in Sb51 cells (Example 4) and in the tissues of experimentally inoculated monkeys (Example 10). The particles were heterogeneous in size and shape, with most particles being spherical and about 140 to 280 nm in diameter. At the margin of necrosis, the *M. fermentans* incognitus particles were located in the cytoplasm of cells with apparently no cytopathic changes, or in fragments of cytoplasm from completely disrupted cells (FIG. 24). FIG. 24 shows electron mircographs of tissues derived from areas highly positive for *M. fermentans* incognitus-specific antigens. FIG. 24A is an electron micrograph at a margin of necrosis in adrenal gland tissues (Bar=1,000 nm). FIG. 24A$_2$ is a higher magnification of 24A (Bar=100 nm). FIGS. 24B$_1$, and B$_2$ are electron micrographs of the peripheral zone of necrosis in lymph node tissue (Bar=1,000 nm). FIG. 24B$_3$ is a higher magnification of 24B$_2$ (Bar=100 nm).

Table 5, below, summarizes the profiles and histopathological findings for each of the six patients.

agar medium containing 1% Noble agar (Gibco) was dispensed into sterile plastic petri-plates (Falcon).

The cell debris from the Sb51 cells was first removed from 5 day-old culture supernatant by centrifugation at 1,500 rpm for 15 minutes. The supernatant was then pelleted in Sorvall superspeed centrifugation 10,000 rpm for 20 minutes. The particles pelleted from 50 ml of culture supernatant were resuspended in 1 ml of modified SP-4 medium and used as inoculum. The *M. fermentans* incognitus-containing suspension was 1:10 fold serially diluted with SP-4 medium and then inoculated

TABLE 5

Summary of Patient's Profiles and Histopathological Findings

| Patient | Personal Profiles | Salient clinical presentation | Duration of illness (weeks) | Tissue with necrotic lesions identified by biopsy or at autopsy |
|---|---|---|---|---|
| 1 | 29-year old black man | arthralgia, myalgia, conjunctivitis, persistent fever, hypercalcemia, liver failure (late), ARDs* (late) | 4.5 | spleen, lung |
| 2 | 33-year old white woman | persistent fever, diarrhea, generalized lymphadenopathy, abnormal liver functions, seizure (late) | 7 | lumph nodes, liver, spleen, kidneys |
| 3 | 40-year old white man | arthralgia, myalgia, sore throat, chest pain, persistent fever, malaise, diarrhea, finger numbness, comatose (late) | 3.5 | adrenal glands (bilateral), heart, brain |
| 4 | 31-year old black woman | vomiting and diarrhea, tremor, fever, epigastric and chest pain, abnormal liver functions, headache | 1.5 | liver, spleen |
| 5 | 23-year old white man | Watery diarrhea, vomiting, jaundice, arthralgia, myalgia | 3 | liver, heart |
| 6 | 33-year old black man | fever, malaise, nausea and vomiting, myalgia and weakness, liver failure and jaundice, confusion and hallucinations (late) | 1 | spleen, liver |

*ARDS - Adult Respiratory Distress Syndrome

EXAMPLE 22

Biochemical Properties and Characteristics of *M. fermentans* incognitus

In order to identify biochemical properties and characteristics of *M. fermentans* incognitus, a variety of analyses were performed on this pathogen. The analyses of biochemical properties, antigenic specificity, DNA homology and restriction pattern analysis show that *M. fermentans* incognitus is distinct from all other know species of human mycoplasma, but appears to be biologically, sereologically and molecular incognitus, a rarely isolated human mycoplasma genetically most closely related to *M. fermentans*, a rarely isolated human mycoplasma.

*M. fermentans* incognitus from culture supernatant of Sb51 cells (Example 4) was cultured in cell-free conditions using a modified SP-4 medium. SP-4 broth was prepared according to previously described procedures (Whitcomb, R. F., Methods in Mycoplasmology, Vol. I, Academic Press, Inc. pp. 147–158 (1983) and Tully, J. G. et al., Science 195, 892 (1977)), and then supplemented with 20% heat inactivated fetal bovine serum (FVS) (M.A. Bioproducts Cat. #14-901B, Lot No. 8M0320 for hybridoma). Modified SP-4 broth medium was further supplemented with 0.15 mg/ml niacin (nicotinic acid, Sigma), 0.15 mg/ml riboflavin (Sigma) 0.15 mg/ml L-arginine and 0.01 mg/ml nicotinamide adenine dinucleotide (NADH, Pharmacia). Modified SP-4 (0.2 ml) into modified SP-4 broth culture medium (2 ml).

Culture incubation and observation

All broth cultures and agar media plates were either incubated at 37° C. or 30° C. in anaerobic Gas Pak jars (BBL, Microbiology Systems, Cockeyville, Md.), candle jars or in a regular incubator. The broth media were examined daily for three weeks. Broth cultures were observed macroscopically against a white background to facilitate detection of color changes. Positive broth cultures were confirmed by subculturing 0.1 ml volumes to fresh modified SP-4 both and agar plates as soon as any color change was detected.

The surface of the agar plates was scanned with the use of a low-power objective (X4) from a standard light microscope or an inverted microscope. Positive cultures were identified by characteristic colony morphology.

For the studies of antigenic and DNA analysis, *M. hyorhinis* 9ATCC #17981), *M. orale* (ATCC #23714), *M. pneumonia* (ATC #15531), *M. hominis* (ATCC #15488), *M. genitalium* (ATCC #33530), *M. salvarium* (ATCC #23064), *M. fermentans* incognitus and *Acholeolasma laidlawii* (ATCC #23206) strains were cultured in modified SP-4 broth. *U. urealyticum* (ATCC #27618) was cultured in modified SP-4 broth supplemented with 0.03% urea.

The broth cultures appeared slightly turbid and an acidic shift in pH occurred after 10 to 14 days of incubation either at 30° C. or 37° C. Cells grew slightly better in a candle jar than in aerobic conditions; observation of a pH shift usually occurred about one day earlier.

M. fermentans incognitus could be filtered through a 220 nm membrane filter and continued to grow in the broth filtrate. The cells grown in the modified SP-4 broth were examined by electron microscopy after either ultrathin sectioning or direct negative staining. Clusters of cell wall-free microorganisms which were bound by a single triple layered membrane, showed typical plemorphic morphology of Mollicutes.

Most of the particles were spherical, but filamentous forms with occasional branching configuration, were also observed (FIG. 1A). In general, the average size of spherical M. fermentans incognitus particles in the broth cultures appeared to be much smaller than that of M. fermentans (180 nm versus 460 nm).

Figure 1C:
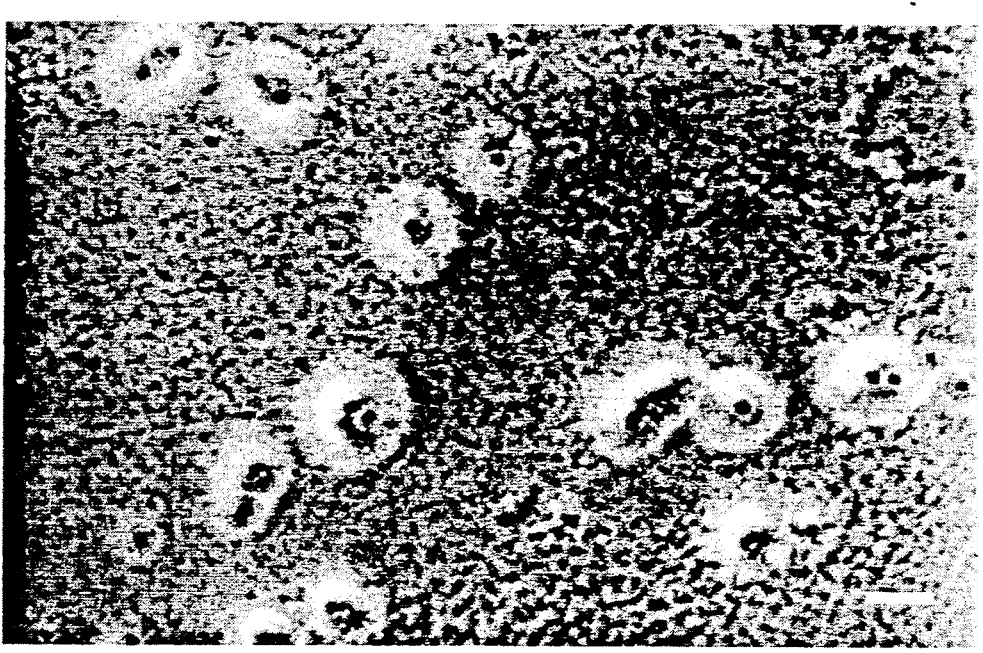
FIG. 1C shows the colony morphology of *M. fermentans* incognitus.
Figure 1D:
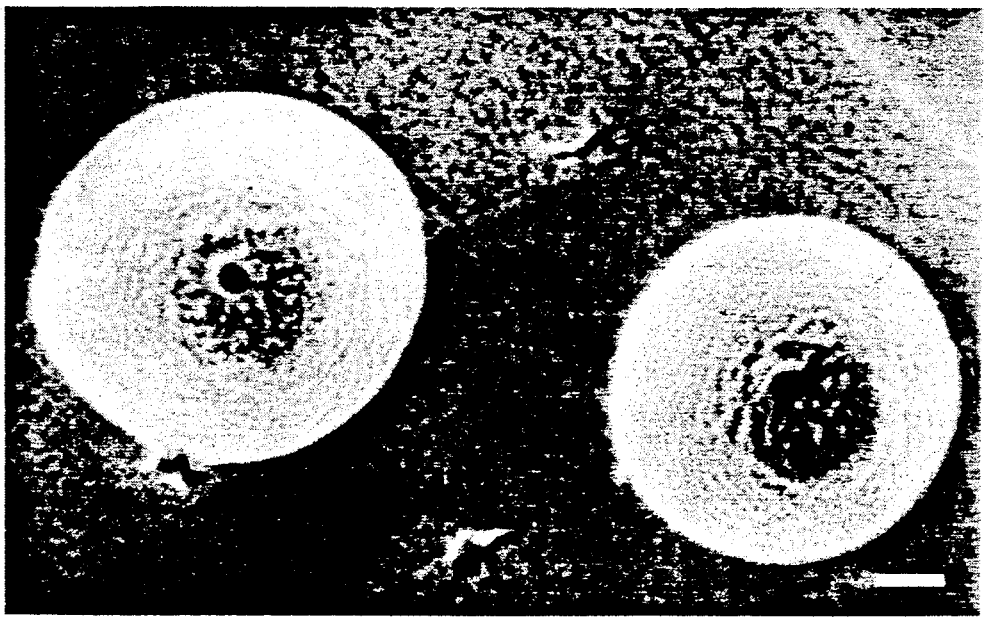
FIG. 1D shows the colony morphology of the prototype strain (PG18) of *M. fermentans*.

M. fermentans incognitus could also produce colonies on 1% Noble agar plates prepared from modified SP-4 media. Compared with some other human mycoplasmas, M. fermentans incognitus grew rather slowly and formed only small colonies (FIG. 1C). For comparison, colonies with a regular size and sharp edge formed by M. fermentans incognitus growing in a parallel modified SP-4 medium agar plate after a shorter incubation period are shown in FIG. 1D. The small colonies of M. fermentans incognitus became microscopically visible after 10 to 14 days of incubation. Most of the colonies were somewhat diffuse and irregular, and much of their growth occurred within the agar. However, under an inverted phase microscope, the small central area of the colony was found to grow even deeper into the agar and exhibited the appearance of a "fried egg" (FIG. 1C).

A single typical colony of M. fermentans incognitus was picked three times from consecutive agar plates. The cloned agent was then continuously grown and passed in the broth of modified SP-4 medium. There was no evidence of cell wall growth or conversion into a bacterium, when M. fermentans incognitus was cultured and passed in an antibiotic-free medium.

Figure 25A:
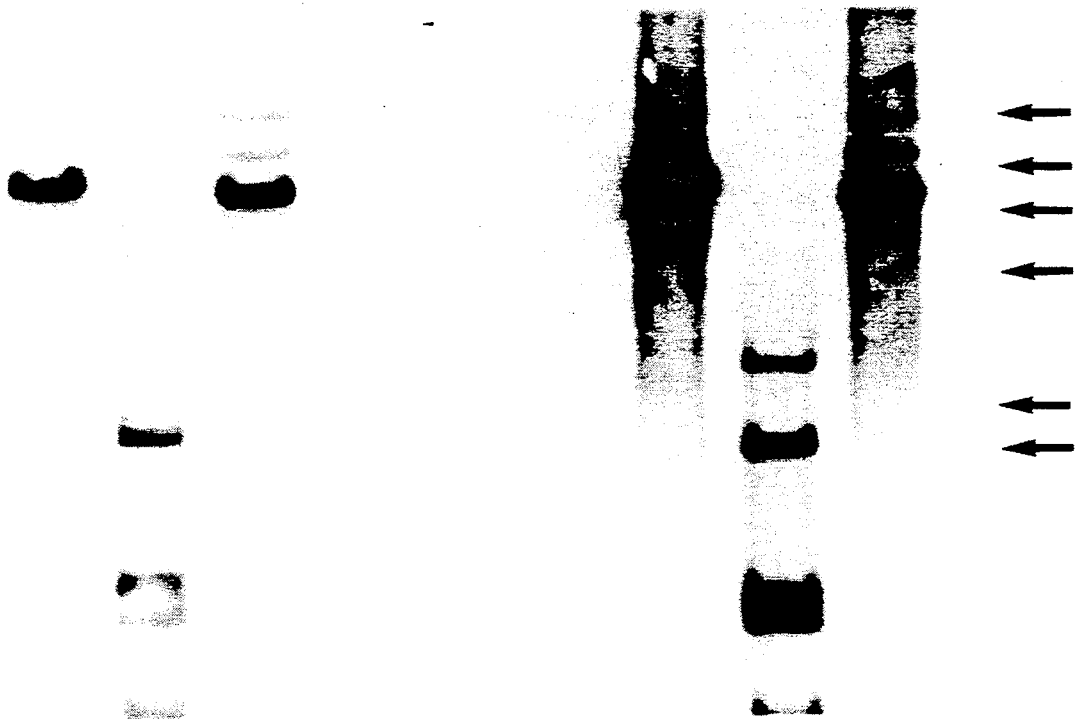
FIG. 25A shows analysis and comparison of DNA restriction patterns of VLIA and *M. fermentans* incognitus probed with psb-8.6.
Figure 25B:
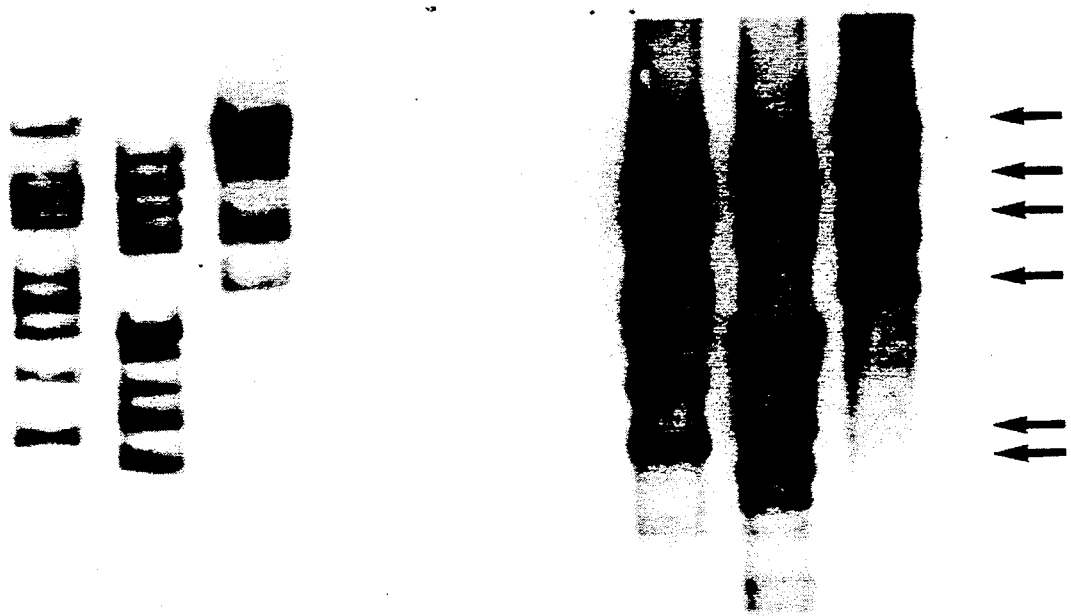
FIG. 25B shows analysis and comparison of DNA restriction patterns of VLIA and *M. fermentans* incognitus probed with psb-2.2.
Figure 26A:
FIG. 26A shows the immunohistochemistry of thymic tissues derived from patients with AIDS.
Figure 26B:
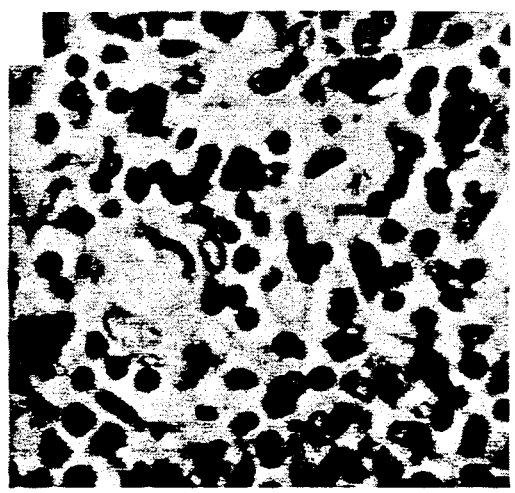
FIG. 26B is a higher magnification of FIG. 26A.
Figure 26C:
FIG. 26C is a higher magnification of FIG. 26B.
Figure 26D:
FIG. 26D shows the immunohistochemistry of thymic tissues derived from patients with AIDS.
Figure 26E:
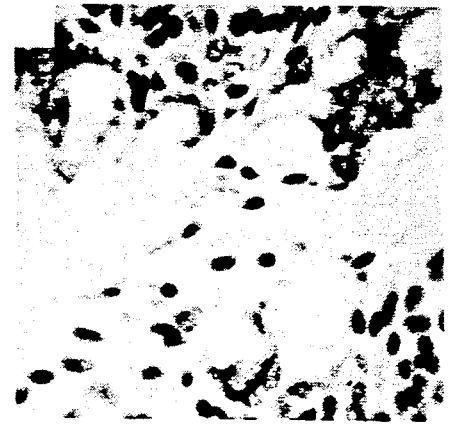
FIG. 26E is a higher magnification of FIG. 26D.
Figure 28A:
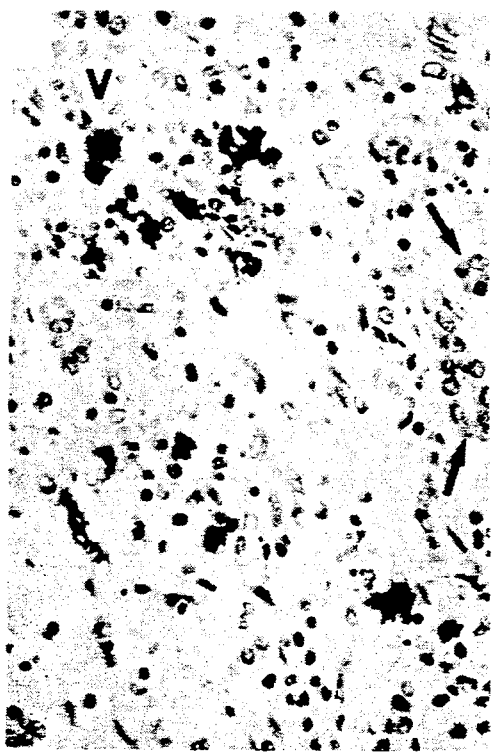
FIG. 28A shows the immunohistochemistry of livers from patients with AIDS using monoclonal antibody C42H10.
Figure 28B:
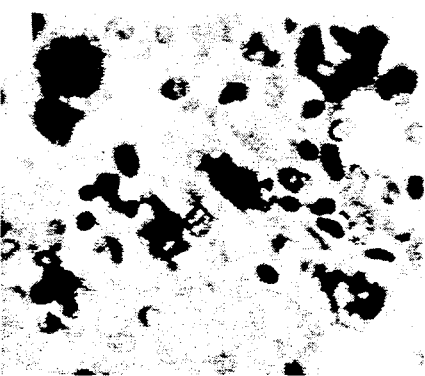
FIG. 28B shows the immunohistochemistry of livers from patients with AIDS using monoclonal antibody C42H10.
Figure 28C:
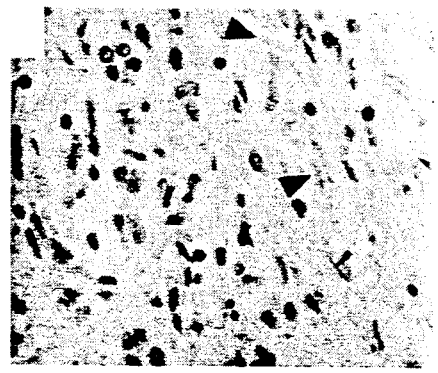
FIG. 28C shows the immunohistochemistry of livers from patients with AIDS using a non-specific monoclonal antibody.
Figure 28D:
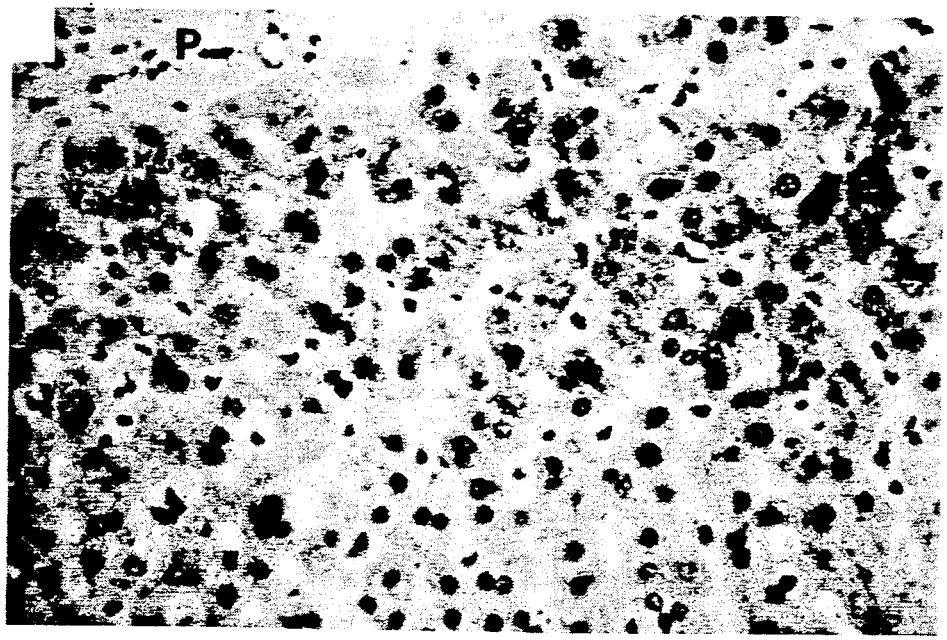
FIG. 28D shows the immunohistochemistry of livers from patients with AIDS using monoclonal antibody C42H10.

In order to verify the definite relationship between M. fermentans incognitus and what was previously identified as VLIA from Sb51 cells (prior patent application Ser. No. 265,920, filed Nov. 2, 1988), DNA from this cloned M. fermentans incognitus was isolated and compared with that of Sb51 cells containing VLIA. The DNAs were first digested with EcoRI, HindIII and PstI restriction enzymes. In the analysis of a Southern blot probed with either psb-8.6 or psb-2.2, DNA of M. fermentans incognitus grown in a cell free condition using modified SP-4 medium was identical to DNA of VLIA in Sb51 cells (FIG. 25). This tertially cloned M. fermentans incognitus was later used for all the following assays in this study.

FIG. 25 shows analysis and comparison of DNA restriction patterns of VLIA and M. fermentans incognitus. Blot (A) and blot (B) were probed with $^{32}P$ nick translated inserts of psb-8.6 and psb-2.2, respectively. Each lane in the gel contained 1 microgram of DNA from sb51 cells infected with VLIA (lanes 1,2,3) and control NIH/3T3 cells (lanes 4,5,6) or 1 nanogram of DNA from M. fermentans incognitus cultured in modified SP-4 broth (lanes 7,8,9). DNA was predigested with restriction enzymes EcoRI (lanes 1,4,7) HindIII (lanes 2,5,8) and PstI (lanes 3,6,9). Arrows indicated the positions of standard size maker 23, 9.4, 6.7, 4.4, 2.3, and 2.0 kbp, respectively.

Biochemical characterization

The tests of glucose breakdown by oxidation or fermentation, and hydrolysis of arginine or urea were performed according to standard bacteriological techniques for the characterization of mycoplasma species (Alvotto, B. B. et al., Intl. J. Systematic Bacteriology 20, 35 (1970)). Specifically, glucose, arginine and urea media were prepared by adding 10 ml of 10% (w/v) test substrate and 1 ml of 0.5% (w/v) phenol red to 74 ml of modified SP-4 broth without glucose. Each medium was adjusted using 5N HCl or 4N NaOH to the following initial pH values: glucose medium, 7.6; arginine medium, 7.0; and urea medium, 7.0. Each broth medium was filtered through a 0.22 micrometer filter and dispensed in 5 ml amounts into screw-capped tubes.

All inoculated cultures were incubated at 37° C. Anaerobic cultures were kept in Gas Pak jars (Gibco) and candle jars. Tests were read daily. A drop of 0.5 pH unit or more in the glucose tube compared with the appropriate substrate control tube constituted a positive reaction; a rise of 0.5 pH unit or more in the arginine or urea tubes compared with the appropriate substrate control tubes constituted a positive test. The pH values were read by comparison with a set of standards ranging from pH 5.6 to 8.4. Positive and negative test control organisms were:

A) Glucose breakdown (both aerobic catabolism and fermentation)
   Positive: M. fermentans and M. hyorhinis
   Negative: M. orale
B) Arginine hydrolysis:
   Positive: M. fermentans and M. orale
   Negative: M. hyorhinis
C) Urea hydrolysis:
   Positive: Ureaplasma urealyticum
   Negative: M. fermentans In comparison with other known species of human mycoplasmas, including M. pneumoniae and M. fermentans incognitus, M. fermentans incognitus appeared to be more fastidious in cultivation and did not grow in the conventional mycoplasma media (Table 5, presented at the end of this Example). Modified SP-4 (with the further addition of NADH, niacin and riboflavin) was the only medium able to support a continuous growth of M. fermentans incognitus. Serum was a necessary supplement which could not be replaced by albumin. Increased fetal bovine serum concentrations (at least up to 10 to 15% of supplement) in the modified SP-4 medium produced a growth response.

M. fermentans incognitus catabolized glucose under both aerobic and anaerobic conditions of cultivation (Table 6). M. fermentans incognitus hydrolyzed arginine and produced an alkaline shift in pH, albeit slower than M. fermentans incognitus. A prominent alkaline shift in pH occurred after an initial brief acidic shift in the M. fermentans incognitus broth culture. M. fermentans incognitus could not hydrolyze urea in the bichemical assay. The usual biological characteristics of this microorganism are apparently distinct from all the other human species but similar to M. fermentans, an other glycolytic and arginine-metabolizing mycoplasma (Kenny, G. E., Manual of Clinical Microbiology, American Society for Microbiology, Washington, D.C 4th Ed., pp.d 147-158) (1985)).

TABLE 6

Comparison of Growth and Biochemical Properties of *Mycoplasma incognitus* to Eight Other Mollicutes

|  | Species | | | | | | | | |
|---|---|---|---|---|---|---|---|---|---|
|  | AL | MA | MHO | MHY | MP | MO | UU | MF | MI |
| **(I) Ability of Growth in Different Culture Media*:** | | | | | | | | | |
| Hayflick | + | + | ND | ND | + | + | ND | + | − |
| Brain & Heart Infusion Broth | + | ND | ND | ND | ND | ND | ND | ± | − |
| Mycotrim-TC | + | ND | ND | ND | ND | + | ND | + | − |
| Heart Infusion Broth | + | ND | ND | ND | ND | + | ND | + | − |
| Arginine Broth | + | + | ND | ND | ND | ND | ND | + | − |
| Boston Broth | + | + | ND | ND | ND | ND | ND | + | − |
| A7 Agar | + | + | ND | ND | ND | ND | ND | + | − |
| SP-4 | + | + | ND | ND | ND | ND | ND | + | ± |
| Modified SP-4 (aerobic and candle jar) | + | + | + | + | + | + | +** | + | + |
| (II) Biochemical Properties: | | | | | | | | | |
| Glucose Breakdown | | | | | | | | | |
| Oxidation (aerobic culture) | ND | − | ND | + | ND | − | ND | + | + |
| Fermentation (anaerobic culture) | ND | − | ND | + | ND | − | ND | + | + |
| Arginine Hydrolysis | ND | + | ND | − | ND | + | ND | + | + |
| Urea Hydrolysis | ND | ND | ND | ND | ND | ND | + | − | − |

*All the culture media were supplemented with 20% fetal bovine serum.
**The SP-4 medium was supplemented with urea.
AL: *A. laidlawii*, MA: *M. arginini*, MHO: *M. hominis*, MHY: *M. hyorhinis*, MP: *M. pneumoniae*, MO: *M. orale*, UU: *U. urealyticum*, MF: *M. fermentans*, MI: *M. incognitus* ND: Not done in this study.

Southern blot DNA analysis

Restriction endonuclease cleavage and Southern blot hybridization using nick translated psb-8.6 nd psb-2.2 probes as well as $^{32}P$ end-labeled RS48 were described previously (Examples 13-17). A cDNA probe of E. coli r-DNA (23S and 16S r-RNA, Pharmacia Cat. #27-2508-01) was prepared with $^{32}P$ alphadeoxyadenosine triphosphate by random primer extension method (Feinberg, A. P. et al., *Anal. Biochem.* 132, 6 (1983)) using cloned Moloney murine leukemia virus reverse transcriptase (from BRL) and random primer (Pharmacia) under the conditions recommended by the manufacture of BRL. Two tenth micrograms of purified DNA isolated from cultures of each species of mycoplasa were applied to each lane for gel electrophoresis after restriction enzyme digestion.

Molecular cloning of *M. fermentans* incognitus DNA

DNA was phenol extracted from a pure culture of *M. fermentans* incognitus grown in modified SP-4 medium. The alcohol precipitated DNA was treated with Rnase. A HindIII digest of the *M. fermentans* incognitus DNA was cloned into M13 mp18 Vector (Norrander, J. et ll., *Gene* 26, 101 (1983)). The M13 mp18 recombinant clones were screened by plaque hybridization, on nitrocellulose filters, with $^{32}P$-labeled DNA derived from *M. fermentans* incognitus. One clone which had specifically hybridized to *M. fermentans* incognitus DNA probe was identified. The insert of 3.3 kilobase *M. fermentans* incognitus DNA (MI-H 3.3) was identified in the cloned probe. The cloned probe MI-H 3.3 used for Southern blot DNA analysis, had been radiolabeled with $^{32}P$ alpha-deoxyadenosine triphosphate by the chain elongation method (Lo, S-C et al., *Am. J. Trop. Med. Hyg.* 41, 380 (1989) and Messing, J. et al., *Methods of Enzymology* Vol. 101, Academic Press, Inc., pp-2078 (1983)) using the M13 universal sequencing primer (17 mer, USBC Co.) and the Klenow fragment of DNA polymerase I (USBC Co.).

Development and isotyping of monoclonal antibodies

Balb/c mice were immunized with heat inactivated (60° C. for 20 minutes) *M. fermentans* incognitus in complete Freund's adjuvant through the interperitioneal route. The mice were subsequently boosted twice at biweekly intervals, three weeks after the initial injection, with heat inactivated *M. fermentans* incognitus material in incomplete Freund's adjuvant. Four days after the last boost, the spleen was removed and the spleen cells were fused with NS1 myeloma cells using polyethylene glycol as described in Galfre and Milstein (*Methods of Enzymology* Vol. 73, Academic Press, Inc., pp. 3–46 (1981)). The fused cells were then added to 96-well microtiter plates in hypoxanthine, aminopterin and thymidine supplemented medium to eliminate unfused myeloma cells. Culture supernatants in each well were then tested for the production of antibody by using *M. fermentans* incognitus antigen-coated microtiter plates in an ELISA system.

Selected hybridomas were cloned by the limiting dilution assay in 96-well microtiter plates. Supernatants from wells demonstrating active growth were re-tested for antibody activity in the ELISA system. The specificity of the monoclonal antibodies was further crossed-checked by using *M. fermentans* incognitus, Sb51 and NIH/3T3 cell antigen-coated microtiter plates. The generation of ascites fluid was accomplished by injecting ten million hybridoma cells into the perioneal cavity of Balb/c Nu/Nu mice which had been primed with 0.5 ml of pristane, 5-7 days earlier. Ascites were harvested by inserting a 20 gauge needle and withdrawing the fluid. The material was clarified by centrifugation at 2500 rpm (300x g) for 10 minutes, and stored at −70° C. Isotyping was done using reagents from isotyping kit (Screentype, Boehringer Mannheim Biochemicals) and Bio-Dot apparatus (Bio-Rad).

Analysis of genomic DNA by restriction enzyme mapping and comparison of specific sequence homology were extremely useful in comparing different species of mycoplasma. Ten different species of mycoplasma, *M. orale, M. hyorhinis, M. pneumonia, M. ar-* ginini, *M. hominis, M. fermentans, M. genitalium, M. salivarium, U. urealyticum* and *A. laidlawii* were obtained from ATCC and cultured in the modified SP-4 broth medium with or without specific supplement. DNA isolated from *M. fermentans* incognitus and these mycoplasmas was analyzed on Southern blots and probed with $^{32}P$ labeled cloned *M. fermentans* incognitus DNA (psb-8.6, psb-2.2) or synthetic oligonucleotide (RS48).

FIG. 3 shows a comparison of DNA homology and restriction patterns between *M. fermentans* incognitus and other human mycoplasmas. The blots were probed with $^{32}P$—translated, psb-8.6 (A), psb-2.2 (B), $^{32}P$ end-labelled RS48 (C), $^{32}P$ labeled MI-H 3.3 (D) and $^{32}P$ labeled cDNA probe of *E. coli* ribosomal RNA (E). Each lane contained 0.2 microgram of EcoRI enzyme pre-digested DNA from *Acholeplasma laidlawii* (lane 1), *M. arginini* (lane 2), *M. hominis* (lane 3), *M. hyorhinis* (lane 4), *M. pneumoniae* (lane 5), *M. orale* (lane 6), *M. fermentans* incognitus (lane 7) and *M. fermentans* incognitus (lane 8). Arrows indicate the positions of standard size marker 23, 9.4, 6.7, 4.4, 2.3, and 2.0 kbp, respectively.

One additional molecular clone, carrying the 3.3 kilobase insert of *M. fermentans* incognitus DNA, designated MI-H 3.3, was also used as a probe in the study. Although some homology with psb-2.2 was observed in the *M. orale* genome (FIG. 3B), no homology with RS48 (SEQ ID NO:1), the specific DNA sequences occurring at one terminal end of psb-2.2, and no homology with psb-8.6 or MI-H 3.3 could be identified in the *M. orale* genome.

However, DNA homology with psb-8.6, psb-2.2, RS48 and MI-H 3.3 were all found in the *M. fermentans* genome (FIG. 3A, B, C, D), but, the restriction patterns revealed by these probes were different between *M. fermentans* and *M. fermentans* incognitus. No similar DNA homology could be found in any other species of mycoplasma.

Figure 3A:
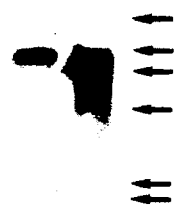
FIG. 3 shows a comparison of DNA homology and restriction patterns between *M. fermentans* incognitus and other human mycoplasmas. The samples were probed with A) pst-8.6, B) psb-2.2, C) RS48, D) MI-H 3.3, E) cDNA clone of *E. coli* rRNA.
Figure 3B:
Figure 3C:
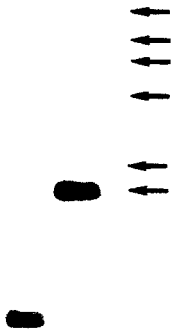
Figure 3D:
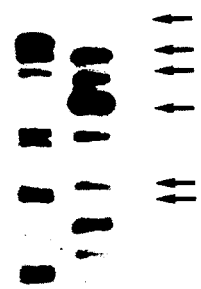
Figure 3E:
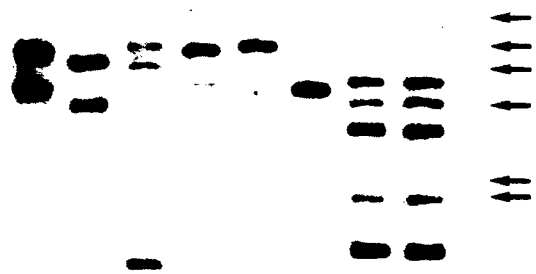

There is significant homology between the ribosomal RNA (r-RNA) genes of procaryotic mycoplasmas and those of *Escherichia coli* bacterium (Gaobel, U. B. et al., Science 226, 1211 (1984)). The same blot which had been probed consequently with RS48 and MI-H 3.3, was reprobed with $^{32}P$ labeled cDNA of *E. coli* r-RNA, after removing the previously incorporated probes by boiling the filter. This analysis of r-RNA genes revealed both a difference in numbers and size of the hybridization bands with each different species of mycoplasma tested (FIG. 3E). The characteristic restriction enzyme mappings of r-RMA genes in these Mollicutes enable the identification of related species. The EcoRI restriction pattern of r-RNA genes of *M. fermentans* incognitus and *M. fermentans* appeared to be identical (FIG. 3E) and was different from any other mycoplasma tested.

Antigenic analysis using polyclonal and monoclonal antibodies

The microorganisms harvested from each culture were washed once in phosphate buffered saline (PBS) and then resuspended in PBS. Protein concentrations of each suspension were determined using the Bio-Rad protein assay kit (Bio-Rad instruction manual). Antigenic analysis with polyclonal and monoclonal antibodies was done using the Bio-Dot microfiltration apparatus (Bio-Rad).

One hundred microliter samples from each dilution which contained decremental amounts (either 1:4 or 1:10 dilution in PBS) of proteins were dot-blotted onto nitrocellulose paper under vacuum. The blots were blocked with 5% non-fat milk and reacted with either *M. fermentans* incognitus specific rabbit antiserum (1:1000 in PBS) (Lo, S-C et al., *Am. J. Trop. Med Hyg.* 40, 215 (1989)), or *M. fermentans* incognitus specific mule antiserum (1:4000 in PBS), provided by Dr. Richard A. Dol Guidice of Frederick, Md. The titers of the rabbit *M. fermentans* incognitus antiserum and the mule *M. fermentans* incognitus antiserum had previously been determined to be 20,000 and 80,000, respectively.

The blots were then reacted with biotinylated goat antirabbit IgG (Vector) and biotinylated goat antihorse IgG (Vector), respectively. In the antigenic analysis using monoclonal antibodies, the concentration of primary antibody was adjusted to 20 fold of each monoclonal antibody titer. The titers of these monoclonal antibodies were previously determined to be D81E7, $5.1 \times 10^4$; C69H3, $2.6 \times 10^4$; F89H7, $2.0 \times 10^5$; B109H8, $2.6 \times 10^4$; F11C6, $6.4 \times 10^3$; and C24H10, $2.6 \times 10^4$. The biotinylated horse antimouse IgG or goat antimouse Igm (Vector) were used as the secondary antibodies according to the specific isotype of each monoclonal antibody. Each incubating step was conducted for 30 minutes at room temperature with three Tris buffered saline-Tween 20 (0.2%) washes between steps. The color reaction was developed in diaminobenzidine and $H_2O_2$ substrate after formation of avidin-biotin complex.

Both biological characterization and DNA homology analysis indicated that *M. fermentans* incognitus was distinct from all other species of human mycoplasmas, but closely related to *M. fermentans* incognitus. Therefore, a detailed comparison between these two species was performed by studying their specific antigenicity.

Figure 2A:
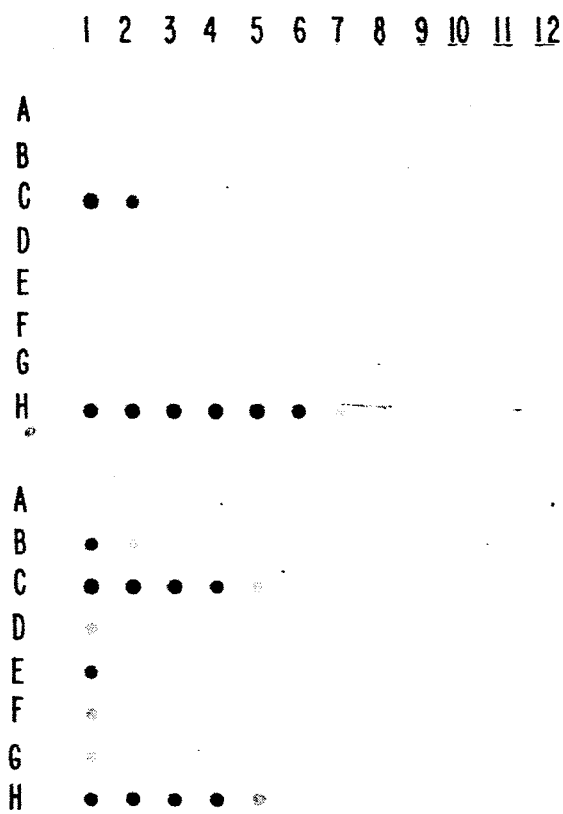
FIG. 2A shows antigenic comparison of *M. fermentans* incognitus, *M. fermentans* and other human mycoplasmas in immunoblots immunostained with rabbit antiserum raised specifically against *M. fermentans* incognitus.

Polyclonal rabbit antiserum raised originally against VLIA-Sb51 (Lo, S-C et al., *Am. J. Trop. Med. Hyg.* 40, 339 (1989)) was found to react with *M. fermentans* in addition to *M. fermentans* incognitus, but not with any other mycoplasmas examined (FIG. 2A). However, a larger amount of *M. fermentans* protein (>0.63 mg) was required to elicit the positive immunochemical reaction in this assay. The positivity of reaction quickly disappeared when the *M. fermentans* proteins were further diluted. In comparison, a 250-fold to 1000-fold lower concentration of *M. fermentans* incognitus proteins still carried a sufficient amount of antigenic determinants and exhibited positive reactions in the assay (FIG. 2A).

Figure 2B:
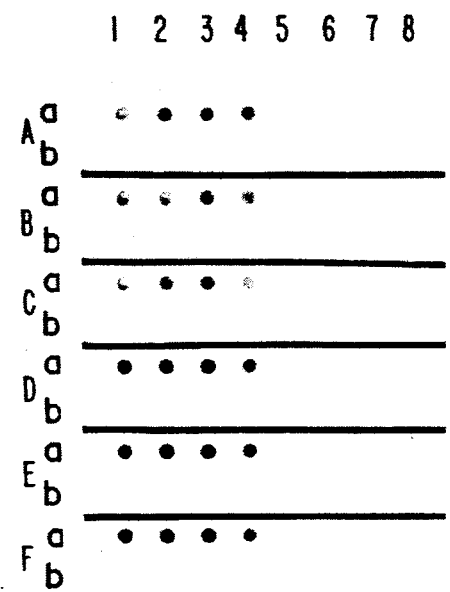
FIG. 2B shows mycoplasmas in immunoblots immunostained with mule antiserum raised specifically against *M. fermentans*.

In the parallel assay, antiserum raised specifically against *M. fermentans* also reacted intensely with *M. fermentans* incognitus (FIG. 2B). The *M. fermentans*-specific antiserum appeared to cross react with *A. laidlawii* and *M. orale* when high concentrations (10 mg) of mycoplasma proteins were dot-blotted. *M. fermentans* antiserum reacted with the antigens of *M. fermentans* incognitus proteins. Both *M. fermentans* incognitus and *M. fermentans* proteins could be diluted to 40 ng per well and still elicit a positive reaction (FIG. 2B).

FIG. 2 shows antigenic comparison of *M. fermentans* incognitus, *M. fermentans* and other human mycoplasmas in immunoblots. Upper blot (A) was immunostained with rabbit antiserum raised specifically against *M. fermentans* incognitus. Lower blot (B) was immunostained with rabbit antiserum raised specifically against *M. fermentans*. The concentration of mycoplasma protein was dot-blotted decrementally (1:4 dilution) from lane 1 (10 mg) to lane 12 (2.5 pg). Row A (*M. arginini*), row B (*A. laidlawii*), row C (*M. fermentans*), row D *M. hominis*), row E (*M. orale*), row F (*M. hyorhinis*), row G (*M. pnuemonia*), row H (*M. fermentans* incognitus). In FIG. 2 (C) row A, B, C, D and F were immunostained with monoclonal antibodies D81E7, C69H3, F89H7, B109H8, F11C6 and C42H10, respectively. The concentration of mycoplasma protein was dot-blotted decrementally (1:10 dilution) from lane 1 (10 ug) to lane 8 (1 pg). Row a (*M. fermentans* incognitus) and Row b (*M. fermentans*).

In order to examine the possibility suggested by the above results that *M. fermentans* incognitus carried additional unique antigens which are not present in *M. fermentans*, a battery of monoclonal antibodies raised specifically against *M. fermentans* incognitus were prepared. All six *M. fermentans* incognitus monoclonal antibodies obtained, many with different isotypes, were found to react only with *M. fermentans* incognitus but not with *M. fermentans* (FIG. 2C). These monoclonal antibodies also did not react with any of the other nine Mollicutes examined.

Table 7 summarizes the results of the antigenic analysis using both polyclonal and monoclonal antibodies. The results confirmed that *M. fermentans* incognitus carries additional specific antigens which could not be identified in *M. fermentans*.

nitus, but not in the other seven species of human mycoplasmas, including *M. fermentans* (FIG. 4).

FIG. 4 shows direct immunofluorescence staining of *M. fermentans* incognitus (A) and *M. fermentans* (B) using FITC conjugated monoclonal antibody D81E7 (X900).

EXAMPLE 23

Identification of *M. fermentans* incognitus Infection in Patients with Aids

Monoclonal antibodies developed against antigens from a pure culture of *M. fermentans* incognitus grown in modified SP-4 medium were used to immunohistologically identify *M. fermentans* incognitus infection in tissues of thymus, liver, spleen, lymph node or brain from 26 out of 32 patients with AIDS. *M. fermentans* incognitus infection was also identified in 2 placentas delivered by 2 patients with AIDS. The 32 patients tested were homosexuals, intravenous drug abusers or pediatric patients who had received transfusions.

*M. fermentans* incognitus specific DNA was also identified in the subject tissues using a $^{35}S$ labeled psb-2.2 DNA probe and in situ hybridization. Although *M. fermentans* incognitus was found to be both cytopathic and cytocidal, the cellular immune response and inflammatory reaction to M. incognitus infection was often atypical.

TABLE 7

| | Characterization and Comparison of Antigenicity Between *Mycoplasma incognitus* and Seven Other Mollicutes | | | | | | | | |
|---|---|---|---|---|---|---|---|---|---|
| | | Species | | | | | | | |
| ANTIBODIES | ISOTYPE | MA | AL | === | MHO | MO | MHY | MP | === |
| Rabbit antiserum Against MI | Polyclonal | − | − | − | − | − | − | − | +++ |
| Mule antiserum against MF | Polyclonal | − | ± | +++ | − | ± | − | − | +++ |
| D81E7 | Monoclonal IgM/K | − | − | − | − | − | − | − | +++ |
| C69H3 | Monoclonal IgM/K | − | − | − | − | − | − | − | +++ |
| F89H7 | Monoclonal IgM/K | − | − | − | − | − | − | − | +++ |
| B109H8 | Monoclonal IgG3/K | − | − | − | − | − | − | − | +++ |
| F11C6 | Monoclonal IgG3/K | − | − | − | − | − | − | − | +++ |
| C42H10 | Monoclonal IgG1/K | − | − | − | − | − | − | − | +++ |

Labels +++, +, ± and − denote the relative positivity of immunostaining results in FIG. 4. MA: *M. argini*, Al: *A. laidlawii*, MF: *M. fermentans*, MHO: *M. himinis*, MO: *M. orale*, MHY: *M. hyorhinis*, MP: *M. pneumoniae*, MI,: *M. incognitus*

Direct immunofluorescense examination

Monoclonal antibody was purified from ascites fluid by high-salt precipitation and gel chromatography using Sephacryl-200 (Campbell, D. H. et al., *Method in Immunology* 2d Ed., W. A. Benjamin, Inc., p. 198 (1970)). Labeling of the purified antibody with fluorescein isothiocyanate (FITC) was done using the method described by Rinderknecht (*Nature* 193, 167 (1962)). The broth culture suspensions were directly smeared on the slides. The slides were air dried, fixed in 70% acetone, 30% methanol and stored at 4° C. The slides were directly immunostained with FITC conjugated monoclonal antibody and examined under a fluorescent microscope.

In this study of direct immunofluorescence staining, the FITC probe conjugated to the purified *M. fermentans* incognitus monoclonal antibodies which again revealed positive staining only in *M. fermentans* incog- Patient orofiles All 34 AIDS patients were selected according to CDC criteria (JAMA 258, 1143 (1987)). All patients were seropositive for HIV-related antigens. Unless specified below, all the patients belonged to the homosexual high risk group.

Four thymic tissues, 10 livers from patients with unexplained abnormal liver function tests, 8 spleens and 8 brains from patients with clinical CNS symptoms obtained at autopsy as well as 2 biopsied lymph nodes were used. Histopathological studies using special tissue stains did not reveal any bacterial, fungal or viral infectious agent in these tissues. All tissues obtained at autopsy and biopsy were previously fixed in 10% buffered formalin and embedded in paraffin blocks. Tissues of non-AIDS control subjects were also obtained from 10% formalin fixed and paraffin embedded blocks of autopsy tissues.

Immunohistochemisty and in situ hybridization

Deparaffinized and frozen section slides were incubated with 10% bovine serumalbumin (Sigma Chemical Co.) in phosphate-buffered saline (PBS, Gibco Co., pH 7.4 saline) for 30 minutes, rinsed briefly with PBS, and covered with monoclonal antibodies (1:600 dilution).

Slides were kept refrigerated overnight. After returning to room temperature, the slides were rinsed with 1% albumin in PBS. The slides were then covered with secondary antisera. Biotinylated horse anti-mouse IgG (H&L) or biotinylated goat anti-mouse IgM (H&L) (Vector Lab., Burlingame, Calif.) was added at 1:200 dilution in PBS as secondary antisera and followed by the avidin biotinylated peroxidase complex (ABC) reagent (Vector Lab, Burlingame, Calif.). Each incubation step was conducted for 1 hour with extensive washing between steps. The color reaction was developed in DAB-$H_2O_2$ substrate and counterstained with hematoxylin.

Development of *M. fermentans* incognitus-specific monoclonal antibodies (C42H10, and D81E7) has been described previously in Example 21. In parallel, non-specific mouse monoclonal antibodies (IgM, MOPC 104E and IgG$_{2b}$K, MOPC 141, Sigma) or monoclonal antibody (ascites) raised specifically against herpes virus (IgG$_1$, MCA 255, clone R1, Bioproducts) were used as the primary antibodies and served as negative controls in immunohistochemistry. Detailed procedures of preparation of $^{35}$S radiolabeled psb-2.2 probe and in situ hybridization on formalin-fixed and paraffin embedded tissues were also described previously (Lo, S-C et al., *Am. J. Trop. Med. Hyg.* 41, 380 (1989)).

Electron microscopy

To retrieve formalin-fixed paraffin-embedded tissues for ultrastructural examination, immunohistochemistry positive areas of tissue sections on glass slides were circled. These exact area were then matched and identified on each individual paraffin block. Tissues of 1 to 2 mm in diameter were punched out from the blocks and deparaffinized in xylene. Processing of these tissues for E. M. studies were previously described in detail (Lo, S-C et al., *Am. J. Trop. Med. Hyg.* 41, 380 (1989)).

RESULTS

Thymus

Many patients with AIDS suffer a profound deficiency in cell mediated immunity. It is well known that development of competent T-cell immunity is thymus dependent. Therefore, four thymic tissues available from patients with AIDS were examined for possible *M. fermentans* incognitus infection. Two of the thymic tissues were described grossly at autopsy as involuted thymus, one from a two year old and the other from a eight year old. Both of these pediatric patients contracted AIDS from blood transfusions.

The other two thymuses were derived from adult AIDS patients and the autopsy reports contained no specific gross tissue description. Immunohisto-chemical studies, using *M. fermentans* incognitus-specific monoclonal antibodies, showed positive immunoreaction in all four thymic tissues. Both mononuclear lymphohistiocytes and epitheloid cells were stained positively (FIG. 26).

FIG. 26 shows the immunhoistochemistry of thymic tissues derived from patients with AIDS. FIG. 26A is a low-magnification photograph of a thymus immunostained by *M. fermentans* incognitus-specific monoclonal antibody (C42H10) (X71.5). FIG. 26B is a higher magnification of the positively immunostained lymphohistiocytes in the junction between cortex and medulla shown in 26A, left curve arrow (X715). FIG. 26C is a higher magnification of the positively immunostained lymphohistiocytes in the septal interstitial tissues in 26A, right curve arrow (X715). FIG. 26D is a low-magnification photograph of a thymus from another AIDS patient (X126.5). FIG. 26E is a higher magnification of the positively immunostained cells in 26D (X142).

Electron microscopic examination of the areas of the thymus with significant positive immunoreaction showed ultrastructurally many particles resembling mycoplasma. The particles were located both intracellularly in the cytoplasm of lymphohistiocytes (FIG. 27 A, B) and apparently free-growing extracellularly (FIG. 27 C, D). FIG. 27 shows an electron micrograph of an AIDS thymus immunostained positively for *M. fermentans* incognitus-specific antigens. FIG. 27A is an electron micrograph of mononuclear lymphohistiocytes with many intracytoplasmic electron dense mycoplasma-like particles (arrows) (N is the nucleus and bar represents 100 nm). FIG. 27B is a higher magnification of the electron dense mycoplaslma-like particles in the cytoplasm of a mononuclear cell shown in 27A (P is a polysomal structure and bar represents 100 nm). FIG. 27C is an electron micrograph of many mycoplasma-like particles found both inside the membrane bound cytoplasmic vesicle (arrow heads) and also extracellularly in the interstitial tissue (arrows) (N is the nucleus with degenerating changes, Bar represents 100 nm). FIG. 27D is a higher magnification of the extracellular mycoplasma-like particles. The outer limiting membrane of some particles (arrows) can be identified (Bar represents 100 nm).

Most of the nearly spherical particles measured 100-300 nm. No cell wall was associated with these particles. However, a prominent halo with a clear space surrounding each of these intracellular particles was commonly noted.

Occasional cells exhibited cytopathological changes and even appeared to be necrotic. However, most cells in these tissues were morphologically unremarkable. There was no tissues reactive process and/or an inflammatory reaction identified.

Liver

Ten livers from patients with AIDS who had unexplained abnormal liver function tests were examined. Work-ups for both hepatitis B and A infections were negative in these patients.

Four of these ten livers were positive by immunohistochemistry using *M. fermentans* incognitus-specific monoclonal antibodies. Histopathology of these four livers varied from no pathological changes except mild periportal infiltrates of lymphohistiocytes (two) to fulminant hepatocyte necrosis without any inflammatory reaction (one) and patchy areas of hepatocyte necrosis associated with prominent acute and subacute inflammation (one). The positively immunostained cells in these livers were the infiltrating inflammatory cells and the hepatocytes with or without any evidence of cytopathological changes (FIG. 28). Some areas of sinusoidal space lined by Kupffer cells were also stained positively.

FIG. 28 shows the immunohistochemistry of livers derived from patients with AIDS, using monoclonal antibody C42H10. FIG. 28A is a photomicrograph at a portal area in an AIDS liver with patchy areas of necrosis. Prominent infiltrates of chronic inflammatory cells and proliferation of bile ducts (arrows) are identified (X390). FIG. 28B is a higher magnification of the positively immunostained cells in 28A (X780). FIG. 28C is the same portal area shown in 28A in a subsequent tissue section immunostained by a nonspecific monoclonal antibody with the same isotype IgCl/k. Hemosiderin pigments (arrow heads) are noted (X390). FIG. 28D is an immunohistochemical photomicrograph of another AIDS liver. No necrosis or histopathological changes other than mild infiltrates of chronic inflammatory cells in the portal area (P) can be found in the liver (X390).

Figure 29A:
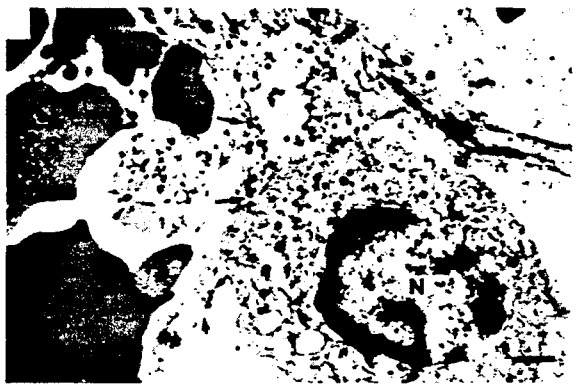
FIG. 29A shows an electron micrograph of AIDS liver immunostained positively for *M. fermentans* incognitus-specific antigens at low magnification.
Figure 29B:
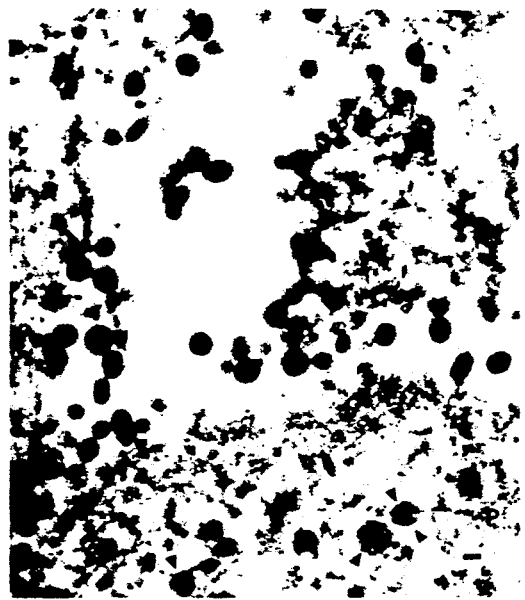
FIG. 29B is a higher magnification of FIG. 29A.
Figure 29C:
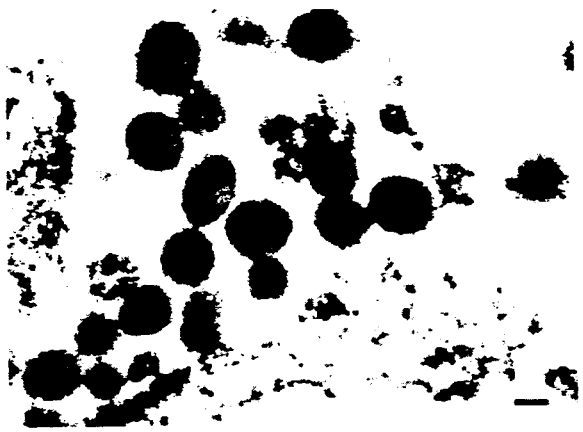
FIG. 29C is a higher magnification of FIG. 29B.
Figure 29E:
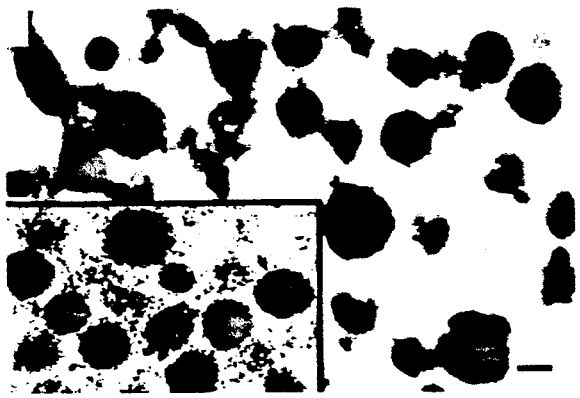
FIG. 29E is a higher magnification of FIG. 29D.
Figure 29D:
FIG. 29D shows an electron micrograph of AIDS liver immunostained positively for *M. fermentans* incognitus-specific antigens at low magnification.

The areas of liver showing positive M. fermentans incognitus- specific antigens were also retrieved from the original paraffin blocks for ultra structural examination. Microorganisms with typical mycoplasma morphology were identified in all four livers. These mycoplasma-like microorganisms could be found intracellularly in the cytoplasms of mononuclear lymphohistiocytes, Kupffer cells and hepatocytes. Many of these microorganisms also lined up extracellularly along the walls of sinusoids (FIG. 29). For comparison, an electron micrograph of M. fermentans incognitus in the liver of a silvered leaf monkey, experimentally infected with this pathogen (Example 9) is shown in the insert of FIG. 29E.

Figure 33A:
FIG. 33A shows electron microscopy of an AIDS patient's placenta immunostained positively for *M. fermentans* incognitus specific antigens showing Hofbauer cell.
Figure 33B:
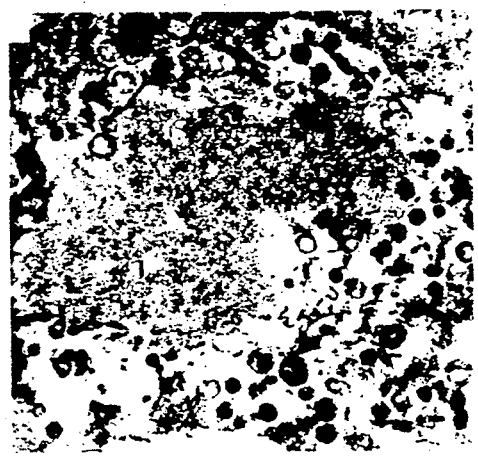
FIG. 33B shows electron microscopy of an AIDS patient's placenta immunostained positively for *M. fermentans* incognitus specific antigens showing Hofbauer cell.
Figure 33C:
FIG. 33C shows electron microscopy of an AIDS patient's placenta immunostained positively for *M. fermentans* incognitus specific antigens showing stronal connective tissue.
Figure 33D:
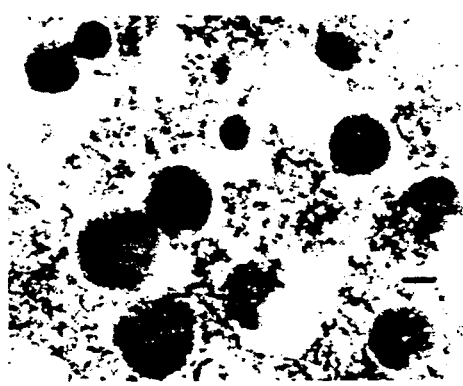
FIG. 33D shows electron microscopy of an AIDS patient's placenta immunostained positively for *M. fermentans* incognitus specific antigens showing stronal connective tissue.
Figure 33E:
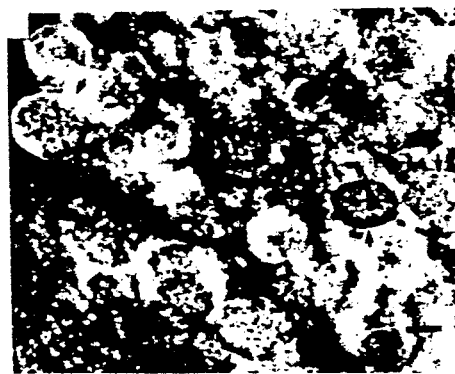
FIG. 33E shows electron microscopy of an AIDS patient's placenta immunostained positively for *M. fermentans* incognitus specific antigens showing stronal connective tissue.

FIG. 29 shows an electron micrograph of AIDS liver immunostained positively for M. fermentans incognitus-specific antigens. FIG. 29A is an electron micrograph of a periportal area of an AIDS liver with adjacent necrosis. N is the nucleus of a mononuclear lymphohistiocyte. R is red blood cells in the small vessel and the bar represents 500 nm. FIG. 29B is a higher magnification of the mycoplasma-like microorganisms found in the empty extracellular space and lining along the outer surface of the lymphohistiocyte shown in 29A. Many intracellular particles (arrow heads) can also be identified and are difficult to differentiate with the extracellular particles (P is the polysomal structure and the bar represents 1200 nm). FIG. 29C is a higher magnification of the mycoplasma-like microorganisms lining the outer surface of the lymphohistiocyte (Bar represents 100 nm). FIG. 29D is an electron micrograph of another AIDS liver which showed no evidence of histopathological changes except mild portal infiltrates of chronic inflammatory cells (N is the nucleus and the bar represents 400 nm). FIG. 33E is a higher magnification of the mycoplasma-like particles shown in 29D. The insert shows M. fermentans incognitus in 2% glutaldehyde fixed liver of experimentally infected silvered leaf monkey at the same magnification (Bar represents 100 nm).

Lymph node and spleen

Two lymph nodes surgically removed from AIDS patients showed reactive changes with follicular hyperplasia and foci of sinus histiocytosis. No areas of necrosis were identified. Positive immunochemical reactions were seen primarily within the endothelial cells lining the lymphatic sinus or the mononuclear lymphohistiocytes found in the sinus. Both nuclei and cytoplasm were stained positively. The typical staining patterns were similar to the results presented previously, using polyclonal rabbit antiserum (Lo, S-C et al., Am. J. Trop. Med. Hyg. 40, 213 (1989)).

Sections from four of six autopsy spleens without pathological changes stained positively with M. fermentans incognitus-specific monoclonal antibody. Mononuclear histiocytes and reticular cells in periarterial regions, mononuclear, reticular cells and lymphocytes in areas of red pulps were the positive cells which often revealed varying degrees of swelling or disruption. The strongly-stained nuclei and cytoplasm resembled inclusion bodies in the immunochemical reaction. Positively stained cells could also be identified in two additional splenic tissues with areas of prominent necrosis. The positive immunochemical reaction was concentrated at periphery of the necrosis (data not shown).

Characteristic ultrastructures with morphological features typical of mycoplasma were identified in all four spleens (including two with necrosis) and two lymph nodes which were retrieved for electron microscopy.

Brain

More than 60% of patients with AIDS are reported to have abnormal central nervous system (CNS) symptoms (Navaia, B. A. et al., Ann. Neurol. 19, 517 (1986)). Since most AIDS patients have serological evidence of HIV infection, the CNS diseases in these patients with AIDS have been called HIV encephalopathy.

Eight brains from patients with AIDS who had prominent clinical symptoms of CNS diseases without histopathological diagnosis of a specific infection in the brains at necropsy were examined. Two of these 8 brains had lesions of fulminant necrosis and karyorrhexis associated with both acute and subacute inflammations. Both of these brains were from intravenous drug abusers with AIDS. One of the other brains had subacute encephalitis with mononuclear cell infiltration but no necrosis. The remaining 5 brains showed only atrophy, gliosis and occasional microglial nodules without evidence of necrosis or inflammation.

All 3 brains with histopathological evidence of acute or subacute encephalitis stained positively for M. fermentans incognitus-specific antigens. FIG. 30 shows the positive immunostaining of the acute and subacute inflammatory cells in the periphery of a necrotic brain lesion.

Figure 30A:
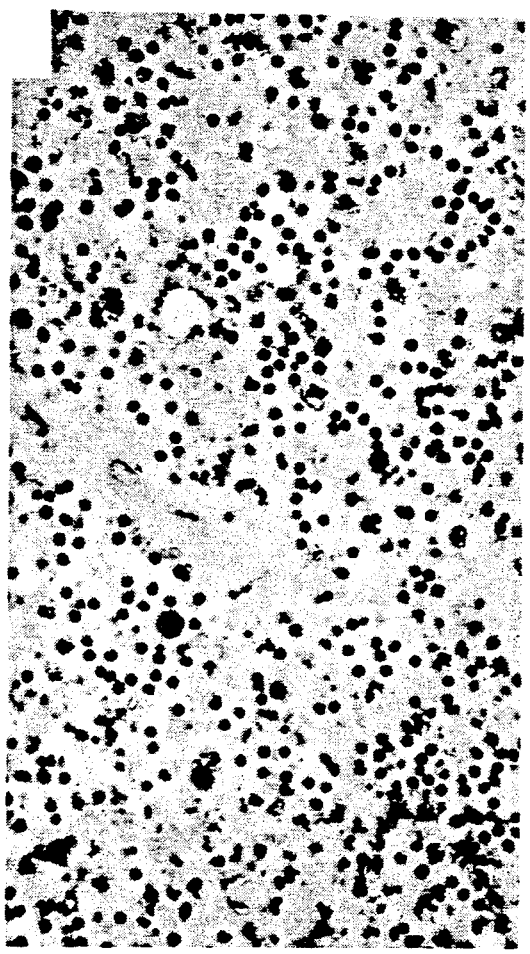
FIG. 30A shows the immunohistochemistry of a brain derived from a patient with AIDS using monoclonal antibody C42H10.
Figure 30B:
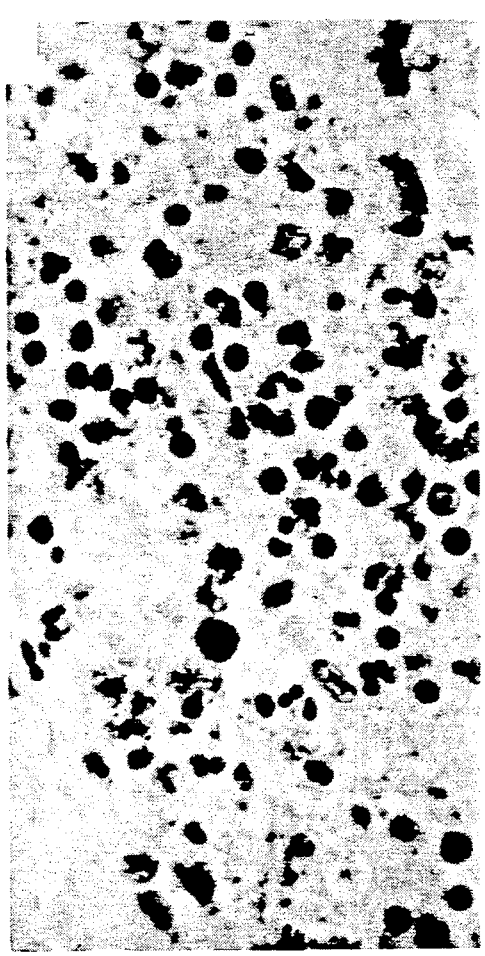
FIG. 30B shows the immunohistochemistry of a brain derived from a patient with AIDS using monoclonal antibody C42H10.
Figure 30C:
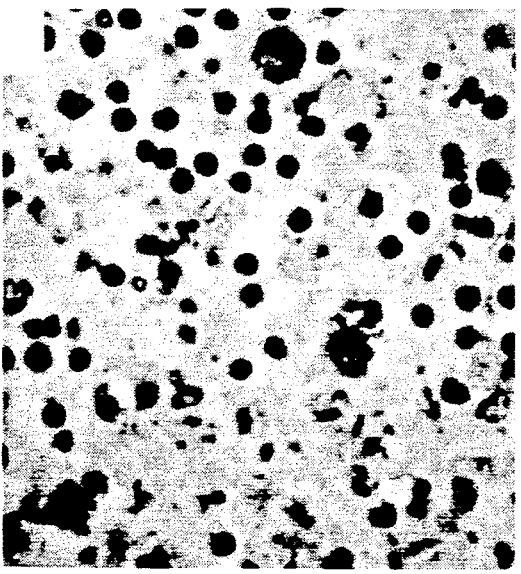
FIG. 30C shows the immunohistochemistry of a brain derived from a patient with AIDS using a non-specific monoclonal antibody.
Figure 30D:
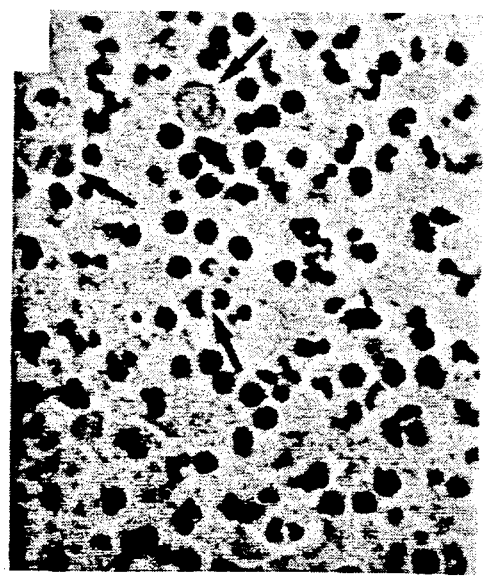
FIG. 30D shows the immunohistochemistry of a brain derived from a patient with AIDS using monoclonal antibody C42H10.
Figure 31A:
FIG. 31A shows electron microscopy of CNS encephalopathy AIDS brains which were histologically unremarkable but immunostained positively for *M. fermentans* incognitus-specific antigens.
Figure 31B:
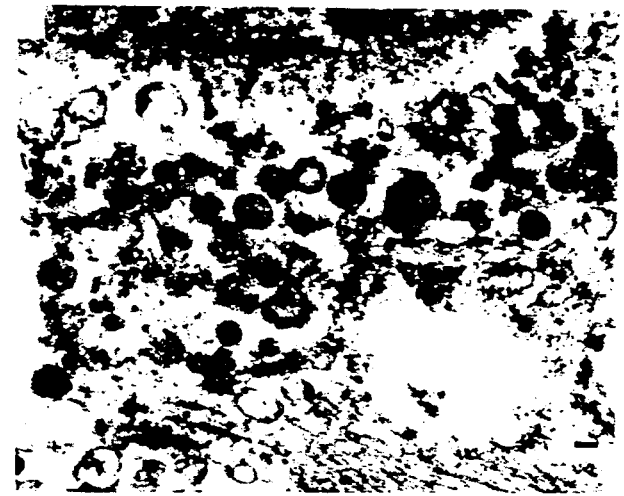
FIG. 31B is a higher magnification of FIG. 31A.
Figure 31C:
FIG. 31C is a higher magnification of FIG. 31B.
Figure 31D:
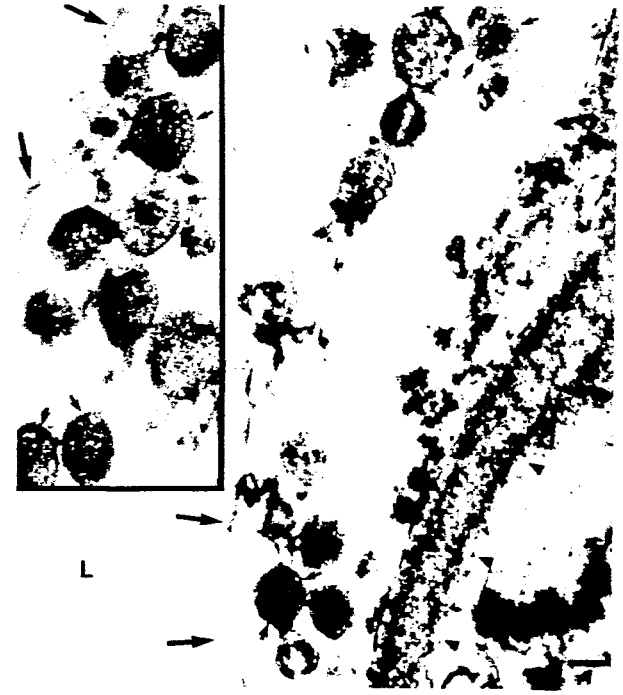
FIG. 31D is a higher magnification of FIG. 31C.
Figure 32A:
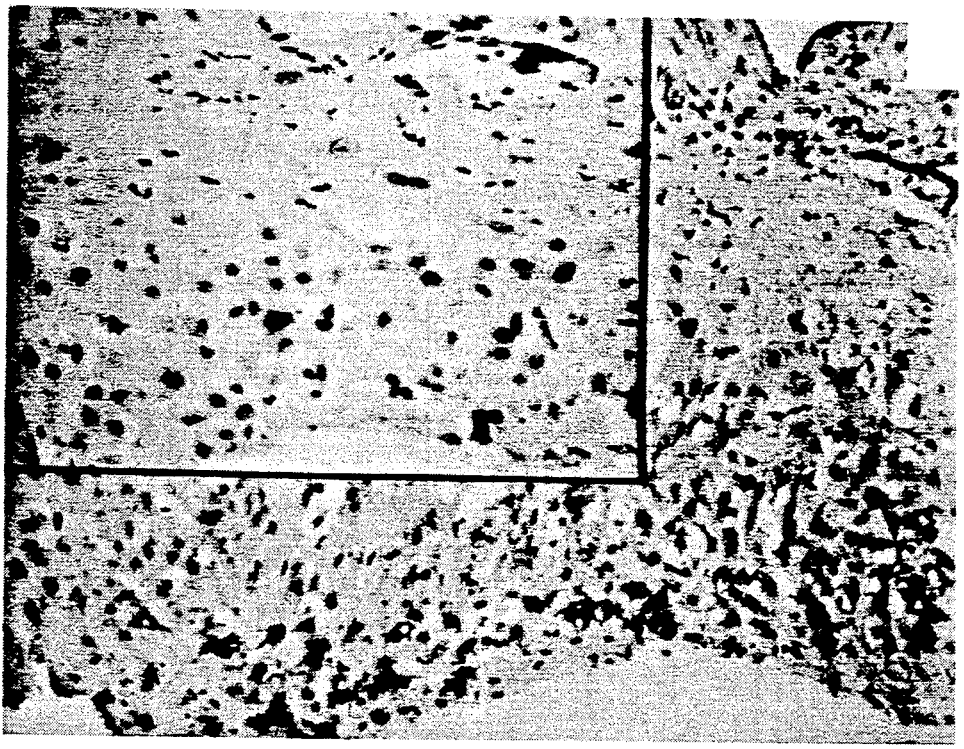
FIG. 32A shows the immunohistochemistry of a placenta delivered by a patient with AIDS using monoclonal antibody C42H10.
Figure 32B:
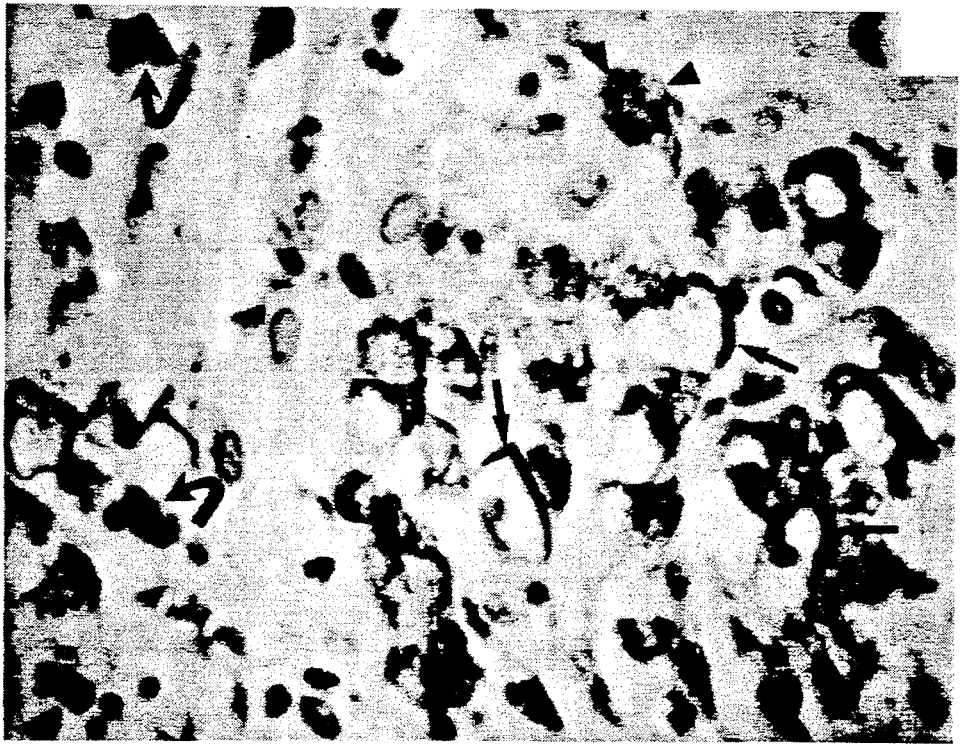
FIG. 32B is a higher magnification of FIG. 32A.

FIG. 30A is a photomicrograph of the periphery of a necrotic cerebellar lesion immunostained positively by M. fermentans incognitus-specific monoclonal antibody (C42H10) (X390). FIG. 30B is a higher magnification of the periphery of the lesion in 30A and shows both acute and subacute inflammatory cells immunostained positively (X780). FIG. 30C is also a higher magnification of the positively stained cells in 30A (X780). FIG. 30D is a photomicrograph of the same periphery area of the necrotic lesion immunostained by a non-specific monoclonal antibody with the same isotype IgG1/k. Cells with prominent cytopathological changes and disruption (arrows) are evident (X780).

Furthermore, three of the 5 brains showing no evidence of inflammation or necrosis also revealed positive immunostaining. The positively stained cells showed degenerating changes, and often became inclusion body-like structures in the gray and white matter. The patterns and characteristics of positive immunohistochemical staining identified in these histologically unremarkable brains were comparable to those previously reported, using rabbit polyclonal antiserum (Lo, S-C et al., Am. J. Trop. Med. Hyg. 40, 213 (1989)).

Figure 34A:
FIG. 34A shows in situ hybridization for *M. fermentans* incognitus nucleic acid in liver from patients with AIDS.
Figure 34B:
FIG. 34B shows in situ hybridization for *M. fermentans* incognitus nucleic acid in liver from patients with AIDS.
Figure 34C:
FIG. 34C shows in situ hybridization for *M. fermentans* incognitus nucleic acid in spleen from patients with AIDS.
Figure 34D:
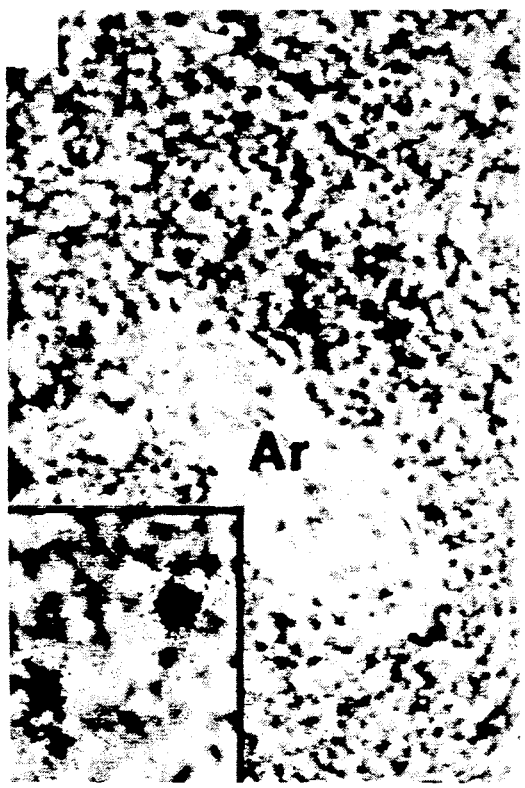
FIG. 34D shows in situ hybridization for *M. fermentans* incognitus nucleic acid in spleen from patients with AIDS.

Ultrastructural confirmation of *M. fermentans* incognitus infection in these 6 brains which immunostained positively for *M. fermentans* incognitus-specific antigens was also performed. Many electron-dense particles with features of mycoplasma organisms were identified extracellularly positively for *M. fermentans* incognitus-specific antigens was also performed. Many electron-dense particles with features of mycoplasma organisms were identified extracellularly or in the cytoplasm of mononuclear lymphohistiocytes located in the periphery of necrosis. Clusters of particles with morphological features of mycoplasma could also be identified in the encephalopathy AIDS brains showing positive immunostaining but with no evidence of necrosis and inflammation (FIG. 31). Some of the particles had prominent outer membranes. For comparison, the electron micrograph of *M. fermentans* incognitus with an apparent outer limiting membrane identified in cytoplasm of Sb51 cells in culture is shown in the insert of FIG. 31D.

FIG. 31A is an electron micrograph of mycoplasma-like particles (arrows) clustered together in the hippocampus. F is a bundle of neuroglial filament and N is the nucleus of a mononuclear cell (Bar represents 100 nm). FIG. 31B is a higher magnification of the mycoplasma-like particles shown in 31A. The outer limiting membrane (small arrows) of some particles is prominent. (Bar represents 100 nm). FIG. 31C is a higher magnification of the same particles. FIG. 31D is a high magnification electron micrograph of mycoplasma-like particles found in the brain stem from another AIDS patient (large photo to right). The typical particles with well-preserved outer membrane (small arrows) are shown in an endothelial cell. Cytoplasmic membrane (large arrows) of the endothelial cells and basement membrane (arrow heads) of the vessel can be identified. L is the lumen of the vessel. The insert shows an electron micrograph of VLIA (*M. fermentans* incognitus) originally identified in the cytoplasm of sb51 cells, at the same magnification. The unit membrane of *M. fermentans* incognitus (small arrows) is prominent in the well fixed (2% glutaldehyde) and well preserved culture specimen. Cytoplasmic membrane (large arrows) of the sb51 cell is also identified (Bar represents 200 nm).

Placentas

Two placentas delivered at full term by two women with AIDS were available for study. The babies were reported to be normal at birth. However, no follow-up was available.

Histopathological examination showed occasional infiltrate of acute inflammatory cells in the chorionic plates in one of the placentas. The second placenta was histologically unremarkable. The special histopathological stains did not reveal any pathogens in either of the two placentas. Immunohistochemical study of both placentas, using *M. fermentans* incognitus-specific monoclonal antibodies C42H10 and D81E7, exhibited positive immunoreaction in areas of Hofbauer cells and stomal connective tissues in the chorionic villi (FIG. 32). Some decidual cells in the stratum basalis were also stained positively.

FIG. 32 shows the immunohistochemistry of a placenta delivered by a patient with AIDS. FIG. 32A is a photomicrograph of placenta tissue positively immunostained by a *M. fermentans* incognitus-specific monoclonal antibody (C42H10). The insert shows the same placental area in a subsequent tissue section immunostained by a non-specific monoclonal antibody with the same isotype IgG1/k (X 195). FIG. 32B is a higher magnification of the positively immunostained cells shown in 32A. The cytoplasm (arrow heads) or the surface of vacuolated cells (arrows) more often reveals positive reaction. Cells showing cytopathological changes with both nuclei and cytoplasms are positively stained (curve arrows) may resemble atypical inclusion bodies (X780).

Electron microscopic examination of the Hofbauer cells and connective tissues in the positively stained chorionic villi revealed numerous particles characteristic of mycoplasma (FIG. 33). Some particles identified in the Hofbauer cells were probably in membrane bound vesicles. Many microorganisms, with a wide variation of size, shape and electron density, appeared to focally colonize in the stomal connective tissue (FIG. 33). A prominent halo with a clear space surrounding each of these particles was often noted. No accompanying acute inflammatory cells or other reactive process was identified. Some apparently better preserved particles exhibited recognizable outer limiting membranes. However, many of the mycoplasma-like particles did not have definite outer unit membranes; they showed only an electron dense internal matrix with a fine granular configuration.

FIG. 33 shows electron microscopy of an AIDS patient's placenta immunostained a positively for *M. fermentans* incognitus specific antigens. FIG. 33A is an electron micrograph of a Hofbauer cell containing may mycoplasma-like particles in the cytoplasm. Some particles are apparently in the membrane bound cytoplasmic vesicles (arrows). N is the nucleus and I is a cytoplasmic inclusion body (Bar represents 800 nm). FIG. 33B is a higher magnification of the mycoplasma-like particles. Both spherical electron dense particles (arrow heads) and flask shape particles (arrows) typical for mycoplasma organisms are found to colonize in the stomal connective tissue (Bar represents 1000 nm). FIG. 33D is a higher magnification of the mycoplasma-like particles shown in 33C. Typical electron dense internal matrix with fine granular configuration of these particles is shown. Occasional particles contain recognizable outer membrane (arrows) (bar represents 100 nm). FIG. 33E shows many of the particles are also those of less electron dense but with granular appearing internal matrix. These particles often have more prominent outer limiting membrane (arrows) (Bar represents 100 nm).

Detection of *M. fermentans* incognitus specific genetic material

*M. fermentans* incognitus DNA was identified in the tissues of thymus, liver and spleen from patients with AIDS as well as in the placentas delivered by two women with AIDS using the $^{35}S$ labeled psb-2.2 probe. FIG. 34 shows positive labeling with grains heavily concentrated in cells of livers and spleen. Cytological and/or histological identification of the specific "types" of cells containing *M. fermentans* incognitus DNA, revealed that they were the Kupffer cells and hepatocytes in the liver showing minimal histopathological changes (FIG. 34A), the infiltrating lymphoid cells and histiocytes in portal tracts of another liver (FIG. 34C), and the lymphocytes in periarteriolar lymphoid sheaths (white pulp) of spleen (FIG. 34D).

In parallel, $^{35}S$-labeled M13 mp 19 vector DNA which did not contain *M. fermentans* incognitus DNA, did not elicit any positive signals in the consecutive sections from these tissues (FIG. 34B). Five tissues of spleen and liver from three patients who died of non-AIDS conditions were used as negative controls and also did not reveal any evidence of positive signals.

FIG. 34 shows in situ hybridization for *M. fermentans* incognitus nucleic acid in liver and spleen from patients with AIDS. FIG. 34A shows cells with strong labeling (arrows) are seen in an AIDS liver with no histopathological abnormally after hybridization with $^{35}$S labeled psb-2.2 DNA. Higher magnification (insert) reveals dense clusters of grains over individual hepatocytes or Kupffer cells (X240, X770). FIG. 34B is the same area of 34A in the consecutive tissue section, hybridized with $^{35}$S-labelled cloning vector DNA not containing *M. fermentans* incognitus DNA (X270). FIG. 34C shows lymphocytes and histiocytes with positive labeling seen in the portal tract infiltrated with mononuclear inflammatory cells in the liver of another AIDS patient (X770). FIG. 34D shows lymphocytes with strong labeling seen in the periarteriolar lymphoid sheath of the spleen. The central arteriole (Ar) is identified. The insert shows higher magnification of heavily concentrated grains over the lymphoid cells in this white pulp (X350, X770).

Kidney

Renal tissues from 203 patients who died of AIDS as defined by the Centers for Disease Control criteria were selected for study. The patients lived in various geographic locations including the continental United States (US), Puerto Rico (PR), Haiti, and Africa. The different racial backgrounds included in this study were white, black, Hispanic, and Oriental. Risk activities for AIDS were varied and included intravenous drug abuse (IVDA), homosexual contact, heterosexual contact, and history of blood transfusion. The patients had a wide range of opportunistic infectious agent including *Pneumocystis carinii, Toxoplasma gondii, Candida albicans, Cryptococcus neoformans, Histoplasma capsulatum, Mycobacterium avium-intracellulare, M tuberculosis,* cytomegalovirus, herpes simplex virus, and others.

Of the 203 total patients comprising this study, 20 patients had renal histopathologic changes characteristic of AIDS-associated nephropathy (AAN). Group B consisted of 15 patients selected from the remaining 183 who had no significant clinical or pathologic evidence of renal disease. These patients were matched as closely as possible with Group A patients in terms of the distribution of age, gender, race, and risk activities which Sections of kidney from the autopsies of 203 patients with AIDS, as well as renal tissues from the five (Group C) controls, were examined by conventional light microscopy. Special stains, including periodic acid-Schiff, Grocott's methenamine silver, Ziehl-Neelsen, mucicarmine, Masson's trichrome, and Brown and Hopps, were obtained to evaluate glomerular and tubular morphology as well as to document the presence of various opportunistic infections. For the 20 cases of AAN, glomerular, tubular, and interstitial changes were semi-quantitatively graded and recorded.

Renal tissues from 15 of the 20 patients from Group A and all of the tissues from Groups B and C were evaluated using monoclonal antibodies (MABs) against *M. fermentans* incognitus as described above.

Formalin-fixed, paraffin-embedded sections of kidney were immunochemically stained with MABs against the incognitus strain, as previously described. Specific areas of positive staining were circled (approximately 1 mm in diameter) and removed from the matched paraffin tissue blocks. Tissues were then deparaffinized and processed as described above. After embedding all tissues in epoxy resin, semi-thin sections were cut and stained with alkaline toluidine blue for histologic analysis. The thin sections of the selected blocks were stained with lead citrate and uranyl acetate and examined by electron microscopy.

Light Microscopy

For all 20 cases of AAN, the earliest recognizable glomerular change consisted of relative and actual dilatation of Bowman's space, with concomittant capillary tuft wrinkling, compression, or complete collapse (FIG. 1a). Bowman's spaces often contained finely granular proteinaceous material which was also present in the lumens of adjacent proximal convoluted tubules. The subsequent glomerular change was "early" segmental or global glomerulosclerosis, as evidenced by hypertrophy and vacuolization of visceral epithelial cells and capillary endothelial cells, increased amounts of mesangial matrix material in either a segmental or global distribution, and small protein droplets within epithelial cells and Bowman's space. The most advanced glomerular change was fully evolved ("late") segmental and global sclerosis. In the latter case, glomerular tufts were transformed to round "sclerotic balls," sometimes surrounded by a rim of hypertrophic epithelial cells. In this advanced stage, homogeneous, dense cast material often filled the dilated Bowman's spaces and contiguous tubular lumens. The peripheral edges of these casts had scalloped borders, created by side by side "holes" in the cast material adjacent to tubular epithelial cells.

Tubular changes usually paralleled glomerular changes. In early stages, tubular epithelial cells with cytoplasmic swelling contained many protein droplets. Subsequently, tubular lumens became dilated and contained protein droplets or granular proteinaceous material, as well as degenerated sloughed epithelial cells. In later stages, tubules showed microcystic dilatation and were filled by dense cast material. Epithelial cells within such tubules were flattened from compression by the large proteinaceous casts. In all cases, variable degrees of interstitial edema and mononuclear cell inflammation were present. Special tissue stains did not reveal any evidence of infection with bacteria, fungi, or mycobacteria in these kidneys.

Sections of renal tissue from the 15 group B patients showed minimal structural abnormalities including focal mild mononuclear cell infiltration of the interstitium, rare mononuclear cells within glomerular capillary lumens, and occasional hyaline casts. Renal tissue from three of the five group C patients also demonstrated normal histology, renal tissue from the remaining two showed changes consistent with reflux nephropathy and moderate to marked nephrosclerosis, respectively.

Immunohistochemistry

For all of the 15 group A patients, there was positive staining by M incognitus-specific MABs in several locations including glomerular endothelial and epithelial cells, capillary basement membrane, tubular epithelial cells, tubular casts, and mononuclear interstitial cells. Although all cases had positive staining for antigens of this microorganism in the above locations, six cases showed more prominent positivity in glomerular epithelial and endothelial cells, while nine cases had greater positivity in tubular epithelium and casts. Particularly intense staining could often be seen in partially degenerated cells within the casts, or within the amorphous cast material itself.

Kidney tissues from group B patients showed positive staining for incognitus strain-specific antigens only within occasional mononuclear interstitial cells. These mononuclear cells were either histiocytes or lymphocytes. None of the cases in this group demonstrated positivity within the glomerulus or tubules. The renal tissues of group C patients showed no staining for incognitus strain-specific mycoplasmal antigens in any locations.

Electronmicroscopy

Electron microscopic examination of tissues from the particular areas highly positive for incognitus strain-specific antigens revealed structures strongly resembling mycoplasmal organisms in various locations in all 15 group A cases.

In seven patients, mycoplasma-like structures (MLS) were identified in glomerular endothelial cytoplasm and in the adjacent capitallary basement membrane. such endothelial cells often displayed enlargement and vacuolization, with MLS sometimes localized in clusters within the vacuoles.

Although 12 patients showed MLS within the glomerular basement membrane, seven patients, with mor eintense immunoperoxidase staining for the mycosplasmal antigens within this location demonstrated greater involvement of the memberane on electron microscopy. Mycoplasma-like structures could be seen in subendothelial, intramembranous, and subepithelial locations with accompanying membranopathic changes. These changes consisted of (1) small holes in the basement membrane surrounding intramembranous MLS, (2) splits and large irregular defects in the membrane associated with scattered MLS, (3) thickening of the membrane, associated with intramembranous MLS, and (4) complete breaks in the basement membrane in areas of heavy MLS infiltration.

Mycoplasma-like structures were also present within visceral epithelial cells which often displayed cytoplasmic degeneration, vacuolization, and partial detachment from the underlying basement membrane. In many instances these cells were completely detached from the basement membrane, embedded in proteinaceous cast material within Bowman's space.

Numerous MLS were likewise found within the contiguous large proteinaceous casts in microcystically dilated tubules. Morphologically, these particles varied from spherical electron-dense forms to large ovoid, flask-shaped or undulating forms. My coplasma-like structures were present in great numbers in detached, degenerated tubular epithelial cells, which were often incorporated into the casts.

Electron microscopic study of renal tissues of 10 of the 15 group B cases showed occasional mononuclear interstitial cells containing MLS. Group C cases displayed no MLS ultrastructurally. Glomerular endothelial tubuloreticular inclusions were present in the 15 group A and 10 group B cases, and were absent in the five group C cases.

In this study, we hae identified mycoplasmal infection of the parenchymal cells in kidneys of AIDS patients with typical histologic changes of AAN. There is good correlation between the immunohistochemical presence of the incognitus strain mycoplasmal antigens in visceral epithelial and tubular epithelial cells demonstrating the cytopathic changes typical of AAN, and the ultrastructural presence of MLS within the same critical cells. The same correlation also holds true for other microscopic locations, such as glomerular endothelial cells and renal tubular casts. The ultrastructural finding of significant numbers of MLS within the glomerular capillary basement membrane with evidence of membranopathic effect can be of particular importance when considering the pathogenesis of this nephropathy.

In summary, this study documents a spectrum of renal histopathologic changes which helps further delineate the morphogenesis of AAN. The study has also demonstrated the mycoplasmal infection of glomerular endothelium, epithelium, and basement membrane, as well as tubular epithelium, in the kidneys of AIDS patients with AAN. Infection of these functional parenchymal cells by $M.$ $fermentans$ (incognitus strain) may have contributed to the development of glomerulosclerosis, proteinuria, intratubular casts, and renal failure in these patients with AIDS.

EXAMPLE 24

Enhancement of HIV-1 Cytocidal Effects in CD4+ by $M.$ $fermentans$ incognitus

The effects of the $M.$ $fermentans$ incognitus on HIV-1 infection of a CD4+ human T lymphocyte cell line, designated previously as A3.01 (Folks, T. et al., Science 231, 600 (1986)).

Figure 35:
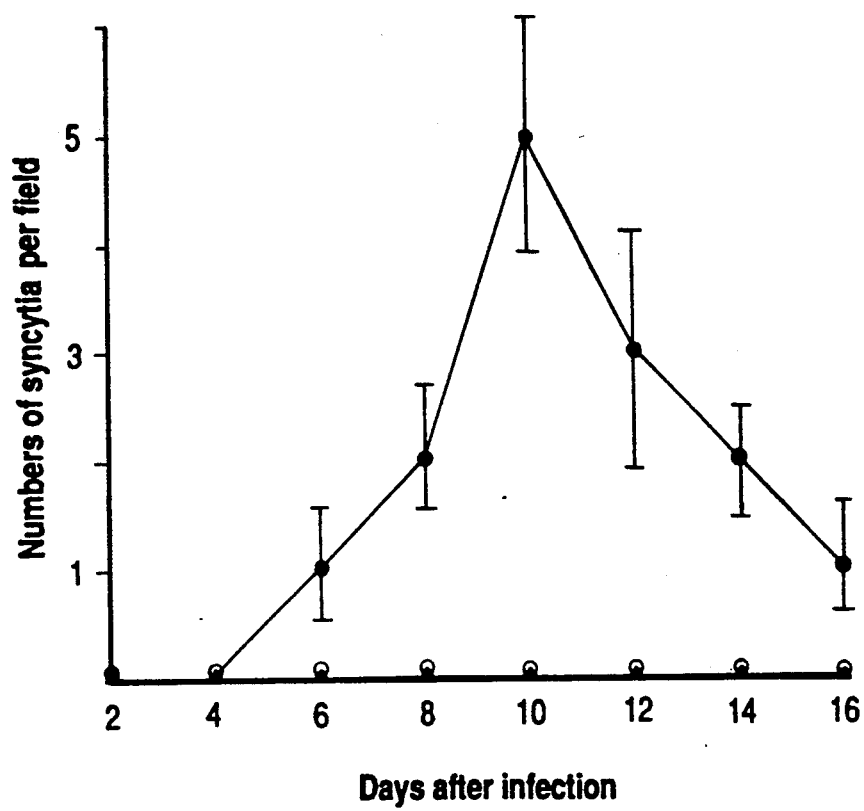
FIG. 35 shows the inhibition of HIV-1-induced syncytium formation by *M. fermentans* incognitus.

Normally, HIV-1 infection of human T lymphocytes in vitro produces pronounced cytopathic effects (CPE) with the release of newly replicated virus (Lifson et al., Science 232, 1123 (1960)). The formation of large multinucleated cells, termed syncytia, and high levels of reverse transcriptase (RT) activity is a characteristic feature of HIV-1 infection in vitro (Lifson et al., Nature 323, 725 (1986)). A3.01 cells ($5 \times 10^7$) were infected with (▲) HIV-1 ($1 \times 10^5$ infectious units) and incognitus strain ($1 \times 10^3$ infectious units), (●) HIV-1, or (0) incognitus strain. Cells in each culture were incubated at 37° C. for 2 hours and then washed once with RPMI 1640 medium. The infectious titer of HIV-1 was previously determined by exposing A3.01 cells to tenfold serial dilutions of HIV-1 culture stock for 2 hours at 37° C. The highest dilution in which the presence of RT activity could be detected after 14 days in culture represented one infectious unit. We grew the incognitus strain in modified SP-4 media and filter-cloned it three times from a single colony on agar plates (3). The organisms were washed once and resuspended in RPMI 1640. The titer of incognitus strain after infection of NIH 3T3 cells was determined by antigen dot blot assay. The cell cultures were maintained with RPMI 1640 supplemented with 10% FBS. Large numbers of syncytia formed when HIV-1 alone infected A3.01 cells, but syncytium formation disappeared in A3.01 cells simultaneously infected with HIV-1 and incognitus strain (FIG. 35) despite clear evidence of a cytocidal effect. Results are the average of the number of syncytia per field (X200) of ten fields examined per culture. The error bars indicate standard deviation of the mean.

Figure 36A:
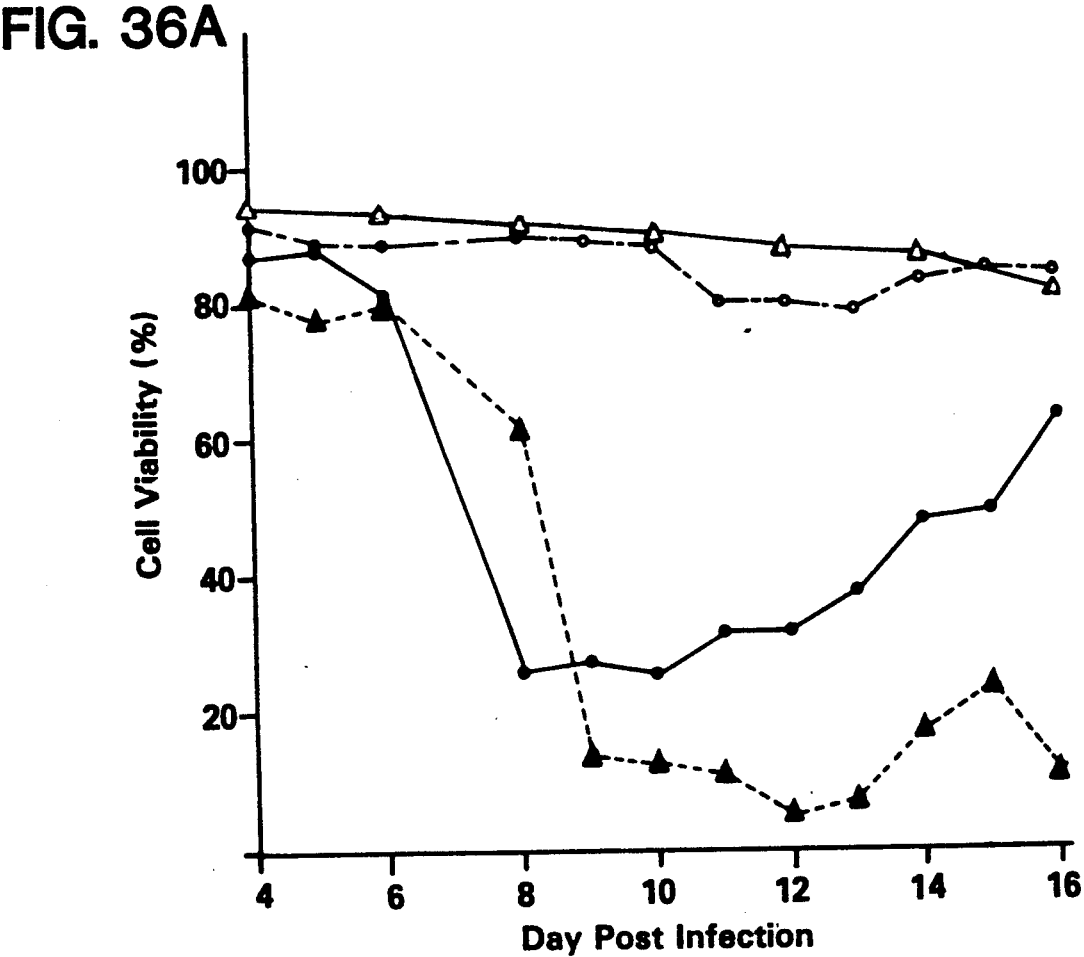
FIG. 36A shows the augmentation of cytocidal effect and inhibition of RT activity in HIV-1 infected A3.01 cells cultures by *M. fermentans* incognitus.
Figure 36B:
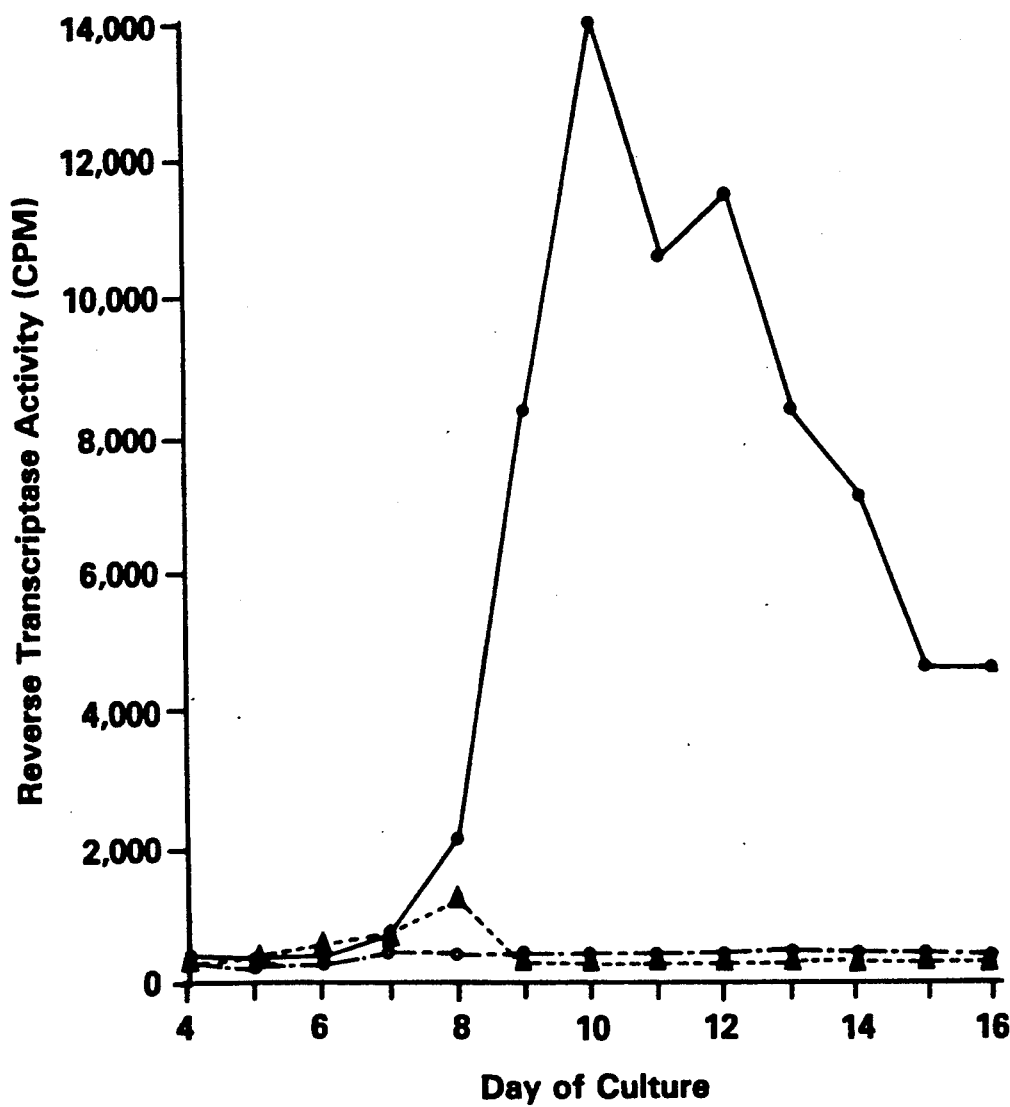
FIG. 36B shows the inhibition of RT activity in HIV-1 infected A3.01 cell cultures by *M. fermentans* incognitus.

The cytocidal effect and inhibition of RT activity in HIV-1 infected A3.01 cell cultures by $M.$ $fermentans$ incognitus was analyzed. A3.01 cells were cultured after (●) infection by HIV-1, (▲) infection by HIV-1 and incognitus strain, (Δ) infection by incognitus strain, or (*) no treatment. Each point on each graph is the average of the results of three indipendent cultures. (A) Cell viability was determined with the Trypan blue exclusion test with a total of 200 cells counted for each time point. (B) Samples of culture supernatants were tested daily with the standard RT enzyme assay using the incorporation of tritiated triphosphate nucleotides (Baltimore et al., *Proc. Natl. Acad. Sci. USA* 68, 1507 (1971). Conditions of HIV-1 and mycoplasma infectious were the same as described above. The culture infected by mycoplasma alone [indicated by $\Delta$ in (A)] also had no detectable RT activity. The *M. fermentans* incognitus significanly enhanced the cytocidal effects of HIV-1 infection in A3.01 cells (FIG. 36A). Furthermore, populations of cells that had been infected by HIV-1 alone gradually recovered from the initial cytocidal effect and remained persistently infected. In contrast, A3.01 cells infected by both HIV-1 and incognitus strain died. In this study, incognitus strain infection alone did not produce detectable cytotoxicity. As expected, culture supernatants from A3.01 cells infected with HIV-1 had clear RT activity. However, samples from the cointected cell culture shoed little or no RT activity (FIG. 36B).

Figure 37A:
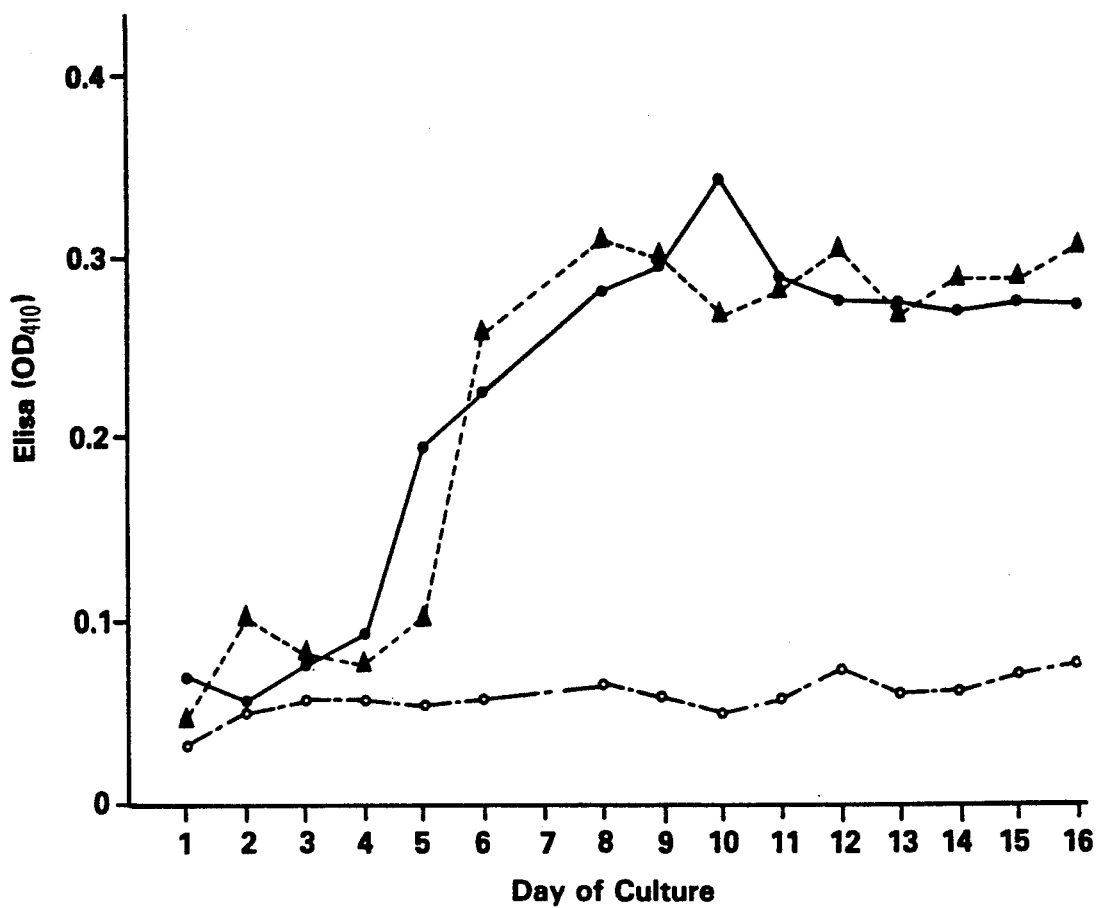
FIG. 37A shows continued viral production of HIV-1 and *M. fermentans* incognitus in culture supernatant by ELISA.
Figure 37B:
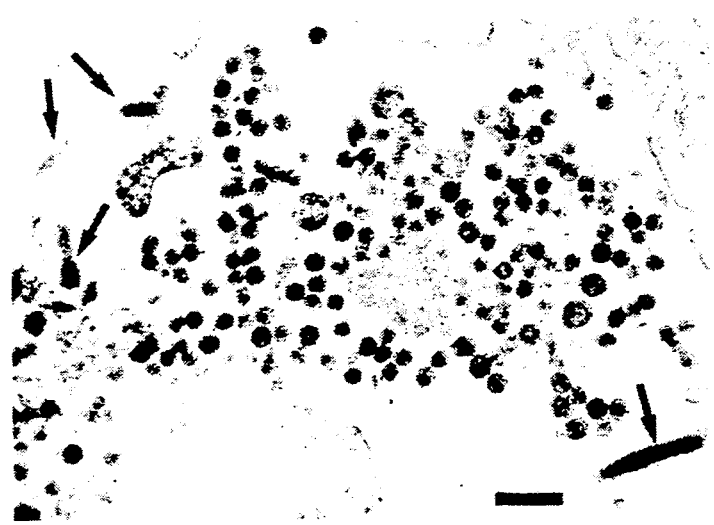
FIG. 37B shows continued viral production of HIV-1 and *M. fermentans* incognitus in culture supernatant by electron micrograph.

Despite the absence of RT activity, virus-specific protein synthesis and assembly was occurring. This activity was shown by examining culture supernatants. Culture supernantant (100 ul) was tested for the presence of viral antigen (HIV-1 antigen assay kit, Integrated Diagnostics, Gaithersburg, Md.). The assay kit uses an enzyme-linked immunosorbent assay (ELISA) technique, and the procedures performed in this study were in strict accordance to the instructions supplied with the kit. The negative control (phosphate-buffered saline) had an absorbance ($A_{410}$) reading of less than 0.1 at 410 nm. Each point on the graph (FIG. 37A) is the average of the results of three independent cultures. (●) A3.01+HIV-1, (▲) A3.01+HIV-1+incognitus strain, (*) A3.01 (FIG. 37B shows an electron micrograph of a cell culture infected simultaneously with both HIV-1 and incognitus strain. Numerous viral particles are seen in this culture with lytic cells. Occasional electron-dense forms of incognitus strain (arrows) can also be seen. Bar+400 nm. The coinfected cell culture produced HIV-1-specific p24–p25 as rapidly as the culture infected by HIV-1 alone (FIG. 37A). Electron microscopy of coinfected cells showed typical HIV virions (FIG. 37B). The assembled virions were infectious. Supernatant from the coinfected culture, which showed no detectable RT activity, was tenfold serially diluted and incubated with fresh A3.01 cells. We found comparable infectious units of HIV-1 ($10^5$ per milliliter) to be produced in the supernatants after infection of cell cultures either by HIV-1 alone or by both HIV-1 and incognitus strain (See, Lo et al., *Science* 251, 1074 (1991).

To test if substances in cultures infected by incognitus strain directly affected the RT enzyme assay, culture supernatant from A3.01 cells coinfected with HIV-1 and incognitus strain was mixed with the culture supernatant containing HIV with known RT activity. Over 90% of the Rt activity was inhibited when less than a third of the active supernatant was replaced by culture supernatants containing both HIV-1 and incognitus strain. Enzyme inhibition occurred immediately, and prior incubation of the mixture of culture supernatants was not required. We observed a comparable degree of inhibition when we used culture supernatant from A3.01 cells infected with only incognitus strain in the inhibition assay. Thus, the results can be best explained by the presence of some mycoplasma product or products in the assay lysate which directly interfered with the RT assay. Some mycoplasmas have recently been found to produce highly active nucleases (Marcus et al., *J. Cell Physiol* 143, 416 (1990), which could potentially be involved.

The masking effect of HIV RT activity may not be unique to incognitus strain. Suppression of HIV RT has recently been reported in M. hyorhinis-contaminated lymphocyte cultures (Vasndevachari et al., *AIDS Res. Hum. Retroviruses* 6, 411 (1990). But in contrast to the results in this report, the HIV-1-infected cultures contaminated by the swine mycoplasma still formed prominent syncytial cells. Our study indicates that syncytium formation and the actual cytocidal effect can be separate events. Our findings support the earlier reports (Sochoski, et al., *Nature* 322, 470 (1986); Somasundaran, et al., *J. Virol* 61, 3114 (1987) that state that the formation of syncytial cells is not a necessary prerequisite for proliferation of HIV-1.

It has recently been shown that nontoxic doses of the antibiotic tetracycline may significantly reduce the cytocidal effects of HIV-1 (Lemaitre, et al., *Res. Virol.* 141, 5 (1990). The tetracycline-treated cultures continued to produce a high titer of HIV-1. The authors suggested that a prokaryotic agent, most likely a mycoplasma, was involved with the cytocidal effect observed in the HIV-infected cultures. Indeed, additional study and characterization from their laboratory has confirmed that the hidden agent in the cultures is a mycoplasma (Wright, *Science* 248, 682 (1990).

Researchers from Japan have reported that just the antigens of killed mycoplasma (Acholeplasma laidlawii) could stimulate HIV-1 production (p24 antigen and infectious particles) in HIV-1-infected cells (Chorodhurg et al., *Lancet* 336, 247 (1990). In our study, approximately equivalent amounts of HIV antigen or infectious particles were produced in HIV-infected or HIV and incognitus strain-infected cultures despite significant differences in the numbers of viable cells. Thus, more HIV-1 may actually have been produced per individual cell in the coinfected culture; this finding is similar to the findings of the Japanese researchers.

AIDS patients can be infected with a number of pathogenic mircrobes and frequently are systemically infected with the incognitus strain (Lo et al., *Am. J. Trop. Med. Hyg.* 40, 213 (1989); Lo et al., Ibid 41, 601 (1989). Thus, the observation that coinfection by incognitus strain profoundly enhances cytocidal effects of HIV-1 infection in vitro.

While the invention has been described in connection with specific embodiments thereof, it will be understood that it is capable of further modifications. The description of the invention is intended to cover any variations, uses or adaptations of the invention following, in general, the principles of the invention, and includig such departures from the present disclosure as come within known and customary practice within the art to which the invention pertains.

What is claimed is:

1. A biologically pure mycoplasma isolated from tissues of patients with AIDS comprising the mycoplasma produced by the cell line ATCC No. CRL 9127.

2. A biologically pure mycoplasma having the identifying characteristics of *M. fermentans* incognitus, ATCC 53949.

* * * * *